(12) United States Patent
Saito et al.

(10) Patent No.: US 7,582,476 B2
(45) Date of Patent: Sep. 1, 2009

(54) ARTIFICIAL CELL COMPRISING MUTANT ESTROGEN RECEPTOR

(75) Inventors: Koichi Saito, Takarazuka (JP); Norihisa Ohe, Nara (JP); Hideo Satoh, Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 603 days.

(21) Appl. No.: 10/148,835

(22) PCT Filed: Dec. 1, 2000

(86) PCT No.: PCT/JP00/08553

§ 371 (c)(1), (2), (4) Date: Oct. 11, 2002

(87) PCT Pub. No.: WO01/42307

PCT Pub. Date: Jun. 14, 2001

(65) Prior Publication Data

US 2003/0207380 A1    Nov. 6, 2003

(30) Foreign Application Priority Data

| Dec. 7, 1999 | (JP) | ................................. 11/348022 |
| Dec. 27, 1999 | (JP) | ................................. 11/370667 |
| Jul. 7, 2000 | (JP) | ................................. 2000-207011 |
| Jul. 21, 2000 | (JP) | ................................. 2000-220508 |
| Aug. 2, 2000 | (JP) | ................................. 2000-234053 |
| Aug. 3, 2000 | (JP) | ................................. 2000-235460 |
| Aug. 3, 2000 | (JP) | ................................. 2000-235461 |
| Aug. 3, 2000 | (JP) | ................................. 2000-235463 |

(51) Int. Cl.
 *C12N 5/10* (2006.01)
 *C12N 15/11* (2006.01)
(52) U.S. Cl. ..................................... 435/325; 435/69.1
(58) Field of Classification Search ....................... None
 See application file for complete search history.

(56) References Cited

U.S. PATENT DOCUMENTS 5,508,164 A * 4/1996 Kausch et al. ................. 435/6
6,444,438 B1 * 9/2002 Chambon et al. .......... 435/69.1

FOREIGN PATENT DOCUMENTS

WO    87/05049    8/1997

OTHER PUBLICATIONS

England et al., International Journal of Oncology, 12: 981-986, 1998.
Katzenellenbogen et al., J. Steroid Biochem. Molec. Biol., vol. 53, No. 1-6, pp. 387-393, 1995.
Berry et al., The Embo Journal, vol. 9, No. 9, pp. 2811-2818 (1990).
Schwartz et al., J. Steroid Biochem. Molec. Biol., vol. 62, No. 2/3, pp. 173-184 (1997).
McDonnel et al., Bio/Technology, vol. 11, pp. 1256-1261 (1993).
Montano et al., molecular Endocrinology, vol. 10, No. 3, pp. 230-243 (1996).
Umekita et al., Jpn. J. Cancer Res., vol. 89, pp. 27-32, (1998).
Roodi et al., Journal of the National Cancer Institute, vol. 87, No. 6, (1995).

* cited by examiner

*Primary Examiner*—Michael Pak
(74) *Attorney, Agent, or Firm*—Birch Stewart Kolasch & Birch, LLP

(57) ABSTRACT

The present invention provides in general an artificial cell, an isolated mutant ERα, an isolated polynucleotide encoding the mutant ERα, a method for quantitatively analyzing an activity for transactivation of a reporter gene by a test ERα, a method for screening a mutant ligand dependent transcriptional factor, a method for evaluating an activity for transactivation of a reporter gene by a test ERα, a method for screening a compound useful for treating a disorder of a mutant ERα, a pharmaceutical agent useful for treating an estrogenic disorder of a mutant ERα, use of the mutant ERα, a method for diagnosing a genotype of a polynucleotide encoding a test ERα, a method for diagnosing a genotype of a polynucleotide encoding a test ERα and a method for diagnosing a phenotype of a test ERα.

26 Claims, 26 Drawing Sheets concentration of 4-hydroxytamoxifen concentration of ZM189154 concentration of 4-hydroxytamoxifen concentration of raloxifene concentration of 4-hydroxytamoxifen concentration of raloxifene normal ERα mutant ERαK531E

Dually transient reporter assay

Dually transient reporter assay

Dually transient reporter assay

Dually transient reporter assay

ARTIFICIAL CELL COMPRISING MUTANT ESTROGEN RECEPTOR

This application is the national phase under 35 U.S.C. 371 of PCT International Application No. PCT/JP00/08553 which has an International filing date of Dec. 1, 2000, which designated the United States of America.

1. TECHNICAL FIELD OF THE INVENTION

The present invention relates to ligand dependent transcriptional factors, such as an ERα, and to genes encoding a ligand dependent transcriptional factor. Further, the present invention relates to cells containing a ligand dependent transcriptional factor and a specified reporter gene for the ligand dependent transcriptional factor.

2. BACKGROUND OF THE INVENTION

Various cell mechanisms are regulated by ligand dependent transcriptional factors. The regulation by the ligand dependent transcriptional factors is usually achieved because the ligand dependent transcriptional factor has an activity for transactivation of a gene. It has been postulated that in transactivation, the ligand dependent transcription factor and a RNA polymerase II complex interact together at a gene to increase the rate of gene expression. The transactivation can often determine in eukaryotic cells, whether a gene is sufficiently expressed to regulate the various cell mechanisms.

Such transactivation by the ligand dependent transcriptional factors can occur when the ligand dependent tranactivational factor is selectively bound to its cognate ligand and to its cognate responsive element sequence. In this regard, the presence of the cognate responsive element in a gene or the presence of its cognate ligand in the cell can determine whether the ligand dependent transcriptional factor can transactivate the gene.

ERα is an example of such ligand dependent transcriptional factors. ERα is naturally found in the target cells of estrogen such as in ovary cells, breast cells, uterus cells, bone cells and the like. The transactivation activity of ERα typically occurs when ERα is selectively bound to an ERE and an estrogen such as E2. It is reported that aberrant transactivation by ERα may contribute to various disorders. Attempts have been made to use anti-estrogens that are antagonistic to a normal ERα. Examples of such anti-estrogens used with such disorders include tamoxifen, raloxifene, 4-hydroxytamoxifen and the like.

3. SUMMARY OF THE INVENTION

The present invention provides in general an artificial cell, an isolated mutant ERα, an isolated polynucleotide encoding the mutant ERα, a method for quantitatively analyzing an activity for transactivation of a reporter gene by a test ERα, a method for screening a mutant ligand dependent transcriptional factor, a method for evaluating an activity for transactivation of a reporter gene by a test ERα, a method for screening a compound useful for treating a disorder of a mutant ERα, a pharmaceutical agent useful for treating an estrogenic disorder of a mutant ERα, use of the mutant ERα, a method for diagnosing a genotype of a polynucleotide encoding a test ERα, a method for diagnosing a genotype of a polynucleotide encoding a test ERα and a method for diagnosing a phenotype of a test ERα.

4. DESCRIPTION OF FIGURES

FIGS. 1 to 32 illustrate the luciferase activity provided by a human mutant ERα or a human normal ERα. The reporter gene was expressed in the chromosomes of the cell. The mutant ERα gene was transiently expressed in the cell. FIGS. 1, 2, 4, 5, 7, 8, 12, 13, 16, 17 and 21 to 26 illustrate the luciferase activity in the presence of various concentrations of 4-hydroxytamoxifen, raloxifene or ZM189154 as the sole probable agent of stimulating a human mutant ERα or a human mutant ERα. FIGS. 3, 6, 9 to 11, 14, 15, 18 to 20, 27 to 32 illustrate the luciferase activity in the presence of various concentrations of 100 pM of E2 with various concentrations of 4-hydroxytamoxifen, raloxifene or ZM189154. A stable transformed cassette cell was utilized to transiently express the human mutant ERα gene or the human normal ERα gene as well as to express in a chromosome thereof the reporter gene. FIGS. 1, 2, 4, 5, 7, 8, 12, 13, 16, 17 and 21 to 26 zero together the luciferase activity by using the luciferase activity provided by the controls, in which the human mutant ERα or the human normal ERα was in the presence of DMSO (containing no 4-hydroxytamoxifen, raloxifene or ZM189154). FIGS. 3, 6, 9-11, 14, 15, 18 to 20, 27 to 32 zero together the luciferase activity by using the luciferase activity provided by the controls, in which the human mutant ERα or the human mutant ERα was in the presence of a DMSO solution containing 100 pM of E2. In zeroing the luciferase activity provided by the human mutant ERα and human normal ERα, the luciferase activity by the controls were set together as 100% luciferase activity. The luciferase activity provided by the controls in FIGS. 1, 2, 4, 5, 7, 8, 12, 13, 16, 17 and 21 to 26 is shown as DMSO. The luciferase activity provided by the controls in FIGS. 3, 6, 9-11, 14, 15, 18 to 20; 27 to 32 is shown as DMSO+E2.

FIGS. 33 to 48 illustrate the luciferase activity provided by a human mutant ERα or a human normal ERα. The reporter gene, the human mutant ERα gene and the human normal ERα were expressed in the chromosomes of the cell. FIGS. 33 to 40 illustrate the luciferase activity in the presence of various concentrations of 4-hydroxytamoxifen, ZM189154 or raloxifene as the sole probable agent of stimulating a human mutant ERα or a human normal ERα. FIGS. 41 to 48 illustrate the luciferase activity in the presence of 100 pM of E2 with various concentrations of 4-hydroxytamoxifen, ZM189154 or raloxifene. A stably transformed binary cell was utilized to express in the chromosomes, the reporter gene with the human mutant ERα gene or with the human normal ERα gene. FIGS. 33 to 40 zero together the luciferase activity provided by the controls, in which the human mutant ERα or the human normal ERα was in the presence of DMSO (containing no 4-hydroxytamoxifen, raloxifene or ZM189154). FIGS. 41 to 48 zero together the luciferase activity provided by the controls, in which the human mutant ERα or the human normal ERα was in the presence of a DMSO solution containing 100 pM of E2. In zeroing the luciferase activity provided by the human mutant ERα and human normal ERα, the luciferase activity by the controls were set together as 100% luciferase activity. The luciferase activity provided by the controls in FIGS. 33 to 40 is shown as DMSO. The luciferase activity provided by the controls in FIGS. 41 to 48 is shown as DMSO+E2.

FIGS. 49 to 52 illustrate, as a comparative example, the luciferase activity provided by a human mutant ERαK531E or a human normal ERα, in which the reporter gene was transiently expressed in the cell. FIGS. 49 and 50 illustrate the luciferase activity in the presence of various concentrations of 4-hydrozytamoxifen as the sole probable agent of stimulating a human mutant ERα. FIGS. 51 and 52 illustrate the luciferase activity in the presence of 100 pM of E2 with various concentrations of 4-hydroxytamoxifen. FIGS. 49 and 50 zero together the luciferase activity of the controls, in which the human normal ERα or the human mutant ERαK531E was in the presence of DMSO (containing no 4-hydrozytamoxifen). FIGS. 51 and 52 zero together the luciferase activity of the controls, in which the human normal ERα or the human mutant ERαK531E was in the presence of a DMSO solution containing 100 pM of E2. In zeroing the luciferase activity provided by the human mutant ERα and human normal ERα, the resulting luciferase activity by the controls is set as 100% luciferase activity. The luciferase activity provided by the controls in FIGS. 49 and 50 is shown as DMSO. The luciferase activity provided by the controls in FIGS. 51 and 52 is shown as DMSO+E2.

5. DETAILED DESCRIPTION OF THE INVENTION

5.1. Definitions

AR: means the androgen receptor protein.

E2: means estradiol.

ERα: means an estrogen receptor α protein. Specified mutants of ERα are referred to herein by a letter-number-letter combination following the phrase "mutant ERα", such as by K303R, S309F, G390D, M396V, G415V, G494V, K531E and S578P. In the letter-number-letter combination, the number indicates the relative position of a substituted amino acid in the mutant ERα, the letter preceding the number indicates the amino acid in a normal ERα at the indicated relative position and the letter following the number indicates the substituted amino acid in the provided mutant ERα at the indicated relative position. When there are two substituted amino acids in the mutant ERα, the phrase "mutant ERα" is followed by two letter-number-letter combinations, such as by G390D/S578P.

ERβ: means the estrogen receptor β protein.

GR: means the glucocorticoid receptor protein.

MR: means the mineralocorticoid receptor protein.

PPAR: means the peroxisome proliferator-activated receptor protein.

PR: means the progesterone receptor protein.

PXR: means the pregnane X receptor protein.

TR: means the thyroid hormone receptor protein.

VDR: means the vitamin D receptor protein.

DR1: means the receptor responsive sequence having the following nucleotide sequence:

5'-AGGTCAnAGGTCA-3' wherein n represents an A, C, T or G.

DR3: means the receptor responsive sequence having the following nucleotide sequence:

5'-AGGTCAnnnAGGTCA-3' wherein n represents an A, C, T or G.

DR4: means the receptor responsive sequence having the following nucleotide sequence:

5'-AGGTCAnnnnAGGTCA-3' wherein n represents an A, C, T or G.

ERE: means the estrogen responsive element nucleotide sequence.

MMTV: means the mouse mammary tumor virus

5.2. The Cell

The cell of the present invention comprises a chromosome which comprises a reporter gene. The reporter gene in the chromosome comprises an ERE, a TATA sequence and a reporter sequence. In addition, the cell comprises a mutant ERα or a gene encoding the mutant ERα. In this regard, the cell provides a biological system in which the mutant ERα can have an activity for transactivation of the reporter gene. The activity for transactivation of the reporter gene by the mutant ERα in the presence of E2 and a partial anti-estrogen is typically higher than that by a normal ERα in the presence of E2 and the partial anti-estrogen. Alternatively, the activity for transactivation of the reporter gene by the mutant ERα in the presence of the partial anti-estrogen as the sole probable agent of stimulating the mutant ERα is typically higher than that by the normal ERα in the presence of the partial anti-estrogen as the sole probable agent of stimulating the normal ERα.

Typically, the ERE, the TATA sequence and the reporter sequence are organized in the reporter gene to allow the transactivation of the reporter gene. For example, the reporter gene can have the ERE operably upstream from the TATA sequence and the reporter sequence operably downstream from the TATA sequence. If so desired, the reporter gene may additionally contain conventional nucleotide sequences advantageous for the expression of the reporter gene.

The TATA sequence may have the following nucleotide sequence:

5'-TATAA-3'

In a natural cell, the ERE is a receptor responsive sequence that is cognate with a normal ERα. When normal ERα binds to E2 and the normal ERα-E2 complex binds to the ERE, the normal ERα has an activity for transactivation. In the cell, it is a function of the ERE to bind to the mutant ERα and allow the mutant ERα to have an activity for transactivation of the reporter gene. Typically, such an ERE is encompassed by the following nucleotide sequence:

5'-AGGTCAnnnTGACCTT-3' wherein n represents an A, G, C or T. Further, a tandem repeat of the ERE in the reporter gene can provide a more efficient activity for transactivation of the reporter gene. A 2 to 5 tandem repeat of the ERE may be used in the reporter gene. As an example of an ERE which can be utilized in the reporter gene, there is mentioned an ERE derived from *Xenopus vitellogenin* gene (Cell, 57, 1139-1146). The ERE can be prepared for the reporter gene by being chemically synthesized or by being cloned with polymerase chain reaction (PCR) amplification methods.

The reporter sequence in the reporter gene is a reporter sequence naturally foreign to the ERE. As such, the reporter sequence and the ERE are not found together in a natural gene. Further, when such a reporter sequence encodes a reporter protein, the reporter sequence typically encodes a reporter protein that is more or less active in the cell. As examples of the reporter protein, there is mentioned a luciferase, a secretory alkaline phosphatase, a β-galactosidase, a chloramphenicol acetyl transferase, a growth hormone and the like.

Conventional methods may be used to ligate the ERE, the TATA sequence and the reporter sequence. After producing the reporter gene, the reporter gene may be inserted into a chromosome. The reporter gene may be inserted into a chromosome when the reporter gene is introduced into a host cell. Such methods of introducing the reporter gene into a host cell are described below.

The mutant ERα in the cell typically has a particular activity for transactivation of the reporter gene when in the presence of E2 and a partial anti-estrogen or when in the presence of the partial anti-estrogen as the sole probable agent of stimulating the mutant ERα. The activity for transactivation provided by the mutant ERα in the presence of E2 and the partial anti-estrogen is typically higher than that by a normal ERα in the presence of E2 and the partial anti-estrogen. The activity for transactivation of the reporter gene by the mutant ERα in the presence of the partial anti-estrogen as the sole probable agent of stimulating the mutant ERα is higher than that by the normal ERα in the presence of the partial anti-estrogen as the sole probable agent of stimulating the normal ERα. Since transactivation involves the increase of rate of transcription, such a transactivation by the normal ERα and mutant ERα can be observed by measuring the expression level of the reporter gene. When the expression levels of the reporter gene provided by the mutant ERα and normal ERα are adjusted to be zeroed at identical points, the mutant ERα would provide a higher expression level than that provided by the normal ERα.

Further, it should be noted that the mutant ERα may have the activity for transactivation of the reporter gene inhibited in the presence of the pure anti-estrogen. Such a activity for transactivation for the reporter gene provided by the mutant ERα is similar to the inhibition of the activity for transactivation of the reporter gene provided by the normal ERα in the presence of the pure anti-estrogen.

A normal ERα encompasses the ERα which is reported as most commonly carried in a species, such as human, monkey, mouse, rabbit, rat and the like. For example, a human normal ERα has the amino acid sequence shown in SEQ ID:1. Such a human normal ERα is described in Tora L. et al., EMBO, vol 8 no 7: 1981-1986 (1989).

The partial anti-estrogens typically are not antagonistic to an AF1 region of the normal ERα and are antagonistic to an AF2 region of a normal ERα. The AF2 region of a normal ERα and the AF1 region of a normal ERα are each regions in the normal ERα that are involved in transactivation by the normal ERα (Metzger D. et al., J. Biol. Chem., 270:9535-9542 (1995)).

Such properties of the partial anti-estrogens may be observed, for example, by carrying out the reporter assay described in Berry M. et al., EMBO J., 9:2811-2818 (1990). In such a reporter assay, there is utilized cells in which the AF1 region of an endogenous normal ERα has a strong activity for transactivation, such as chicken embryo fibroblast cells in primary culture (that may be prepared according to the description, for example, in Solomon, J. J., Tissue Cult. Assoc. Manual., 1:7-11 (1975)). When utilized, the chicken embryo fibroblast are modified so that the modified fibroblasts express therein a gene encoding the normal ERα and so that the modified fibroblasts have the reporter gene (herein-after referred to as AF1 evaluation fibroblasts). When the AF1 evaluation fibroblasts are exposed with a sufficient amount of a partial anti-estrogen, it can be determined whether the partial anti-estrogen fails to be antagonistic to an AF1 region of a normal ERα. The partial anti-estrogen in such cases increase the expression level of the reporter gene in the AF1 evaluation fibroblasts. Further, the chicken embryo fibroblast cells in primary culture are then modified for a second round so that the second modified fibroblasts express a gene encoding a truncated normal ERα which has the AF1 region deleted and so that the second modified fibroblasts have the reporter gene (hereinafter referred to as AF2 evaluation fibroblasts). When the AF2 evaluation fibroblasts are exposed with a sufficient amount the partial anti-estrogen, it can be determined whether the partial anti-estrogen is antagonistic to an AF2 region of a normal ERα. The partial anti-estrogen in such cases fails to increase the expression level of the reporter gene in the AF2 evaluation fibroblasts.

Examples of such parital anti-estrogens include tamoxifen, 4-hydroxytamoxifen, raloxifene and the like.

The pure anti-estrogen is typically an anti-estrogen which is fully antagonistic to a normal ERα. In this regard, the pure anti-estrogen fails to be partially agonistic to the ERα. In a reporter assay with either the AF1 evaluation fibroblasts or the AF2 evaluation fibroblasts, the pure anti-estrogen provides substantially no activity for transactivation of the reporter gene by the normal ERα or truncated normal ERα therein. As such, the expression level of the reporter gene in such reporter assays with the pure-anti-estrogen and either of the AF1 evaluation fibroblasts or AF2 evaluation fibroblasts does not substantially increase.

Examples of such pure anti-estrogen include ICI 182780 (Wakeling A E et al., Cancer Res., 512:3867-3873 (1991)), ZM 189154 (Dukes M et al., J. Endocrinol., 141:335-341 (1994)) and the like.

The mutant ERα comprises one or more substituted amino acids which confers such an activity for transactivation of the reporter gene in the presence of E2 and the partial anti-estrogen or in the presence of the partial anti-estrogen as the sole probable agent of stimulating the mutant ERα. Typically, the one or more substituted amino acids are present in the mutant ERα at one or more relative positions of from 303 to 578. For example, the mutant ERα may comprise one or more substituted amino acids at one or more relative positions selected from 303, 309, 390, 396, 415, 494, 531, 578 and the like. Typically, such relative positions in the mutant ERα are based on a homology alignment to the amino acid sequence shown in SEQ ID:1.

In general, a homology alignment encompasses an alignment of amino acid sequences based on the homology of the provided amino acid sequences. For example, Table 1 below randomly sets forth a homology alignment with the amino acid sequence shown in SEQ ID:1 (a human normal ERα), a mouse ERα (Genbank Accession No. M38651), a rat ERα (X6) (Genbank Accession No. X61098) and a rat ERα(Y0) (Genbank Accession No. Y00102).

TABLE 1

```
hERa.txt       1: M T M T L H T K A S G M A L L H Q I Q G N E L E P L N R P Q L K I P L E R P L G E V Y L D S S K P A V Y N Y P E G A A Y   60
mER.txt        1: M T M T L H T K A S G M A L L H Q I Q G N E L E P L N R P Q L K M P M E R A L G E V Y V D W S K P T V F N Y P E G A A Y   60
ratER(X6).txt  1: M T M T L H T K A S G M A L L H Q I Q G N E L E P L N R P Q L K M P M E R A L G E V Y V D W S K P A V F N Y P E G A A Y   60
ratER(Y0).txt  1: M T M T L H T K A S G M A L L H Q I Q G N E L E P L D R P Q L K M P M E R A L G E V Y V D W S K P A V F N Y P E G A A Y   60 hERa.txt      61: E F N A A A A A A N A Q - - - - V Y G Q T G L P Y G P G S E A A A F G S N G L G G F P P L N S V S P S P L M L L H P P P  115
mER.txt       61: E F N A A A A A A A A A A A S A P - V Y G Q S G I A Y G P G S E A A A F S A N S L G A F P Q L N S V S P S P L M L L H P P P  119
ratER(X6).txt 61: E F N A A A A A A A A A A A V Y G Q S S I T Y G P G S E A A A F G A N S L G A F P Q L N S V S P S P L M L L H P P P  120
ratER(Y0).txt 61: E F N A A A A A A A A A A A V Y G Q S S I T Y G P G S E A A A F G A N S L G A F P Q L N S V S P S P L M L L H P P P  120 hERa.txt     116: Q L S P F L Q P H G Q Q V P P Y Y L E N E P S G Y T V R E A G P P A F Y R P N S D N R R Q G R E R L A S T N D K G S M A  175
mER.txt      120: Q L S P F L H P H G Q Q V P P Y Y L E N E P S A Y A V R D T G P P A F Y R S N S D N R R Q N G R E R L S S I S N E K G N M I  179
ratER(X6).txt 121: H V S P F L H P H G H Q V P P Y Y L E N E P S A Y A V R D T G P P A F Y R S N S D N R R Q N G R E R L S S I S S E K G N M I  180
ratER(Y0).txt 121: H V S P F L H P H G H Q V P P Y Y L E N E P S A Y A V R D T G P P A F Y R S N S D N R R Q N G R E R L S S I S S E K G N M I  180 hERa.txt     176: M E S A K E T R Y C A V C N D Y A S G Y H Y G V W S C E G C K A F F K R S I Q G H N D Y M C P A T N Q C T I D K W R R K  235
mER.txt      180: M E S A K E T R Y C A V C N D Y A S G Y H Y G V W S C E G C K A F F K R S I Q G H N D Y M C P A T N Q C T I D K W R R K  239
ratER(X6).txt 181: M E S A K E T R Y C A V C N D Y A S G Y H Y G V W S C E G C K A F F K R S I Q G H N D Y M C P A T N Q C T I D K W R R K  240
ratER(Y0).txt 181: M E S A K E T R Y C A V C N D Y A S G Y H Y G V W S C E G C K A F F K R S I Q G H N D Y M C P A T N Q C T I D K W R R K  240 hERa.txt     236: S C Q A C R L R K C Y E V G M M K G G I R K D R R G G R M L K H K R Q R D D G E G R G E V G S A G D M R A A N L W P S P  295
mER.txt      240: S C Q A C R L R K C Y E V G M M K G G I R K D R R G G R M L K H K R Q R D D L E G R N E M G A S G D M R A A N L W P S P  299
ratER(X6).txt 241: S C Q A C R L R K C Y E V G M M K G G I R K D R R G G R M L K H K R Q R D D L E G R N E M G T S G D M R A A N L W P S P  300
ratER(Y0).txt 241: S C Q A C R L R K C Y E V G M M K G G I R K D R R G G R M L K H K R Q R D D L E G R N E M G T S G D M R A A N L W P S P  300 hERa.txt     296: L M I K R S K K N S L A L S L T A D Q M V S A L L D A E P P I L Y S E Y D P T R P F S E A S M M G L L T N L A D R E L V  355
                              *
mER.txt      300: L V I K H T K K N S P A L S L T A D Q M V S A L L D A E P P M I Y S E Y D P S R P F S E A S M M G L L T N L A D R E L V  359
ratER(X6).txt 301: L V I K H T K K N S P A L S L T A D Q M V S A L L D A E P P L I Y S E Y D P S R P F S E A S M M G L L T N L A D R E L V  360
ratER(Y0).txt 301: L V I K H T K K N S P A L S L T A D Q M V S A L L D A E P P L I Y S E Y D P S R P F S E A S M M G L L T N L A D R E L V  360 hERa.txt     356: H M I N W A K R V P G F V D L T L H D Q V H L L E C A W L E I L M I G L V W R S M E H P G K L L F A P N L L L D R N Q G  415
mER.txt      360: H M I N W A K R V P G F G D L N L H D Q V H L L E C A W L E I L M I G L V W R S M E H P G K L L F A P N L L L D R N Q G  419
ratER(X6).txt 361: H M I N W A K R V P G F G D L N L H D Q V H L L E C A W L E I L M I G L V W R S M E H P G K L L F A P N L L L D R N Q G  420
ratER(Y0).txt 361: H M I N W A K R V P G F G D L N L H D Q V H L L E C A W L E I L M I G L V W R S M E H P G K L L F A P N L L L D R N Q G  420 hERa.txt     416: K C V E G M V E I F D M L L A T S S R F R M M N L Q G E E F V C L K S I T I L L N S G V Y T F L S S T L K S L E E K D H I  475
mER.txt      420: K C V E G M V E I F D M L L A T S S R F R M M N L Q G E E F V C L K S I I L L L N S G V Y T F L S S T L K S L E E K D H I  479
ratER(X6).txt 421: K C V E G M V E I F D M L L A T S S R F R M M N L Q G E E F V C L K S I I L L L N S G V Y T F L S S T L K S L E E K D H I  480
ratER(Y0).txt 421: K C V E G M V E I F D M L L A T S S R F R M M N L Q G E E F V C L K S I I L L L N S G V Y T F L S S T L K S L E E K D H I  480 hERa.txt     476: H R V L D K I T D T L I H L M A K A G L T L Q Q Q H Q R L A Q L L L I L S H I R H M S N K G M E H L Y S M K C K N V V P  535
mER.txt      480: H R V L D K I T D T L I H L M A K A G L T L Q Q Q H R R L A Q L L L I L S H I R H M S N K G M E H L Y N M K C K N V V P  539
ratER(X6).txt 481: H R V L D K I T D T L I H L M A K A G L T L Q Q Q H R R L A Q L L L I L S H I R H M S N K G M E H L Y N M K C K N V V P  540
ratER(Y0).txt 481: H R V L D K I N D T L I H L M A K A G L T L Q Q Q H R R L A Q L L L I L S H I R H M S N K G M E H L Y N M K C K N V V P  540
```

TABLE 1-continued

| | | | | | | | | | | | | | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hERα.txt | 536: | L | Y | D | L | L | L | E | M | L | D | A | H | R | L | H | A | P | T | S | R | G | G | A | S | V | E | E | T | D | Q | S | H | L | A | T | A | G | S | T | S | S | H | S | L | Q | K | Y | Y | I | T | G | E | A | E | G | F | P | A | T | V | 595 |
| mER.txt | 540: | L | Y | D | L | L | L | E | M | L | D | A | H | R | L | H | A | P | A | S | R | M | G | V | P | P | E | E | P | S | Q | T | Q | L | A | T | T | S | S | T | S | A | H | S | L | Q | T | Y | Y | I | P | P | E | A | E | G | F | P | N | T | I | 599 |
| ratER(X6).txt | 541: | L | Y | D | L | L | L | E | M | L | D | A | H | R | L | H | A | P | A | S | R | M | G | V | P | P | E | E | P | S | Q | S | Q | L | T | T | T | S | S | T | S | A | H | S | L | Q | T | Y | Y | I | P | P | E | A | E | G | F | P | N | T | I | 600 |
| ratER(Y0).txt | 541: | L | Y | D | L | L | L | E | M | L | D | A | H | R | L | H | A | P | A | S | R | M | G | V | P | P | E | E | P | S | Q | S | Q | L | T | T | T | S | S | T | S | A | H | S | L | Q | T | Y | Y | I | P | P | E | A | E | G | F | P | N | T | I | 600 |

In Table 1, "hERa.TXT" sets forth the amino acid sequence shown in SEQ ID:1. "mER.TXT" sets forth the amino acid sequence of the mouse ERα, "ratER(X6).TXT" sets forth the amino acid sequence of the rat ERα(X6) and "ratER(Y0)" sets forth the amino acid sequence of rat ERα(Y0), wherein amino acids sequences thereof are set forth using one letter abbreviations of the amino acids. This alignment was prepared using a commercially available software GENETYX-WIN SV/R ver. 4.0 (Software Development Co.). The symbol "*" indicates the amino acids located at relative positions 303 and 578.

The relative positions under the homology alignment correspond to the absolute positions of the amino acid sequence shown in SEQ ID:1. For example, relative position 303 encompasses under the homology alignment, the amino acid in the mutant ERα aligned with the 303rd amino acid from the N-terminus in the amino acid sequence shown in SEQ ID:1. Further, a relative position 578 encompasses under the homology alignment, the amino acid in the mutant ERα aligned with the 578th amino acid from the N-terminus in the amino acid sequence shown in SEQ ID:1. In reference to Table 1, examples of relative position 303 include the lysine that is the 303rd amino acid from the amino terminus in the amino acid sequence shown in SEQ ID:1, the lysine that is the 307th amino acid from the amino terminus in the amino acid sequence of the mouse ERα, the lysine that is the 308th amino acid from the amino terminus in the amino acid sequence of rat ERα(X6) and the lysine that is the 308th amino acid from the amino terminus in the amino acid sequence of the rat ERα(Y0). Further, examples of the relative position 578 in reference to Table 1 include the serine that is the 578th amino acid from the amino terminus in the amino acid sequence shown in SEQ ID NO: 1, the serine that is the 582th amino acid from the amino terminus in the amino acid sequence of the mouse ERα, the serine that is the 583th amino acid from the amino terminus in the amino acid sequence of the rat ERα(X6) and the serine that is the 583th amino acid from the amino terminus in the amino acid sequence of rat ERα(Y0).

In this regard, the homology alignment in connection with the present invention aligns the amino acid sequence shown in SEQ ID:1 with an amino acid sequence encoding mutant ERα, based on the homology of the mutant ERα and the amino acid sequence shown SEQ ID:1. When aligning the amino acid sequence of a mutant ERα in the homology alignment to amino acid sequence SEQ ID:1, such a mutant ERα typically has at least an 80% homology with the amino acid sequence shown in SEQ ID:1.

The mutant ERα can be derived from an animal such as a manual. Examples of such mammals include human, monkey, rabbit, rat, mouse and the like. For the human mutant ERα, the mutant ERα generally has an amino acid length of 595 amino acids.

In having the substituted amino acid at relative position 303, the mutant ERα may be derived from changing the lysine present at relative position 303 in a normal ERα into a substituted amino acid. In such cases, the mutant ERα may have the substituted amino acid at relative position 303 be arginine, such as a mutant ERα K303R. The human mutant ERα K303R has the amino acid sequence shown in SEQ ID:2.

In having the substituted amino acid at relative position 309, the mutant ERα may be derived from changing the serine present at relative position 309 in a normal ERα into a substituted amino acid. In such cases, the mutant ERα may have the substituted amino acid at relative position 309 be phenylalanine, such as a mutant ERα S309F. The human mutant ERα S309F has the amino acid sequence shown in SEQ ID:3.

In having the substituted amino acid at relative position 390, the mutant ERα may be derived from changing the glycine present at relative position 390 in a normal ERα into a substituted amino acid. In such cases, the mutant ERα may have the substituted amino acid at relative position 390 be aspartic acid, such as a mutant ERα G390D. The human mutant ERα G390D has the amino acid sequence shown in SEQ ID:4.

In having the substituted amino acid at relative position 396, the mutant ERα may be derived from changing the methionine present at relative position 396 in a normal ERα into a substituted amino acid. In such cases, the mutant ERα may have the substituted amino acid at relative position 396 be valine, such as a mutant ERα M396V. The human mutant ERα M396V has the amino acid sequence shown in SEQ ID:5.

In having the substituted amino acid at relative position 415, the mutant ERα may be derived from changing the glycine present at relative position 415 in a normal ERα into a substituted amino acid. In such cases, the mutant ERα may have the substituted amino acid at relative position 415 be valine, such as a mutant ERα G415V. The human mutant ERα G415V has the amino acid sequence shown in SEQ ID:6.

In having the substituted amino acid at relative position 494, the mutant ERα may be derived from changing the glycine present at relative position 494 in a normal ERα into a substituted amino acid. In such cases, the mutant ERα may have the substituted amino acid at relative position 494 be valine, such as a mutant ERα G494V. The human mutant ERα G494V has the amino acid sequence shown in SEQ ID:7.

In having the substituted amino acid at relative position 531, the mutant ERα may be derived from changing the lysine present at relative position 531 in a normal ERα into a substituted amino acid. In such cases, the mutant ERα may have the substituted amino acid at relative position 531 be glutamic acid, such as a mutant ERα K531E. The human mutant ERα K531E has the amino acid sequence shown in SEQ ID:8.

In having the substituted amino acid at relative position 578, the mutant ERα may be derived from changing the serine present at relative position 578 in a normal ERα into a substituted amino acid. In such cases, the mutant ERα may have the substituted amino acid at relative position 578 be proline, such as mutant ERα S578P. The human mutant ERα S578P has the amino acid sequence shown in SEQ ID:9.

In having the substituted amino acid at relative position 390 and 578, the mutant ERα may be derived from changing the glycine present at relative position 390 in a normal ERα into a substituted amino acid as well as changing the serine present at relative position 578 in the normal ERα into another substituted amino acid. In such cases, the mutant ERα may have the substituted amino acid at relative position 390 be aspartic acid and the substituted amino acid at relative position 578 be proline, such as mutant ERα G390D/S578P. The human mutant ERα G390D/S578P has the amino acid sequence shown in SEQ ID:10.

To provide the mutant ERα, the cell may express a gene encoding the mutant ERα, according to the standard genetic code which is well known. Such a mutant ERα gene typically comprises a polynucleotide which encodes the mutant ERα and a promoter. The mutant ERα gene can be isolated from tissue sample. Further, the mutant ERα gene may be produced by using mutagenesis techniques to mutagenize a polynucleotide encoding a normal ERα to encode the mutant ERα and by operably linking a promoter upstream from the resulting polynucleotide encoding the mutant ERα. The mutagenesis techniques, such as site-directed mutagenesis, may be utilized to introduce the one or more mutations into the normal ERα polynucleotide and provide a mutant ERα polynucleotide. The human normal ERα polynucleotide having the nucleotide sequence described in Tora L. et al. EMBO J., vol 8 no 7:1981-1986 (1989) is utilized in the case of mutagenizing the human normal ERα polynucleotide.

The promoter in the mutant ERα gene initiates transcription so that the mutant ERα can be expressed to provide the mutant ERα in the cell. In this regard, a promoter capable of functioning in the cell is usually operably linked upstream to a polynucleotide encoding the mutant ERα. For instance, where the cell is derived from an animal host cell or fission yeast host cell, examples of the promoter may include *Rous sarcoma* virus (RSV) promoter, cytomegalovirus (CMV) promoter, early and late promoters of simian virus (SV40), MMTV promoter and the like. Where the cells are derived from budding yeast host cell, examples of the promoter may include ADH1 promoter and the like.

In using the mutagenesis techniques, a polynucleotide encoding normal ERα can be isolated and then the isolated normal ERα polynucleotide can be mutagenized by using oligonucleotides. The resulting mutant ERα polynucleotide can then be utilized to produce the mutant ERα gene.

Oligonucleotides are designed and synthesized to specifically amplify a cDNA encoding a normal ERα from a cDNA library or the cDNAs of an animal. Such oligonucleotides can be designed, based on a well known nucleotide sequence encoding the normal ERα, such as the normal ERα nucleotide sequences found in documents, such as Tora L. et al. EMBO J., vol 8 no 7:1981-1986 (1989), or in databases such as in Genbank. As such normal ERα nucleotide sequences, there can be utilized a normal ERα nucleotide sequence derived from human, monkey, rabbit, rat, mouse or the like. The designed oligonucleotides can then be synthesized with a DNA synthesizer (Model 394, Applied Biosystems). A polymerase chain reaction (PCR) amplification may then be utilized to isolate the normal ERα polynucleotide from the cDNA library or cDNAs. For human normal ERα gene, the oligonucleotides depicted in SEQ ID:11 and SEQ ID:12 may be utilized to PCR amplify the human normal ERα polynucleotide having the nucleotide sequence described in Tora L. et al. EMBO J., vol 8 no 7:1981-1986 (1989).

The cDNAs can be derived from animal tissue (such as human, monkey, rabbit, rat, or mouse) according to genetic engineering techniques described in J. Sambrook, E. F. Frisch, T. Maniatis, "Molecular Cloning, 2nd edition", Cold Spring Harbor Laboratory, 1989. In such techniques, the RNAs in an animal tissue, such as liver or uterus, are collectively extracted therefrom and the RNAs are collectively reverse transcribed into the cDNAs of the animal. For example, the animal tissue is first homogenized in a buffer containing a protein denaturing agent such as guanidine hydrochloride or guanidine thiocyanate. Reagents such as a mixture containing phenol and chloroform (hereinafter referred to as phenol-chloroform) are further added to denature proteins resulting from homogenizing the animal tissue. After removing the denatured proteins by centrifugation, the RNAs are collectively extracted from the recovered supernatant fraction. The RNAs can be collectively extracted by methods such as the guanidine hydrochloride/phenol method, SDS-phenol method, the guanidine thiocyanate/CsCl method and the like. ISOGEN (Nippon Gene) is an example of a commercially available kit which is based on such methods of collectively extracting the RNAs. After collectively extracting the RNAs, oligo-dT primers are allowed to anneal to the poly A sequence in the RNAs to collectively reverse transcribe the RNAs as a template. A reverse transcriptase can be utilized to collectively reverse transcribe the RNAs into single-stranded cDNAs. The cDNAs can be synthesized from the single-strand cDNAs by using *E. coli* DNA polymerase I with the above single-stranded cDNAs. In using *E. coli* DNA polymerase I, *E. coli* RNase H is also used to produce primers, which allow *E. coli* DNA polymerase I to operate more efficiently. The cDNAs can be purified by using conventional purifying procedures, for example, by phenol-chloroform extraction and ethanol precipitation. Examples of commercially available kits based on such methods include cDNA Synthesis System Plus (Amersham Pharmacia Biotech), TimeSaver cDNA Synthesis kit (Amerham Pharmacia Biotech) and the like.

The normal ERα polynucleotide is then isolated from the cDNAs. Isolation procedures which may be utilized to isolate the normal ERα polynucleotide may include using PCR amplification. The PCR amplification typically amplifies the normal ERα polynucleotide from the cDNAs. The PCR mixture in the PCR amplification may contain a sufficient amount of the cDNAs, a sufficient amount of the forward and reverse oligonucleotides, a heat tolerant DNA polymerase (such as LT-Taq polymerase (Takara Shuzo)), dNTPs (dATP, dTTP, dGTP, dCTP) and a PCR amplification buffer. In a PCR mixture amplifying a human normal ERα polynucleotide, there may be utilized 10 ng of the cDNAs and 10 pmol of the each of the forward and reverse oligonucleotides (SEQ ID:11 and SEQ ID:12). The PCR mixture in the PCR amplification then undergoes an incubation cycle for annealing, elongation and denaturing. For example, the PCR amplification may have repeated 35 times with a thermal cycler such as PCR System 9700 (Applied Biosystems), an incubation cycle entailing an incubation at 95° C. for 1 minute and then an incubation at 68° C. for 3 minutes. After the PCR amplification with the cDNAs, the whole amount of resulting PCR mixture is subjected to low melting point agarose gel electrophoresis (Agarose L, Nippon Gene). After confirming the presence of a band therein comprising the normal ERα polynucleotide, the normal ERα polynucleotide is recovered from the low melting point agarose gel.

As the cDNA libraries, there can be utilized a commercially available cDNA library derived from an animal, such as QUICKClone cDNAs (manufactured by Clontech). The cDNA library may then be isolated as described above.

The nucleotide sequence of the recovered normal ERα polynucleotide can be confirmed by preparing a sample of the normal ERα polynucleotide for direct sequencing. Also, DNA fluorescence sequencing techniques may be utilized to sequence the normal ERα polynucleotide. In this regard, to prepare the sample of the normal ERα polynucleotide, there can be utilized commercially available reagents for fluorescence sequencing such as Dye Terminator Sequencing kit FS (Applied Biosystems). The fluorescence sequencing of the normal ERα polynucleotide may be conducted with an autosequencer such as ABI autosequencer (Model 377, Applied Biosystems). Further, the normal ERα polynucleotide may be manually sequenced (Biotechniques, 7, 494 (1989)).

For convenience, the isolated normal ERα polynucleotide can be inserted into a vector capable of replicating in a host such as *E. coli*. For example, about 1 μg of isolated normal ERα polynucleotide may have the ends thereof blunted by a treatment with DNA blunting kit (Takara Shuzo), when the provided isolated normal ERα polynucleotide has uneven ends. A T4 polynucleotide kinase may then be used to phosphorylate the ends of the blunt-ended normal ERα polynucleotide. After phenol treatment, the normal ERα polynucleotide is purified by ethanol precipitation and may be inserted into a vector capable of replication in E. coli. The E. coli vector comprising the normal ERα polynucleotide may be cloned into E. coli host cells.

The E. coli vector comprising the normal ERα polynucleotide may then be isolated from the cloned E. coli cells. The isolated E. coli vector comprising the normal ERα polynucleotide is then used as a template to mutagenize, i.e., introduce nucleotide substitutions, into the normal ERα polynucleotide, such that the resulting mutant ERα polynucleotide contains a variant codon encoding the substituted amino acid at the desired relative position.

The desired nucleotide substitutions may be introduced into the normal ERα polynucleotide according to the site-directed mutagenesis methods described in J. Sambrook, E. F., Frisch, T. Maniatis, "Molecular Cloning 2nd edition", Cold Spring Harbor Laboratory, 1989, or the site directed mutagenesis methods described in McClary J A et al., Biotechniques 1989(3): 282-289. For example, the desired nucleotide substitutions may be introduced into the normal ERα polynucleotide by using a commercially available kit, such as QuickChange Site-Directed Mutagenesis kit manufactured by Stratagene. Typically, such site-directed mutagenesis methods utilize oligonucleotides which introduce the desired nucleotide substitutions therein. In relation to the Quick-Change Site-Directed Mutagenesis kit, the following describes in more detail the site-directed mutagenesis methods utilized with the normal ERα polynucleotide.

The QuickChange Site-Directed Mutagenesis kit utilizes two oligonucleotides to achieve the desired nucleotide substitution into the normal ERα polynucleotide. As such a combination of the two oligonucleotides, there may be utilized for human normal ERα polynucleotide, the combination of oligonucleotides selected from the combination including the oligonucleotide depicted in SEQ ID:13 with the oligonucleotide depicted in SEQ ID:14, the combination including the oligonucleotide depicted in SEQ ID:15 with the oligonucleotide depicted in SEQ ID:16, the combination including the oligonucleotide depicted in SEQ ID:17 with the oligonucleotide depicted in SEQ ID:18, the combination including the oligonucleotide depicted in SEQ ID:19 with the oligonucleotide depicted in SEQ ID:20, the combination including the oligonucleotide depicted in SEQ ID:21 with the oligonucleotide depicted in SEQ ID:22, the combination including the oligonucleotide depicted in SEQ ID:23 with the oligonucleotide depicted in SEQ ID:24, the combination including the oligonucleotide depicted in SEQ ID:25 with the oligonucleotide depicted in SEQ ID:26 or the combination including the oligonucleotide depicted in SEQ ID:27 with the oligonucleotide depicted in SEQ ID:28. Table 2 below shows the relative position of the amino acid encoded at the locus of the nucleotide substitution and the resulting variant codons from utilizing such combinations of the oligonucleotides.

TABLE 2

| SEQ ID of oligo-nucleotides | relative position | nucleotide sequence in encoding normal ERα | variant codon in encoding mutant ERα |
|---|---|---|---|
| 13 & 14 | 303 | AAG (lysine) | AGG (arginine) |
| 15 & 16 | 309 | TCC (serine) | TTC (phenylalanine) |
| 17 & 18 | 390 | GGT (glycine) | GAT (aspartic acid) |
| 19 & 20 | 396 | ATG (methionine) | GTG (valine) |
| 21 & 22 | 415 | GGA (glycine) | GTA (valine) |
| 23 & 24 | 494 | GGC (glycine) | GTC (valine) |
| 25 & 26 | 531 | AAG (lysine) | GAG (glutamic acid) |
| 27 & 28 | 578 | TCC (serine) | CCC (proline) |

The achieved mutant ERα polynucleotide can be sequenced to confirm that the desired nucleotide substitution has been introduced into the normal ERα polynucleotide.

To produce the cell, the mutant ERα gene and the reporter gene are usually introduced into a host cell. The reporter gene is introduced into the host cell so that the reporter gene is inserted into a chromosome of the host cell. The mutant ERα gene is introduced into the host cell for transient expression or is inserted into a chromosome of the host cell. When inserting the mutant ERα gene into a chromosome of the host cell, the mutant ERα gene and reporter gene may be introduced into one chromosome or the mutant ERα gene may be inserted into chromosome other than the chromosome utilized for the reporter gene.

The host cell typically fails have an expressed normal or mutant ERα. Examples of the host cells may include budding yeast cells such as CG1945 (Clontech), animal cells such as HeLa cells, CV-1 cells, Hepa1 cells, NIH3T3 cells, HepG2 cells, COS1 cells, BF-2 cells, CHH-1 cells and insect cells and the like.

The mutant ERα gene and the reporter gene may be inserted into vectors, so that the mutant ERα gene and the reporter gene can be introduced into the host cell. Such vectors typically have a replication origin so that the vector can be replicated in the cell. If so desired, the vector may also have a selective marker gene.

Where the budding yeast cell is used as a host cell, examples of the vector may include plasmid pGBT9, pGAD424, pACT2 (Clontech) and the like. Where mammalian cells are used as host cells, examples of the vector may include plasmids such as pRc/RSV, pRc/CMV (Invitrogen), vectors containing an autonomous replication origin derived from viruses such as bovine papilloma virus plasmid pBPV (Amersham Pharmacia Biotech), EB virus plasmid pCEP4 (Invitrogen) and the like.

When producing a vector encoding the mutant ERα (hereinafter referred to as the mutant ERα vector), it is preferable for the vector to additionally contain the promoter so that the mutant ERα polynucleotide can be inserted into the vector to produce together the mutant ERα gene with the mutant ERα vector. Likewise, when producing a vector encoding the reporter gene (hereinafter referred to as the reporter vector), it is preferable for the vector to contain a TATA sequence or an ERE so that the reporter gene can be produced together with the reporter vector.

When producing the mutant ERα vector together with the mutant ERα gene for an animal host cell, pRc/RSV or pRc/CMV can be utilized. The plasmids pRc/RSV and pRc/CMV contain a promoter which can function in the cell, when derived from an animal host cell, and a cloning cite operably downstream from the promoter. In this regard, the mutant ERα vector can be produced together with the mutant ERα gene by inserting the mutant ERα polynucleotide into pRc/RSV or pRc/CMV at the cloning site. Since pRc/RSV and pRc/CMV also contain an autonomous replication origin of SV40 (ori), pRc/RSV and pRc/CMV may be used to introduce the mutant ERα gene into the animal host cells transformed with ori(−) SV40 genome, if so desired. As such animal host cells transformed with ori(−) SV40 genome, there is mentioned COS cells. When introduced into such animal host cells transformed with ori(−) SV40 genome, the mutant ERα vector produced from pRc/RSV or pRc/CMV can increase to a fairly large copy number therein such that the mutant ERα gene can be expressed in a large amount.

When introducing the mutant ERα vector into a budding yeast host cell, it is preferable to utilize pACT2 to produce the mutant ERα vector. Since pACT2 carries an ADH1 promoter, the mutant ERα gene can be produced together with the mutant ERα vector by inserting the mutant ERα polynucleotide downstream of the ADH1 promoter. In such cases, a the mutant ERα vector can express the mutant ERα gene in a large amount.

Conventional techniques can be used for introducing the mutant ERα gene, according to the type of host cell. For example, the calcium phosphate method, DEAE-dextran method, electroporation, lipofection or the like may be use where mammalian or insect cells are used as host cells. Where yeast cells are used as host cells, there may be used a lithium method such as a method using the Yeast transformation kit (Clontech) or the like.

Furthermore, where the mutant ERα gene is introduced into the host cell as viral DNA, the mutant ERα gene may be introduced into host cells not only by the techniques as described above, but also by infecting the host cells with recombinant virions containing the vital forms of the reporter gene and the mutant ERα gene. For example, viruses such as vaccinia virus may utilized for animal host cells and where insect animal cells are used as host cells, there may be utilized insect viruses such as baculovirus.

When the mutant ERα vector or the reporter vector comprises the selective marker gene, as described above, the selective marker gene may be employed to clone the cell of the present invention. In such cases, the selective marker gene can be utilized to confer a drug resistance to a selective drug exhibiting lethal activity on the cell. The cell in this regard may then be cloned by culturing the cell in a medium supplemented with said selective drug. Exemplary combinations of the selective marker gene and selective drug include a combination of neomycin resistance-conferring selective marker gene and neomycin, a combination of hygromycin resistance-conferring selective marker gene and hygromycin, a combination of blasticidin S resistance-conferring selective marker gene and blasticidin S and the like. In a case wherein the selection marker gene encodes a nutrient which complements the auxotrophic properties of the cell, the cell may be cultured using a minimal medium that substantially contains none of the nutrient. Furthermore, an assay measuring an estrogen binding activity may also used to clone the cell.

In introducing the reporter gene into the host cell, the reporter gene is usually introduced in a linearized form. The linearized reporter gene may allow the reporter gene to be inserted into the chromosome of the host cell. When utilizing the reporter vector, the reporter vector can be linearized by a restriction digestion. The lipofection method may be utilized to introduce the linearized reporter gene into the host cell.

Further, it should be noted that the reporter gene may be introduced into the host cell, before introducing the mutant ERα gene to provide a stably transformed cassette cell. The stably transformed cassette cell stably comprises the reporter gene in a chromosome thereof such that the reporter gene can be genetically handed down to progeny generations. To produce the stably transformed cassette cell, the reporter gene may be introduced into the chromosome of a host cell and the host cell may be cultured for several weeks. After culturing for several weeks, the stably transformed cassette cell can be cloned by employing the selective marker gene, when utilized. For example, the transformed host cells may be continuously cultured for several weeks in a medium supplemented with the selective drug to clone the stable transformed cassette cell. The mutant ERα gene may then be introduced into the stably transformed cassette cell to produce the cell.

Furthermore, the mutant ERα gene may also be introduced into the host cell with the reporter gene so that the host cell is stably transformed with the reporter gene and the mutant ERα gene.

The cell can be utilized to screen for a compound useful for treating a disorder of the mutant ERα. Such a disorder of a mutant ERα may be a disorder which involves an aberrant transactivation by the mutant ERα, such as breast cancer. To screen such a compound, the cell is exposed with an efficient amount of a test compound suspected of being antagonistic or agonistic to the mutant ERα and the transactivation level of the reporter gene is measured.

The cell is typically exposed with a sufficient amount of the test compound for one to several days. The cell can be exposed with the test compound under agonistic conditions or antagonistic conditions directed to the mutant ERα. The agonistic conditions typically have the assay cell exposed to the test compound as the sole agent probable of stimulating the mutant ERα. The antagonistic conditions typically have the assay cell exposed to the test compound and E2.

After exposure, the transactivation level of the reporter gene is measured by measuring the expression level of the reporter gene. In such cases, the reporter protein or the reporter RNA (encoded by the reporter sequence) is stored in the cell or is secreted from the cell so that the expression level can be measured therewith. The expression level of the reporter gene can be measured by a Northern blot analysis, by a Western blot analysis or by measuring the activity level of the reporter protein. The activity level of the reporter protein typically indicates the level at which the reporter gene is expressed.

For example, when the reporter gene encodes luciferase as the reporter protein, the expression level of the reporter gene can be measured by the luminescence provided by reacting luciferin and luciferase. In such cases, a crude cell extract is produced from the cells and luciferin is added to the crude cell extract. The luciferin may be allowed to react with the luciferase in the cell extract at room temperature. The luminescence from adding luciferin is usually measured as an indicator of the expression level or the reporter gene, since the crude cell extract produces a luminescence at a strength proportional to the level of luciferase expressed in the cell and present in the crude cell extract. A luminometer may be utilized to measure the luminescence in the resulting crude cell extract.

The measured transactivation level can then be compared with a control to evaluate the agonistic or antagonistic effect of the test compound. Such a control in screening the test compound can be the expected transactivation level of the reporter gene when the cell is not exposed to the test compound. When the transactivation level of the reporter gene by the mutant ERα is higher than the control under the agonistic conditions, the test compound is evaluated as an agonist directed to the mutant ERα.

Alternatively, when the cell is exposed to E2 and the test compound under the antagonistic conditions, the test compound can be evaluated as an antagonist directed to the mutant ERα. In such cases, the control can be the expected transactivation level of the reporter gene by the mutant ERα in the presence of an equivalent amount of E2. When the transactivation level of the reporter gene by the mutant ERα is lower than the control, the test compound is evaluated as being antagonistic to the mutant ERα.

Such a test compound agonistic or antagonistic to the mutant ERα can then be selected as a compound useful for treating a disorder of the mutant ERα. In such cases, the test compound which provides an transactivation level of the reporter gene which is significantly higher than the control is usually selected when the cell is exposed under the agonistic conditions. The test compound which provides an transactivation level of the reporter gene which is significantly lower than the control is usually selected when the cell is exposed under the antagonistic conditions.

Furthermore, compounds for treating disorders of normal ligand dependent transcription factors can be screened. In such cases, a gene encoding the normal ligand dependent transcription factor, instead of the mutant ERα gene, is introduced into the host cell. Examples of such normal ligand dependent transcription factors include a normal ERβ (Genbank Accession No. AB006590), a normal AR (Genbank Accession No. M23263), a normal GR (Genbank Accession No. M10901), a normal TRα (M24748), a normal PR (Genbank Accession No. 15716), a normal PXR (Genbank Accession No. AF061056), a normal lipophilic vitamin receptor such as a normal VDR (Genbank Accession No. J03258), a normal RAR (Genbank Accession No. 06538), a normal MR (Genbank Accession No. M16801), a normal PPAR γ (Genbank Accession No. U79012) and the like. The reporter gene in such cases comprises an appropriate receptor responsive sequence cognate with the normal ligand dependent transcriptional factor, instead of the ERE.

5.3. The Diagnosis Methods

The diagnosis methods of the present invention involve diagnosing the phenotype of a test ERα or the genotype of a polynucleotide encoding the test ERα. In the genotype diagnosis methods, it can be determined whether the polynucleotide encoding the test ERα contains a valiant codon therein which provides for the one or more substituted amino acids which confer the activity for transactivation of the reporter gene, as described in the above 5.2. In the phenotype diagnosis methods, it can be determined whether the test ERα contains one or more substituted amino acids therein which confer the activity for transactivation of the reporter gene as described in the above 5.2.

The genotype diagnosis methods typically involve preparing the test ERα polynucleotide, searching for the variant codon and determining the mutation in the variant codon, if present. Examples of such genotype diagnosis methods include PCR amplification and nucleotide sequencing methods, single strand conformation polymorphism (SSCP) methods, restriction fragment length polymorphism (RFLP) methods, hybridization methods and the like.

The test ERα polynucleotide can be prepared for the genotype diagnosis methods by preparing test genomic DNAs or test cDNA. In such cases, test genomic DNAs or test cDNAs, which contain the test ERα polynucleotide, are collectively prepared from a test sample obtained from a test animal, such as a test human. Such a test sample may be obtained from non-surgical methods, from surgical methods such as from a fine needle or from a biopsy or the like. Examples of such test samples include the cellular tissue of the test mammal, such as hair, peripheral blood, oral epithelial tissue, liver, prostate, ovaries, uterus, mammary gland or the like, from which test genomic DNAs or test cDNAs can be extracted.

For example, the test genomic DNAs can be prepared according to the methods described in TAKARA PCR Technical news No. 2 (Takara Shuzo, 1991.9). In such cases, a test sample of 2 to 3 hairs from a test mammal are washed with sterile water and ethanol and are cut into 2 to 3 mm in length. The test cells in the hairs are then lysed with a sufficient amount, such as 200 µl, of BCL buffer (10 mM of Tris-HCl (pH 7.5), 5 mM of $MgCl_2$, 0.32 M of sucrose, 1% of Triton X-100). The test genomic DNAs therefrom are washed from unnecessary proteins by adding and mixing Proteinase K and SDS to the lysed test cells to amount to final concentrations of 100 µl/ml and 0.5% (w/v), respectively. After incubating the reaction mixture at 70° C., the test genomic DNAs can be purified by a phenol-chloroform extraction.

Additionally, when the test sample is peripheral blood, test genomic DNAs can be collectively obtained, for example, by processing the test sample with DNA-Extraction kit (Stratagene).

Also, when the test sample is obtained from a biopsy, the test cDNAs may be prepared from the test sample by collectively reverse transcribing the RNAs in the cellular tissue. The RNAs can be collectively obtained from the cellular tissue by using TRIZOL reagent (Gibco), and preferably when the cellular tissue is still fresh.

Furthermore, the test genomic DNAs can be prepared according to the methods described in M. Muramatsu "Labo-Manual-Idenshi-Kogaku" (Maruzen, 1988).

Even furthermore, the test cDNAs may be prepared according to the genetic engineering techniques described in J. Sambrook, E. F. Frisch, T. Maniatis, "Molecular Cloning 2nd edition", Cold Spring Harbor Laboratory, 1989, as described in the above 5.2.

When searching for the variant codon in the genotype diagnosis methods, a searching region in the test ERα polynucleotide typically includes codons therein which are suspected to be the variant codon. As such, the searching region in the test ERα polynucleotide may include the codons in the test ERα polynucleotide which encode the amino acids in the test ERα at relative positions 303 to 578. For example, such genotype diagnosis methods may have the searching region include a codon in the test ERα polynucleotide which encode an amino acid at relative positions selected from 303, 309, 390, 396, 415, 494, 531, 578 and the like.

The PCR amplification and sequencing methods as well as the SSCP methods may then use the prepared test cDNAs or the test genomic DNAs to specifically PCR amplify the searching regions in the test ERα polynucleotide therefrom. Search oligonucleotides can be utilized to specifically PCR amplify from the test cDNAs or test genomic DNAs, the searching regions present in the test ERα polynucleotide.

The search oligonucleotides in this PCR amplification are typically designed to specifically PCR amplify the searching region in the test ERα polynucleotide. The search oligonucleotides may have a size of from 8 to 50 bp, preferably 15 to 40 bp, and may have a GC content of 30% to 70%. Such search oligonucleotides may be synthesized with a DNA synthesizer using the β-cyanoethyl phosphoamidide methods, thiophosphite methods or the like. Further, the search oligonucleotides may be unlabeled, non-radioactively labeled, radiolabeled such as with $^{32}P$ or the like. The PCR amplification typically utilizes a combination of a forward search oligonucleotide and a reverse search oligonucleotide to specifically PCR amplify the searching region in the test ERα polynucleotide. Examples of such combinations of forward and reverse search oligonucleotides for a human test ERα polynucleotide are shown below in Table 3, in connection with the relative position of the amino acid encoded in the searching region.

TABLE 3

SEQ IDs depicting the search oligonucleotides

| Forward search oligonucleotide | Reverse search oligonucleotide | relative position |
|---|---|---|
| SEQ ID: 29, SEQ ID: 30, SEQ ID: 31, SEQ ID: 32 or SEQ ID: 33 | SEQ ID: 34, SEQ ID: 35, SEQ ID: 36, SEQ ID: 37 or SEQ ID: 38 | 303 |
| SEQ ID: 39, SEQ ID: 40, SEQ ID: 41, SEQ ID: 42 or SEQ ID: 43 | SEQ ID: 44, SEQ ID: 45, SEQ ID: 46, SEQ ID: 47 or SEQ ID: 48 | 309 |
| SEQ ID: 49, SEQ ID: 50, SEQ ID: 51, SEQ ID: 52 or SEQ ID: 53 | SEQ ID: 54, SEQ ID: 55, SEQ ID: 56, SEQ ID: 57 or SEQ ID: 58 | 390 |
| SEQ ID: 59, SEQ ID: 60, SEQ ID: 61, SEQ ID: 62 or SEQ ID: 63 | SEQ ID: 64, SEQ ID: 65, SEQ ID: 66, SEQ ID: 67 or SEQ ID: 68 | 396 |
| SEQ ID: 69, SEQ ID: 70, SEQ ID: 71, SEQ ID: 72 or SEQ ID: 73 | SEQ ID: 74, SEQ ID: 75, SEQ ID: 76, SEQ ID: 77 or SEQ ID: 78 | 415 |
| SEQ ID: 79, SEQ ID: 80, SEQ ID: 81, SEQ ID: 82 or SEQ ID: 83 | SEQ ID: 84, SEQ ID: 85, SEQ ID: 86, SEQ ID: 87 or SEQ ID: 88 | 494 |
| SEQ ID: 89, SEQ ID: 90, SEQ ID: 91, SEQ ID: 92 or SEQ ID: 93 | SEQ ID: 94, SEQ ID: 95, SEQ ID: 96, SEQ ID: 97 or SEQ ID: 98 | 531 |
| SEQ ID: 99, SEQ ID: 100, SEQ ID: 101, SEQ ID: 102 or SEQ ID: 103 | SEQ ID: 104, SEQ ID: 105, SEQ ID: 106, SEQ ID: 107 or SEQ ID: 108 | 578 |

The searching regions in the test ERα polynucleotide can be specifically PCR amplified from the test cDNAs or the test genomic DNAs according to the methods described in Saiki et al., Science, vol. 230, pp. 1350-1354 (1985). The PCR mixture in this PCR amplification may contain 1.5 mM to 3.0 mM magnesium chloride, heat tolerant DNA polymerase, dNTPs (dATP, dTTP, dGTP, and dCTP), one of the forward search oligonucleotides in combination with one of the reverse search oligonucleotides and the test genomic DNAs or test cDNAs. In this PCR amplification, there may be repeated 20 to 50 times, preferably 25 to 40 times, an incubation cycle entailing a denaturation incubation, an annealing incubation and an elongation incubation. The denaturation incubation may incubate the PCR mixture at 90° C. to 95° C., and preferably at 94° C. to 95° C., for 1 min to 5 min, and preferably for 1 min to 2 min. The annealing incubation following the denaturing incubation may incubate the PCR mixture at 30° C. to 70° C., and preferably at 40° C. to 60° C., for 3 seconds to 3 minutes, and preferably for 5 seconds to 2 minutes. The elongation incubation following the denaturing incubation may incubate the PCR mixture at 70° C. to 75° C., and preferably at 72° C. to 73° C., for about 15 seconds to 5 minutes, and preferably for 30 seconds to 4 minutes.

When utilizing the PCR amplification and nucleotide sequencing methods, the genotype diagnosis methods may then entail subjecting the resulting PCR mixture to low melting point agarose gel electrophoresis. The amplified polynucleotide encoding the searching region (hereinafter referred to as searching region polynucleotide) is recovered from the low melting point agarose gel and is sequenced to provide a nucleotide sequence of the searching region polynucleotide.

The mutation in the variant codon, if present, may then be determined by sequencing the searching region polynucleotide and by determining the mutation in the nucleotide sequence. In sequencing the searching region polynucleotide, there may be utilized the direct sequencing methods or an automated sequencing method. Examples of the direct sequencing methods include manual sequencing methods (Maxam Gilbert method described in Maxam, A. M. & W. Gilbert, Proc. Natl. Acad. Sci. USA, 74, 560, 1977), the Sanger method (described in Sanger, F. & A. R. Coulson, J. Mol. Biol., 94, 441, 1975 as well as Sanger, F., Nicklen, and A. R., Coulson, Proc. Natl. Acad. Sci. USA., 74, 5463, 1977), the methods described in BioTechniques, 7, 494 (1989) and the like. When an automated DNA sequencer such as ABI autosequencer (Model 377. Applied Biosystems) is used, an appropriate DNA sequencing kit such as ABI Big Dye terminator cycle sequencing ready reaction kit can be used to prepared the searching region for the automated DNA sequencer. After sequencing, the nucleotide sequence of the searching region polynucleotide may then be compared to a nucleotide sequence encoding a normal ERα to determine the mutation in the valiant codon, if present, in the searching region.

When utilizing the SSCP methods, the resulting PCR mixture is subjected to a native polyacrylamide gel electrophoresis according to the methods described in Hum. Mutation, vol. 2, p. 338. In such cases, it is preferable that the PCR amplification above utilize the radiolabeled oligonucleotides so that the searching region polynucleotide is radiolabeled and the searching region polynucleotide can be detected in the native polyacrylamide gel by employing the radioactivity thereof. In such SSCP methods, the radiolabeled searching region polynucleotide can be heat-denatured into single strand polynucleotides and subjected to the native polyacrylamide gel electrophoresis in a buffer to separate each of the single strand polynucleotides. Examples of buffers which may be utilized in the native polyacrylamide gel electrophoresis include Tris-phosphate (pH 7.5-8.0), Tris-acetate (pH 7.5-8.0), Tris-borate (pH 7.5-8.3) and the like, with Tris-borate (pH 7.5-8.3) being preferred. In addition, auxiliary components for the native polyacrylamide gel electrophoresis may be utilized in the buffer, such as EDTA. The conditions for such native polyacrylamide gel electrophoresis may include a constant power of 30 to 40 W at 4° C. to room temperature (about 20 to 25° C.) for 1 hour to 4 hours.

After the native polyacrylamide gel electrophoresis, the native polyacrylamide gel is transferred onto a filter paper and contacted with X-ray film to expose the X-ray film with the radiation from the radiolabeled searching region polynucleotide. An appropriate cassette may be utilized to expose the X-ray film. The autoradiogram obtained from developing the X-ray film allows a comparison of the mobility of the radiolabeled searching region polynucleotide with the mobility of a standard. Such a mobility of the standard can be the mobility expected when the searching region polynucleotide is composed of only normal codons of the normal ERα polynucleotide. A mobility of the radiolabeled searching region polynucleotide different from the mobility of the standard typically indicates that there is one or more valiant codons in the radiolabeled searching region.

The radiolabeled searching region polynucleotide may then be recovered from the native polyacrylamide gel by using heated or boiling water. The radiolabeled searching region may be PCR amplified for a second round and then prepared for sequencing. The mutation in the variant codon, if present, may then be determined similarly to the methods described above in the PCR amplification and nucleotide sequencing methods.

The hybridization methods typically utilize a probe oligonucleotide to observe whether the probe oligonucleotide can hybridize to the searching regions. The searching regions can be provided in the hybridization methods by utilizing the searching region polynucleotide, the prepared test cDNA, the prepared test genomic DNA, a purified test ERα polynucleotide or the like. Further, the hybridization methods may restriction digest the searching region polynucleotide and then utilize the restriction digested searching region polynucleotide to observe whether the probe oligonucleotide can hybridize thereto.

The probe oligonucleotides may have a size of from 15 to 40 bp, and may have a GC content of 30% to 70%. Such probe oligonucleotides may be synthesized with a DNA synthesizer using the β-cyanoethyl phosphoamidide methods, thiophosphite methods or the like. Further, the probe oligonucleotides are typically non-radioactively labeled such as with biotin, radiolabeled such as with $^{32}P$ or the like.

The probe oligonucleotides may be composed of the nucleotide sequence of the searching region, when the searching region is composed of only normal codons of a normal ERα polynucleotide. Such a nucleotide sequence allows the probe oligonucleotides to hybridize to the searching region in the test ERα polynucleotide under stringent conditions, when the searching region therein is composed of only normal codons of a normal ERα polynucleotide. Examples of such probe oligonucleotides for a human test ERα polynucleotide are shown below in Table 3, in connection with the relative position of the amino acid encoded in the searching region.

TABLE 3

| Probe oligonucleotide | relative position |
|---|---|
| SEQ ID: 111, SEQ ID: 112, SEQ ID: 113, SEQ ID: 114 or SEQ ID: 115 | 303 |
| SEQ ID: 116, SEQ ID: 117, SEQ ID: 118, SEQ ID: 119 or SEQ ID: 120 | 309 |
| SEQ ID: 121, SEQ ID: 122, SEQ ID: 123, SEQ ID: 124 or SEQ ID: 125 | 390 |
| SEQ ID: 126, SEQ ID: 127, SEQ ID: 128, SEQ ID: 129 or SEQ ID: 130 | 396 |
| SEQ ID: 131, SEQ ID: 132, SEQ ID: 133, SEQ ID: 134 or SEQ ID: 135 | 415 |
| SEQ ID: 136, SEQ ID: 137, SEQ ID: 138, SEQ ID: 139 or SEQ ID: 140 | 494 |
| SEQ ID: 141, SEQ ID: 142, SEQ ID: 143, SEQ ID: 144 or SEQ ID: 145 | 531 |
| SEQ ID: 146, SEQ ID: 147, SEQ ID: 148, SEQ ID: 149 or SEQ ID: 150 | 578 |

Typically, the hybridization methods are conducted under stringent conditions. As such stringent conditions, for example, the prehybridization or hybridization treatments are conducted in prehybridization buffer and hybridization buffer, and the washings are conducted twice for 15 minutes in washing buffer. The hybridization methods may optionally have another washing for 30 minutes in a buffer containing 0.1×SSC (0.015M NaCl, 0.0015M sodium citrate) and 0.5% SDS. As the prehybridization buffer, there may be utilized a buffer containing 6×SSC (0.9M NaCl, 0.09M sodium citrate), 5×Denhart (0.1% (w/v) phycol 400, 0.1% (w/v) polypyrolidone and 0.1% BSA), 0.5% (w/v) SDS and 100 µg/ml of salmon sperm DNA. Also as the prehybridization buffer, there may be utilized a DIG EASY Hyb buffer (Boehringer Manheim) to which salmon sperm DNA is added to a concentration of 100 µg/ml. Further, as the prehybridization buffer, there may be utilized a buffer containing 6×SSPE (0.9M NaCl, 0.052M $NaH_2PO_4$, 7.5 mM EDTA), 0.5% SDS, 5×Denhart and 0.1 mg/ml of salmon sperm DNA. As the hybridization buffer, there may be utilized the prehybridization buffer to which the probe oligonucleotide is added to a sufficient amount. The temperature of the prehybridization and hybridization treatments can vary with the length of the probe oligonucleotide and for example, may be at the Tm value of the probe oligonucleotide to a temperature that is 2 to 3 lower than the Tm value of the probe oligonucleotide. The temperature of the washings can also vary with the length of the oligonucleotide, and for example may be conducted at room temperature. The Tm value in such cases, can be achieved by estimating the quantity of nucleotide units that should form hydrogen bonds in the hybridization buffer with the nucleotide units in the probe oligonucleotide, and then by adding the temperatures achieved from adding 2° C. for the A or T nucleotide units in the probe oligonucleotide which should form the hydrogen bond and adding 4° C. for the G or T nucleotide units in the probe oligonucleotide which should form the hydrogen bond.

For example, the hybridization methods can involve dot-blot hybridization methods, mismatch detection methods or the like.

The dot-blot hybridization methods typically involve fixing the test ERα polynucleotide to a membrane and evaluating whether the probe oligonucleotide can hybridize to the searching region in the fixed test ERα polynucleotide. In fixing test ERα polynucleotide onto the membrane, there can be utilized as the test ERα polynucleotide, the searching region polynucleotide, the prepared test cDNA, the prepared test genomic DNA, a purified test ERα polynucleotide or the like. The test ERα polynucleotide can be fixed to the membrane by incubating the test ERα polynucleotide at 90 to 100° C. for 3 to 5 min, by spotting the test ERα polynucleotide onto the membrane, by drying the resulting membrane and by exposing the spotted searching region with UV light. As the membrane, there can be utilized a nylon membrane such as Hybond N (Amerscham Pharmacia). The probe oligonucleotide can then be utilized to, evaluate whether the probe oligonucleotide can hybridize to the searching region. The probe oligonucleotide may be utilized by incubating the probe oligonucleotide and the test ERα polynucleotide at 40 to 50° C. for 10 to 20 hours. The resulting membrane may then be washed and the hybridized probe oligonucleotide can then be detected, if present.

When the probe oligonucleotide is radiolabeled with $^{32}P$, the hybridized probe oligonucleotide, if present, may be detected by exposing the resulting membrane to a X-ray film.

When the probe oligonucleotide is nonradioactively labeled with biotin, the hybridized probe oligonucleotide, if present, may be detected with a spacer and a hybridization detection enzyme such as biotinylated alkaline phosphatase, biotinylated peroxidase or the like. When the probe oligonucleotide labeled with biotin can hybridize to the searching region, the spacer, such as streptavidin, can bind to the hybridized probe oligonucleotide labeled with biotin such that the hybridization detection enzyme can then connect to the hybridized probe oligonucleotide labeled with biotin through the spacer. The connected hybridization detection enzyme can then participate in a reaction to indicate whether the probe oligonucleotide has hybridized to the searching region in the test ERα polynucleotide. The enzymatic reaction can provide a change in color or a luminescence.

When the probe oligonucleotide does not hybridize to the searching region, it can be determined that the searching region contains one or more of the variant codons. The searching region may then be sequenced. The mutation in the variant codon, if present, may be determined similarly to the methods described above in the PCR amplification and nucleotide sequencing methods.

The mismatch detection methods are described in Biswas, I. and Hsieh, P., J. Biol. Chem., 271(9), pp. 5040-5048 (1996) as well as Nippon gene information, 1999, No. 125, Nippon Gene, Toyama. In such mismatch detection methods, a mismatch detection enzyme, such as Taq Mut S, is utilized to search certain mismatches in the hybridization of the probe oligonucleotide to the searching region. The mismatch detection enzyme allows the mismatches in the hybridization of the probe oligonucleotide with the searching region to be detected at high temperatures such as at a temperature of 75° C. or lower. Typically, such mismatches in the hybridization thereof, bound with the mismatch detection enzyme, can be detected by a gel shift assay or by the dot blot hybridization methods as described in the above. When the mismatch detection enzyme can bind to a mismatched hybridization of the probe oligonucleotide and the searching region, it may be determined that the searching region contains one or more of the valiant codons. The searching region may be sequenced. The mutation in the variant codon, if present, may then be determined similarly to the methods described above in the PCR amplification and nucleotide sequencing methods.

Further, in the RFLP methods, a restriction enzyme is mixed with the test ERα polynucleotide under reacting conditions. Typically, the restriction enzyme has a restriction site overlapping with the codon in the searching region, which is suspected to be the variant codon. A successful or an unsuccessful restriction digest at the restriction site can determine whether there is the variant codon in the searching region. The results of the restriction digestion can be evaluated by gel electrophoresis analysis, such as with low melting point agarose gel electrophoresis. The searching region may then be sequenced, if needed. The mutation in the variant codon, if present, may then be determined similarly to the methods described above in the PCR amplification and nucleotide sequencing methods.

The phenotype diagnosis methods may involve searching in an amino acid sequence of the test ERα for one or more substituted amino acids which confer the activity for transactivation of the reporter gene as described in the above 5.2. After searching for the substituted amino acid, the mutation in the test ERα, if present, is determined by comparing the amino acid sequence of the test ERα to the amino acid sequence of the normal ERα. To search for the substituted amino acid in the test ERα, the searching region in the test ERα may include the amino acids in the test ERα at relative positions 303 to 578. For example, such phenotype diagnosis methods may have the searching region include an amino acid in the test ERα at one or more relative positions selected from 303, 309, 390, 396, 415, 494, 531, 578 and the like.

To search for the substituted amino acid in the test ERα, an antibody having an epitope in the searching region in the test ERα may be useful. A successful or unsuccessful binding of such an antibody can determine whether there is a substituted amino acid at the searching region in the test ERα. The mutation in the test ERα can then be determined by comparing the amino acid sequence of the test ERα with the amino acid sequence of a normal ERα.

The test ERα may be prepared from a test sample by cell extract techniques. Further, the test ERα may be prepared for the phenotype diagnosis methods by purifying recombinant test ERα.

5.4. The Reporter Assay with the Test ERα

A test ERα can be assayed for the activity for transactivation of the reporter gene, described in the above 5.2., by utilizing an assay cell comprising the test ERα and a chromosome which comprises the reporter gene. In such cases, the assay cell is typically exposed to a ligand and the transactivation level of the reporter gene is measured to quantitatively analyze the activity for transactivation of the reporter gene by the test ERα. Further, the activity for transactivation of the reporter gene by the test ERα can be evaluated by comparing the transactivation level of the reporter gene by the test ERα to the transactivation level of the reporter gene by a standard. Furthermore, the test ERα can be screened by selecting the test ERα in which the transactivation level of the reporter gene by the test ERα is different than the transactivation level by the standard.

The assay cell can be produced by introducing the reporter gene and a gene encoding the test ERα into a host cell. The reporter gene is inserted into a chromosome of the host cell. The test ERα gene can be introduced into the host cell for transient expression or can be introduced into the host cell so that the test ERα gene is inserted into a chromosome of the host cell. When inserting the test ERα gene into a chromosome of the host cell, the test ERα gene may be inserted into the chromosome together with the test ERα or into another chromosome in the host cell. Additionally, the reporter gene may be introduced into the host cell to produce a stably transformed cassette cell, as described in the above 5.2., and the test ERα gene may then be introduced into the stably transformed cassette cell, as described in the above 5.2.

The test ERα gene is introduced into the host cell so that the test ERα gene can be expressed in the assay cell to provide the test ERα. In this regard, such a test ERα gene typically comprises a promoter linked operably upstream from a polynucleotide which encodes the test ERα.

To introduce the test ERα gene into the host cell, conventional techniques for introducing the test ERα gene may be applied according to the type of host cell, as described in the above 5.2. In this regard, when test ERα is introduced into the host cell for transient expression, the test ERα gene is introduced in a circular form. When inserting the test ERα gene into the chromosome of the host cell, the test ERα is introduced in a linearized form. Also, a vector may be utilized to introduce the test ERα gene or the reporter gene into the host cell, as described in the above 5.2.

Further, the test ERα gene can be introduced into the stably transformed cassette cell to provide the assay cell. In such cases, the test ERα gene may also be introduced into the stably transformed cassette cell to provide a stably transformed binary cell. Such an stably transformed binary cell has the chromosomes thereof stably comprise the test ERα gene and the reporter gene.

The host cell utilized to produce the assay cell typically fails have an expressed normal or mutant ERα. Examples of the host cells include eukaryotic cells such as HeLa cells, CV-1 cells, Hepa1 cells, NIH3T3 cells, HepG2 cells, COS1 cells, BF-2 cells, CHH-1 cells and the like.

In the reporter assay, the assay cell is typically exposed with a sufficient amount of a ligand for one to several days. Further, the ligand can be exposed to the assay cell under agonistic conditions or antagonistic conditions directed to the test ERα. The agonistic conditions typically have the assay cell exposed to the ligand as the sole agent probable of stimulating the test ERα. The antagonistic conditions typically have the assay cell exposed to the ligand and E2.

As the ligand there is usually utilized a ligand that is purely or partially antagonistic or agonistic to the normal ERα. Examples of such ligands include the partial anti-estrogens such as tamoxifen, 4-hydroxytamoxifen and raloxifene, the pure anti-estrogens such as ICI 182780 (Wakeling A E et al., Cancer Res., 512:3867-3873 (1991)) and ZM 189154 (Dukes M et al., J. Endocrinol., 141:335-341 (1994)) and the like.

After exposure, the transactivation level of the reporter gene is measured by measuring the expression level of the reporter gene. In such cases, the reporter protein or the reporter RNA (encoded by the reporter sequence) is stored in the cell or is secreted from the cell so that the expression level can be measured therewith. The expression level of the reporter gene can be measured by a Northern blot analysis, by a Western blot analysis or by measuring the activity level of the reporter protein. The activity level of the protein typically indicates the level at which the reporter protein is expressed.

For example, when the reporter gene encodes luciferase as the reporter protein, the expression level of the reporter gene can be measured by the luminescence provided by reacting luciferin and luciferase. In such cases, a crude cell extract is produced from the cells and luciferin is added to the crude cell extract. The luciferin may be allowed to react with the luciferase in the cell extract at room temperature. The luminescence from adding luciferin is usually measured as an indicator of the expression level of the reporter gene, since the crude cell extract produces a luminescence at a strength proportional to the level of luciferase expressed in the cell and present in the crude cell extract. A luminometer may be utilized to measure the luminescence in the resulting crude cell extract.

The measured transactivation level can then be compared with a transactivation level of the reporter gene by a standard to evaluate the activity for transactivation by the test ERα. Such a transactivation level of the reporter gene by the standard in evaluating the activity for transactivation by the test ERα can be the expected transactivation level of the reporter gene in cases in which the assay cell expresses the normal ERα or an ERα which phenotype is known (instead of the test ERα). When the measured transactivation level provided by the test ERα is different than the transactivation level of the reporter gene by the standard, the test ERα may be selected as a mutant ERα.

Furthermore, mutant ligand dependent transcription factors can be screened. In such cases, the a gene encoding the test ligand dependent transcription factor, instead of the test ERα gene, in introduced into the host cell. Examples of such test ligand dependent transcription factors include a test ERβ, a test AR, a test GR, a test TR, a test PR, a test PXR, a test lipophilic vitamin receptor such a test VDR and a test RAR and the like. The reporter gene in such cases comprises an appropriate receptor responsive sequence cognate with the provided test ligand dependent transcriptional factor, instead of the ERE.

6. EXAMPLES

6.1. Example 1 A Polynucleotide Encoding the Human Mutant ERα

6.1.1. Production of a Plasmid Encoding Human Normal ERα

A human liver cDNA library (CLONETECH, Quick clone cDNA#7113-1) is utilized to specifically PCR amplify therefrom a cDNA encoding a human normal ERα. The PCR mixture in this PCR amplification contains 10 ng of the human liver cDNA library, 10 pmol of an oligonucleotide depicted in SEQ ID:11, 10 pmol of a oligonucleotide depicted in SEQ ID:12, LA-Taq Polymerase (Takara Shuzo), the buffer provided with the LA-Taq Polymerase and dNTPs (dATP, dTTP, dGTP, dCTP). The oligonucleotides depicted in SEQ ID:11 and SEQ ID:12 are synthesized with a DNA synthesizer (Model 394, Applied Biosystems). In this PCR amplification, there is repeated 35 times with a PCRsystem 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm that the amplified cDNA from the PCR amplification has a size of about 1.8 kb. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems), to reveal that the cDNA has a nucleotide sequence encoding a human normal ERα which has the amino acid sequence shown in SEQ ID:1.

Another PCR amplification is then similarly conducted to add a Kozak consensus sequence immediately upstream from the start codon (ATG) in the cDNA. In this PCR amplification, there is utilized 100 ng of the cDNA, a oligonucleotide depicted in SEQ ID:151 and an oligonucleotide depicted in SEQ ID:12. The resulting PCR mixture is subjected to low melting point agarose gel electrophoresis (Agarose L: Nippon Gene) to confirm that the amplified cDNA from the PCR amplification has a size of about 1.8 kb. After recovering the amplified cDNA from the low melting point agarose gel, 1 µg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends thereof. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with bacterial alkaline phosphatase (BAP) for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform E. coli competent DH5α cells (TOYOBO). The transformed E. coli cells are cultured in LB (Luria-Bertani) medium to which ampicillin is added to a concentration of 50 µg/ml (hereinafter referred to as LB-amp medium; J. Sambrook, E. F. Frisch, T. Maniatis; Molecular Cloning 2nd Edition, Cold Springs Harbor Laboratory Publishing, 1989). The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The prepared plasmids are sequenced with an ABI autosequencer (Model 377, Applied Biosystems), to confirm that there is a plasmid that has a nucleotide sequence encoding human normal ERα having the amino acid sequence shown in SEQ ID:1. Such a plasmid is selected and is designated as pRc/RSV-hERα-Kozak.

6.1.2. Production of Plasmids Encoding the Human Mutant ERα K303R, S309F, M396V, G415V, G494V or K531E 6.1.2.1. Production of a Plasmid for Mutagenesis The plasmid pRc/RSV-hERαKozak is restriction digested with restriction enzyme Not I for 1 hour at 37° C. The restriction digestion reaction mixture is subjected to low melting point agarose gel electrophoresis (Agarose L: Nippon Gene) to confirm that there is DNA fragment having a size of about 1.6 kb. The 1.6 kb DNA fragment is then recovered from the low melting point agarose gel.

The plasmid pBluescriptII SK(+) (Stratagene) is restriction digested with NotI for 1 hour at 37° C. and is then treated with BAP for 1 hour at 65° C. The restriction digestion reaction mixture is subjected to low melting point agarose gel electrophoresis (Agarose L: Nippon Gene) and the restriction digested pBluescriptII SK(+) is recovered from the low melting point agarose gel. Subsequently, 100 ng of the above 1.6 kb DNA, fragment and 100 ng of the recovered pBluescriptII SK(+) are used in a ligation reaction with T4 DNA ligase. The ligation reaction mixture is used to transform E. coli competent DH5α cells (TOYOBO). The transformed E. coli cells are cultured in LB-amp medium. The clones thereof showing an ampicillin resistance are then recovered. Some of the clones are then used to isolate therefrom the plasmids derived from the ligation reaction. An aliquot sample of each of the isolated plasmids are then restriction digested with restriction enzymes Not I and Hind III. The restriction digestion reaction mixtures are subjected to agarose gel electrophoresis. It is then confirmed that there is plasmid in which the plus strand in the plasmid contains the sense strand encoding the human normal ERα operably with M13 microphage replication origin (fl ori). In this regard, it is confirmed that there is a plasmid which has a structure such that when the fl ori replicates one of the strands in the plasmid, the sense strand encoding human normal ERα would be replicated therewith. Such a plasmid is selected and is designated as pSK-NN.

6.1.2.2. Site Directed Mutagenesis at Relative Positions 303, 309, 396, 415, 494 and 531

According to the methods described in McClary J A et al. (Biotechniques 1989(3): 282-289), specified mutations are introduced into the polynucleotide encoding the human normal ERα. Such procedures are described in relation with the present invention below.

The plasmid pSK-NN, provided in the above 6.1.2.1., is utilized to transform E. coli competent CJ236 cells (Takara Shuzo) according to the protocol provided with the E. coli competent CJ236 cells. A clone thereof showing ampicillin resistance is then cultured for 16 hours in a LB-amp medium. Subsequently, a colony of the clone is suspended in 10 ml of a 2×YT medium to which a M13 helper phage is added to a concentration of at least 1×10$^{11}$ pfu/ml (hereinafter referred to as 2×YT-M13) medium. After culturing the clone in the 2×YT-M13 medium for 2 hours at 37° C., kanamycin is added thereto to a concentration of 50 μg/ml and the clone is then cultured for 22 hours. The resulting suspension is centrifuged and 8 ml of the resulting supernatant is transferred to a 15 ml test tube. Two milliliters (2 ml) of 2.5M NaCl-40% PEG8000 (Sigma) is then added to and stirred with the supernatant. The supernatant is refrigerated at 4° C. for 1 hour and is centrifuged (3,000 rpm, 2,000×g, 10 minutes, 4° C.) to collect the phage therefrom as a pellet. After the phage is suspended in 400 μl of distilled water, an identical amount by volume of phenol is added thereto and the resulting suspension is gently shook for 5 minutes. The resulting suspension is centrifuged so that the aqueous layer therein is extracted therefrom. For a second round of phenol treatment, an identical amount by volume of phenol is then added to the aqueous layer and is vigorously shook. The resulting suspension is centrifuged so that the aqueous layer is extracted therefrom. To the aqueous layer from the second phenol treatment, an identical amount by volume of chloroform is added thereto and is vigorously shook. The resulting suspension is centrifuged (15,000 rpm, 20,000×g, 5 minutes, 4° C.) to extract the aqueous layer therefrom. To the aqueous layer from the chloroform treatment, there is added 800 μl of 100% ethanol and 50 μl of 3M sodium acetate. After refrigerating the aqueous layer therefrom at −80° C. for 20 minutes, the aqueous layer is centrifuged. The resulting pellet therefrom is rinsed with 70% ethanol and is then dried. After pellet the residue in sterile water, the light absorbance of aqueous solution is measured at a wavelength of 260 nm to calculate the amount of the single strand sense DNA encoding human normal ERα therein.

The oligonucleotides for the site directed mutagenesis are synthesized to provide the oligonucleotides depicted in SEQ ID:152, SEQ ID:153, SEQ ID:154, SEQ ID:155, SEQ ID:156 and SEQ ID:157.

In using the oligonucleotide depicted in SEQ ID:152, the AAG codon encoding the lysine present at relative position 303 is changed to an AGG codon encoding arginine.

In using the oligonucleotide depicted in SEQ ID:153, the TCC codon encoding the serine present at relative position 309 is changed to a TTC codon encoding phenylalanine.

In using the oligonucleotide depicted in SEQ ID:154, the ATG codon encoding the methionine present at relative position 396 is changed to an GTG codon encoding valine.

In using the oligonucleotide depicted in SEQ ID:155, the GGA codon encoding the glycine present at relative position 415 is changed to a GTA codon encoding valine.

In using the oligonucleotide depicted in SEQ ID:156, the GGC codon encoding the glycine present at relative position 494 is changed to a GTC codon encoding valine.

In using the oligonucleotide depicted in SEQ ID:157, the AAG codon encoding the lysine present at relative position 531 is changed to a GAG codon encoding glutamic acid.

Each of the oligonucleotides is phosphorylated with 10 pmol of a polynucleotide kinase (Takara Shuzo) in the buffer provided with the polynucleotide kinase. In the phosphorylation reactions, 2 mM of ATP is used in each of the reaction mixtures and the reaction mixtures are incubated at 37° C. for 30 minutes. Subsequently, about 1 pmol of the phosphorylated oligonucleotides are mixed, respectively, with 0.2 pmol of the single stand sense DNA encoding normal ERα. To produce 10 μl annealing reaction mixtures, the mixtures are then added, respectively, to annealing buffer (20 mM of Tris-Cl (pH7.4), 2 mM of MgCl$_2$, 50 mM of NaCl). The annealing reaction mixtures are subjected to an incubation at 70° C. for 10 minutes, then an incubation at 37° C. for 60 minutes, which is followed by an incubation at 4° C. Synthesizing reaction mixtures are then produced therefrom by adding, respectively, to the annealing reaction mixtures, 2 units (0.25 μl) of T7 DNA polymerase (New England Labs), 2 units of (0.25 μl) of T4 DNA ligase (Takara Shuzo) and 1.2 μl of a synthesizing buffer (175 mM of (Tris-Cl (pH 7.4), 375 mM of MgCl$_2$, 5 mM of DTT, 4 mM of dATP, 4 mM of dCTP, 4 mM of dGTP, 4 mM of dTTP and 7.5 mM of ATP). The synthesizing reaction mixtures are incubated at 4° C. for 5 minutes, incubated at room temperature for 5 minutes, and then incubated at 37° C. for 2 hours, to provide synthesized DNA plasmids.

Two microliters (2 μl) of each of the synthesizing reaction mixtures are then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids from the synthesizing reactions. An aliquot sample of each of the isolated plasmids are then prepared with a Dye Terminator Sequence Kit FS (Applied Biosystems). The isolated plasmids are sequenced with an ABI autosequencer (Model 377, Applied Biosystems).

It is confirmed from the sequencing that the isolated plasmids synthesized from utilizing the oligonucleotide depicted in SEQ ID:152 provides an isolated plasmid which has in the nucleotide sequence encoding the human mutant ERα, an AGG codon corresponding to relative position 303, to provide arginine. Such an isolated plasmid is selected and is designated as pSK-NN303.

It is confirmed from the sequencing that the isolated plasmids synthesized from the oligonucleotide depicted in SEQ ID:153 provides an isolated plasmid which has in the nucleotide sequence encoding the human mutant ERα, a TTC codon corresponding to relative position 309, to provide phenylalanine. Such an isolated plasmid is selected and is designated as pSK-NN309.

It is confirmed from the sequencing that the isolated plasmids synthesized from the oligonucleotide depicted in SEQ ID:154 provides an isolated plasmid which has in the nucleotide sequence encoding the human mutant ERα, a GTG codon corresponding to relative position 396, to provide valine. Such an isolated plasmid is selected and is designated as pSK-NN396.

It is confirmed from the sequencing that the isolated plasmids synthesized from the oligonucleotide depicted in SEQ ID:155 provides an isolated plasmid which has in the nucleotide sequence encoding the human mutant ERα, a GTA codon corresponding to relative position 415, to provide valine. Such an isolated plasmid is selected and is designated as pSK-NN415.

It is confirmed from the sequencing that the isolated plasmids synthesized from the oligonucleotide depicted in SEQ ID:156 provides an isolated plasmid which has in the nucleotide sequence encoding the human mutant ERα, a GTC codon corresponding to relative position 494, to provide valine. Such an isolated plasmid is selected and is designated as pSK-NN494.

It is confirmed from the sequencing that the isolated plasmids synthesized from the oligonucleotide depicted in SEQ ID:157 provides an isolated plasmid which has in the nucleotide sequence encoding the human mutant ERα, a GAG codon corresponding to relative position 531, to provide glutamic acid. Such as isolated plasmid is selected and is designated as pSK-NN531.

Table 4 below shows the utilized oligonucleotide for the mutagenesis, the produced plasmid therefrom and the resulting human mutant ERα therefrom.

TABLE 1

| SEQ ID of utilized oligonucleotide | produced plasmid | human mutant ERα |
|---|---|---|
| SEQ ID: 152 | pSK-NN303 | human mutant ERαK303R |
| SEQ ID: 153 | pSK-NN309 | human mutant ERαS309F |
| SEQ ID: 154 | pSK-NN396 | human mutant ERαM396V |
| SEQ ID: 155 | pSK-NN415 | human mutant ERαG415V |
| SEQ ID: 156 | pSK-NN494 | human mutant ERαG494V |
| SEQ ID: 157 | pSK-NN531 | human mutant ERαK531E |

The plasmids pSK-NN303, pSK-NN309, pSK-NN396, pSK-NN415, pSK-NN494 and pSK-NN531 are each restriction digested with restriction enzyme Not I at 37° C. for 1 hour. Each of the restriction digestion reaction mixtures are then subjected to low melting point agarose gel electrophoresis to confirm that there are DNA fragments having a size of about 1.6 kb. The 1.6 kb DNA fragments are then recovered from the low melting point agarose gel.

The plasmid pRc/RSV-hERαKozak, provided in 6.1.1., is restriction digested with restriction enzyme Not I at 37° C. for 1 hour and is treated with BAP at 65° C. for 1 hour. The restriction digestion reaction mixture is then subjected to low melting point agarose gel electrophoresis to confirm that there is a DNA fragment having a size of about 5.5 kb. The 5.5 kb DNA fragment is then recovered from the low melting point agarose gel.

Subsequently, 100 ng of the recovered 5.5 kb DNA fragments are mixed, respectively, with 100 ng of the above 1.6 kb DNA fragments for a ligation reaction with T4 DNA ligase. The ligation reaction mixtures are used to transform E. coli competent DH5α cells (TOYOBO). The transformed E. coli cells are cultured in LB-amp medium. The clones thereof showing an ampicillin resistance are then recovered. Some of the clones are then used to isolate therefrom the plasmids derived from the ligation reactions. An aliquot sample of each of the isolated plasmids are then restriction digested with either restriction enzyme Not I or Mlu I. The restriction digestion reaction mixtures are then subjected to agarose gel electrophoresis. It is confirmed that there are isolated plasmids which result from the each of the restriction digestions, DNA fragments having the desired sizes. Such isolated plasmids provide DNA fragments having sizes of 5.5 and 1.6 kb in the restriction digestions with restriction enzyme Not I and provide DNA fragments of 7.1 kb in restriction digestions with restriction enzyme Mlu I.

Each of the plasmids above is then PCR amplified with oligonucleotides depicted in SEQ ID:158, SEQ ID:159 and SEQ ID:160. The PCR mixtures in these PCR amplifications contain one of the plasmids, the oligonucleotide depicted in SEQ ID:158, the oligonucleotide depicted in SEQ ID:159, the oligonucleotide depicted in SEQ ID:160, 400 µM of dNTPs (100 µM of dATP, 100 µM of dTTP, 100 µM of dGTP and 100 µM of dCTP), recombinant Taq DNA polymerase (Takara Shuzo), the PCR buffer provided with the recombinant Taq DNA polymerase. In these PCR amplifications, there are repeated 30 times, an incubation cycle entailing an incubation at 94° C. for 30 seconds, then an incubation at 65° C. for 1 minute, which is followed by an incubation at 72° C. for 1 minute and 45 seconds. Ten microliters (10 µl) of each of the resulting 25 µl PCR mixtures are subjected to a 1% agarose gel electrophoresis (Agarose S, Nippon Gene) to confirm that the resulting plasmids have a size of about 1.2 kb. The plasmids are then prepared with a Dye Terminator Sequence Kit FS (Applied Biosystems). The prepared samples of the plasmids are sequenced, respectively, with an ABI autosequencer (Model 377, Applied Biosystems).

It is confirmed from the sequencing that the plasmid derived from pSK-NN303 encodes the human mutant ERα K303R (AAG→AGG; lysine→arginine; relative position 303). This plasmid is designated as pRc/RSV-hERαK303R Kozak.

It is confirmed from the sequencing that the plasmid derived from pSK-NN309 encodes the human mutant ERα S309F (TCC→TTC; serine→phenylalanine; relative position 309). This plasmid is designated as pRc/RSV-hERαS309F Kozak.

It is confirmed from the sequencing that the plasmid derived from pSK-NN396 encodes the human mutant ERα M396V (ATG→GTG; methionine→valine; relative position 396). This plasmid is designated as pRc/RSV-hERαM396V Kozak.

It is confirmed from the sequencing that the plasmid derived from pSK-NN415 encodes the human mutant ERα

G415V (GGA→GTA; glycine→valine; relative position 415). This plasmid is designated as pRc/RSV-hERαG415V Kozak.

It is confirmed from the sequencing that the plasmid derived from pSK-NN494 encodes the human mutant ERα G494V (GGC→GTC; glycine→valine; relative position 494). This plasmid is designated as pRc/RSV-hERαG494V Kozak.

It is confirmed from the sequencing that the plasmid derived from pSK-NN531 encodes the human mutant ERα K531E (AAG→GAG; lysine→glutamic acid; relative position 531). This plasmid is designated as pRc/RSV-hERαK531E Kozak.

Table 5 below shows the plasmid utilized to produce the plasmid and the resulting plasmid produced therefrom.

TABLE 5

| plasmid | produced plasmid | encoded human mutant ERα |
|---|---|---|
| pSK-NN303 | pRc/RSV-hERK303R Kozak | human mutant ERαK303R |
| pSK-NN309 | pRc/RSV-hERS309F Kozak | human mutant ERαS309F |
| pSK-NN396 | pRc/RSV-hERM396V Kozak | human mutant ERαM396V |
| pSK-NN415 | pRc/RSV-hERG415V Kozak | human mutant ERαG415V |
| pSK-NN494 | pRc/RSV-hERG494V Kozak | human mutant ERαG494V |
| pSK-NN531 | pRc/RSV-hERK531E Kozak | human mutant ERαK531E |

6.1.3. Production of Plasmids Encoding the Human Mutant ERαG390D, S578P or G390D/S578P 6.1.3.1. Production of Plasmids Encoding the Human Mutant ERαG390D and S578P The QuickChange Site-Directed Mutagenesis Kit (Stratagene) is used to mutagenize the plasmid pRc/RSV-hERα Kozak, described in the above 6.1.1., so that the mutagenized plasmid encodes the human mutant ERαG390D or the human mutant ERαS578P. In using the oligonucleotides depicted in SEQ ID: 17 and SEQ ID: 18, the GGT codon encoding the glycine present at relative position 390 is changed to a GAT variant codon encoding aspartic acid. In using the oligonucleotides depicted in SEQ ID:27 and SEQ ID:28, the TCC codon encoding the serine present at relative position 578 is changed to a CCC variant codon encoding proline. The manual provided with the QuickChange Site-Directed Mutagenesis Kit is used to produce the plasmids pRc/RSV-hERαG390D Kozak (GGT→GAT; glycine→aspartic acid; relative position 390) and pRc/RSV-hERαS578P Kozak (TCC→CCC; serine→proline; relative position 578). The plasmids pRc/RSV-hERαG390D Kozak and pRc/RSV-hERαS578P Kozak are sequenced to confirm that the plasmids encoding the human mutant ERα contain the desired mutation therein at relative position 390 or 578.

The QuickChange Site directed Mutagenesis Kit (Stratagene) is then used to mutagenize pRc/RSV-hERαG390D Kozak so that the mutagenized plasmid encodes the human mutant ERαG390D/S578P. The oligonucleotides depicted in SEQ ID:27 and SEQ ID:28 are used to produce plasmid pRc/RSV-hERαG390D/S578P Kozak (GGT→GAT; glycine→aspartic acid; relative position 390 and TCC→CCC; serine→proline; relative position 578). The plasmid pRc/RSV-hERαG390D/S578P Kozak is sequenced to confirm that the plasmid encoding the human mutant ERα contains the desired mutations therein at relative positions 390 and 578.

6.1.3.2. Preparation from a Test Human Liver Tissue Sample of a Plasmid Encoding a Human Mutant ERαG390D/S578P A frozen sample of test human liver tissue was utilized to obtain a polynucleotide encoding a human mutant ERαG390D/S578P. In utilizing the test human liver tissue sample, 0.1 g of the test human liver tissue sample was homogenized with a homogenizer in 5 ml of a buffer containing 4M guanidium thiocyanate, 0.1M Tris-HCl (pH 7.5) and 1% β mercaptoethanol. The resulting buffer was layered with 25 ml of an aqueous 5.7M CsCl solution and was ultracentrifuged at 90,000×g for 24 hours to obtain a RNA pellet. After rinsing the RNA pellet with 70% ethanol, the RNA pellet was allowed to dry at room temperature. The RNA pellet was then dissolved in 10 µl of sterile water to a concentration of 1.2 µg/ml. Test cDNAs were then produced by collectively using the RNAs in the RNA solution as a template in a reverse transcription reaction. In producing the test cDNAs, reverse transcriptase (Superscript II; GibcoBRL) was used with 1 µl of the RNA solution, oligo-dT oligonucleotides (Amerscham Pharmacia) and the buffer provided with the reverse transcriptase. The reverse transcription reaction was allowed to react for 1 hour at 37° C., to provide the above the test cDNAs.

Similarly to the above 6.1.1., 1/50 by volume of the test cDNAs were used to produce pRc/RSV-hERαG390D/S578P Kozak. In this regard, the test cDNAs were used to specifically PCR amplify therefrom with oligonucleotides depicted in SEQ ID:11 and SEQ ID:12, the cDNA encoding the human mutant ERαG390D/S578P. The cDNA encoding the human mutant ERαG390D/S578P was then PCR amplified with the oligonucleotides depicted in SEQ ID:151 and SEQ ID:12 to add a Kozak consensus sequence immediately upstream from the start codon (ATG) in the cDNA. The amplified product was then inserted into the HindIII site of the plasmid pRc/RSV to provide pRc/RSV-hERαG390D/S578P Kozak.

6.2. Example 2 Production of a Plasmid Containing the Reporter Gene

An oligonucleotide depicted in SEQ ID:161 and an oligonucleotide having a nucleotide sequence complementary thereto were synthesized with a DNA synthesizer. The oligonucleotide depicted in SEQ ID: 161 was synthesized to encode one of the strands of an ERE derived from the upstream region in a *Xenopus vitellogenin* gene. The second oligonucleotide was synthesized to have a nucleotide sequence complementary to the oligonucleotide depicted in SEQ ID:161. The two oligonucleotides were annealed together to produce a DNA encoding an ERE (hereinafter referred to as the ERE DNA). The ERE DNA was then ligated together with a T4 DNA ligase to provide a EREx5 DNA having a 5 tandem repeat of the ERE. A T4 polynucleotide kinase was allowed to react with the EREx5 DNA to phosphorylate the ends thereof.

An oligonucleotide depicted in SEQ ID: 162 and an oligonucleotide depicted in SEQ ID: 163 were then synthesized with a DNA synthesizer. The oligonucleotide depicted in SEQ ID: 162 was synthesized to encode one of the strands in the nucleotide sequence of a TATA sequence derived from the mouse metallothionein I gene and the leader sequence thereof. The oligonucleotide depicted in SEQ ID: 163 was synthesized to encode a nucleotide sequence complementary to the oligonucleotide depicted in SEQ ID: 162. The oligonucleotides depicted in SEQ ID: 162 and SEQ ID:163 were annealed together to produce a DNA encoding the TATA sequence. A T4 polynucleotide kinase was allowed to react with the DNA encoding the TATA sequence to phosphorylate the ends thereof.

The plasmid pGL3 (Promega), which encodes the firefly luciferase gene, was restriction digested with restriction enzymes Bgl II and Hind III and was then treated with BAP at 65° C. for 1 hour. The restriction digestion reaction mixture was then subjected to low melting point agarose gel electrophoresis (Agarose L, Nippon Gene) to confirm that there was a DNA fragment having the nucleotide sequence encoding the firefly luciferase. The DNA fragment having the nucleotide sequence encoding the firefly luciferase was then recovered from the low melting point agarose gel. Subsequently, 100 ng of the recovered DNA fragment and 1 μg of the DNA encoding the TATA sequence were used in a ligation reaction with T4 DNA ligase to provide a plasmid pGL3-TATA.

The plasmid pGL3-TATA was restriction digested with restriction enzyme Sma I and was then treated with BAP at 65° C. for 1 hour. The restriction digestion reaction mixture was then subjected to low melting point agarose gel electrophoresis (Agarose L, Nippon Gene) to confirm that there was a DNA fragment encoding the TATA sequence and the firefly luciferase. After recovering such a DNA fragment from the low melting point agarose gel, 100 ng of the recovered DNA fragment and 1 μg of the EREx5 DNA were used in a ligation reaction with T4 DNA ligase to provide a plasmid pGL3-TATA-EREx5.

The plasmid pUCSV-BSD (Funakoshi) was restriction digested with restriction enzyme BamH I to prepare a DNA encoding a blasticidin S deaminase gene expression cassette. Further, the plasmid pGL3-TATA-EREx5 was restriction digested with restriction enzyme BamH I and was then treated with BAP at 65° C. for 1 hour. The DNA fragment encoding a blasticidin S deaminase gene expression cassette was then mixed with the restriction digested pGL3-TATA-EREx5. The mixture was then used in a ligation reaction with T4 DNA ligase to provide plasmids. The ligation reaction mixture was used to transform E. coli competent DH5α cells. The transformed cells are cultured in LB-amp. The clones thereof showing an ampicillin resistance are then recovered. Some of the clones are then used to isolate therefrom the plasmids derived from the ligation reaction. An aliquot sample of each of the isolated plasmids are then restriction digested with restriction enzyme BamH I. The restriction digestion reaction mixtures were then subjected to agarose gel electrophoresis to confirm whether there was a plasmid which has a structure in which the DNA encoding a blasticidin S deaminase gene expression cassette has been inserted into the Bam HI restriction site in pGL3-TATA-EREx5. The plasmid having such a structure was selected and was designated as pGL3-TATA-EREx5-BSD.

6.3. Example 3 Production of a Stably Transformed Cassette Cell

In order to produce stably transformed cassette cells, which stably contain in one of its chromosomes the reporter gene produced in 6.2. (hereinafter referred to as the ERE reporter gene), the plasmid pGL3-TATA-EREx5-BSD was linearized and introduced into HeLa cells.

The plasmid pGL3-TATA-EREx5-BSD was restriction digested with restriction enzyme Sal I to linearize pGL3-TATA-EREx5-BSD.

Approximately $5 \times 10^5$ HeLa cells were cultured as host cells for 1 day using culture dishes having a diameter of about 10 cm (Falcon) in DMEM medium (Nissui Pharmaceutical Co.) containing 10% FBS at 37° C. under the presence of 5% $CO_2$.

The linearized pGL3-TATA-EREx5-BSD were then introduced to the cultured HeLa cells by a lipofection method using lipofectamine (Life Technologies). According with the manual provided with the lipofectamine, the conditions under the lipofection method included 5 hours of treatment, 7 μg/dish of the plasmids above and 21 μl/dish of lipofectamine.

After the lipofection treatment, the DMEM medium was exchanged with DMEM medium containing 10% FBS and the transformed HeLa cells were cultured for about 36 hours. Next, the transformed HeLa cells were removed and collected from the dish by trypsin treatment and were transferred into a container containing a medium to which blasticidin S was added to a concentration of 16 μg/ml. The transformed HeLa cells were cultured in such medium containing blasticidin S for 1 month while exchanging the medium containing blasticidin S every 3 or 4 days to a fresh batch of the medium containing blasticidin S.

The resulting clones, which were able to proliferate and produce a colony having a diameter of from 1 to several mm, were transferred as a whole to the wells of a 96-well ViewPlate (Berthold) to which medium had previously been dispensed thereto. The colonies of the clones were further cultured. When the colonies proliferated to such a degree that they covered 50% or more of the bottom surface of the well (about 5 days after the transfer), the clones were removed and collected by trypsin treatment. The clones then were divided into 2 subcultures. One of the subcultures was transferred to a 96-well ViewPlate, which was designated as the master plate. The other subculture was transferred to a 96-well ViewPlate, which was designated as the assay plate. The master plate and the assay plate contained medium so that the clones could be cultured. The master plate was continuously cultured under similar conditions.

After culturing the subcultures in the assay plate for 2 days, the medium was then removed from the wells of the assay plate and the clones attached to the well walls were washed twice with PBS(−). A 5-fold diluted lysis buffer PGC50 (Toyo Ink) was added to the subcultures in the wells of the assay plate at 20 μl per well. The assay plate was left standing at room temperature for 30 minutes and were set on a luminometer LB96P (Berthold), which was equipped with an automatic substrate injector. Subsequently, 50 μl of the substrate solution PGL100 (Toyo Ink) was automatically dispensed to each of the lysed clones in the assay plate to measure the luciferase activity therein with the luminometer LB96P. Ten (10) clones, which exhibited a high luciferase activity were selected therefrom.

Samples of the clones in the master plate, which correspond to the selected 10 clones were then cultured at 37° C. for 1 to 2 weeks in the presence of 5% $CO_2$ using dishes having a diameter of about 10 cm (Falcon) in medium.

The plasmid pRc/RSV-hERαKozak was then introduced to the selected clones by a lipofection method using lipofectamine (Life Technologies) to provide a second round of clones. According with the manual provided with the lipofectamine, the conditions under the lipofection method included 5 hours of treatment, 7 μg/dish of the plasmids above and 21 μl/dish of lipofectamine. A DMSO solution containing 17β-E2 was then added to the resulting second clones to a concentration of 10 nM. After culturing the second clones for 2 days, the luciferase activity was measured, similarly to the above, for each of the second clones. The clone in the master plate, which provided the second clone exhibiting the highest induction of luciferase activity, was selected as the stably transformed cassette cell which stably contained in one of its chromosomes the ERE reporter gene (hereinafter referred to as the stably transformed ERE cassette cell).

6.4. Example 4 Production of Stably Transformed Binary Cells

Four stably transformed cells containing the ERE reporter gene with the human mutant ERαG390D, S578P or G390D/S578P or human normal ERα (hereinafter referred to as the stably transformed ERE binary cells) were produced. The first stably transformed ERE binary cell contained in its chromosomes the linearized pGL3-TATA-EREx5-BSD, which encodes the reporter gene, and the linearized pRc/RSV-hERαKozak, which encodes the human normal ERα. The second stably transformed ERE binary cell contained in its chromosomes the linearized pGL3-TATA-EREx5-BSD, which encodes the ERE reporter gene, and the linearized pRc/RSV-hERαG390D Kozak, which encodes the human mutant ERαG390D. The third stably transformed ERE binary cell contained in its chromosomes the linearized pGL3-TATA-EREx5-BSD, which encodes the ERE reporter gene, and the linearized pRc/RSV-hERαS578P Kozak, which encodes the human mutant ERαS578P. The fourth stably transformed ERE binary cell contained in its chromosomes the linearized pGL3-TATA-EREx5-BSD, which encodes the ERE reporter gene, and the linearized pRc/RSV-hERαG390D/S578P Kozak, which encodes the human mutant ERαG390D/S578P.

In order to produce the stably transformed ERE binary cells, the plasmids pGL3-TATA-EREx5-BSD, pRc/RSV-hERαG390D Kozak, pRc/RSV-hERαS578P Kozak and pRc/RSV-hERαG390D/S578P Kozak were each linearized and introduced into HeLa cells. To linearize, the plasmids above were restriction digested with restriction enzyme Sal I.

Approximately $5 \times 10^5$ HeLa cells were cultured as host cells for 1 day using dishes having a diameter of about 10 cm (Falcon) in DMEM medium (Nissui Pharmaceutical Co.) containing 10% FBS at 37° C. under the presence of 5% $CO_2$.

A linearized pGL3-TATA-EREx5-BSD was introduced, respectively, into the HeLa cells with a linearized plasmid encoding a human mutant ERα or human normal ERα, as shown in Table 6 below. The linearized plasmids were introduced into the HeLa cells by a lipofection method using lipofectamine (Life Technologies). According with the manual provided with the lipofectamine, the conditions for each of the treatments under the lipofection method included 5 hours of treatment, 7 μg/dish of the plasmids (3.5 μg each) and 21 μl/dish of lipofectamine.

TABLE 6

| | linearized plasmids |
|---|---|
| first HeLa cells | pGL3-TATA-EREx5-BSD and pRc/RSV-hERαKozak |
| second HeLa cells | pGL3-TATA-EREx5-BSD and pRc/RSV-hERαG390D Kozak |
| third HeLa cells | pGL3-TATA-EREx5-BSD and pRc/RSV-hERαS578P Kozak |
| fourth HeLa cells | pGL3-TATA-EREx5-BSD and pRc/RSV-hERαG390D/S578P Kozak |

After the lipofection treatment, the DMEM mediums were exchanged with DMEM medium containing 10% FBS and the transformed HeLa cells were cultured for about 36 hours. Next, the transformed HeLa cells were removed and collected, respectively, from the dishes by trypsin treatment and were transferred into a container containing a medium to which blasticidin S and G418 was added thereto. The concentration of the blasticidin S therein for each of the cell cultures was 16 μg/ml. The concentration of the G418 therein for each of the cell cultures was 800 μg/ml. The transformed HeLa cells were cultured in such medium containing blasticidin S and G418 for 1 month while exchanging the medium every 3 or 4 days to a fresh batch of the medium containing blasticidin S and G418.

The resulting clones, which were able to proliferate to a diameter of from 1 to several mm, were transferred, respectively, to the wells of 96-well ViewPlates (Berthold) to which medium had previously been dispensed thereto. The clones were further cultured. When the clones proliferated to such a degree that they covered 50% or more of the bottom surface of the well (about 5 days after the transfer), the clones were removed and collected by trypsin treatment. Each of the clones then were divided into 3 subcultures. For each of the clones, one of the subcultures was transferred to a 96-well ViewPlate, which was designated as the master plate. The other two subcultures were transferred, respectively, to 96-well ViewPlates, which were designated as the assay plates. The master plate and the assay plates contained medium so that the clones can be cultured. The master plate is continuously cultured under similar conditions. To each of the subcultures in the first assay plate, a DMSO solution containing 17β-E2 was added to a concentration of 10 nM. An equivalent volume of DMSO was added to the subcultures in the second assay plate. The first and second assay plates were then cultured for 2 days.

The medium was then removed from the wells of the first and second assay plates and the clones attached to the well walls were washed twice with PBS(−). A 5-fold diluted lysis buffer PGC50 (Toyo Ink) was added to the clones in the wells of the first and second assay plates at 20 μl per well. The first and second assay plates were left standing at room temperature for 30 minutes and were set on a luminometer LB96P (Berthold), which was equipped with an automatic substrate injector. Subsequently, 50 μl of the substrate solution PGL100 (Toyo Ink) was automatically dispensed, respectively, to each of the lysed clones in the assay plates to measure the luciferase activity therein with the luminometer LB96P. Clones in master plate corresponding to the clones in the first assay plate which exhibited a 2-fold higher induction of luciferase activity (%) were then selected as the stably transformed ERE binary cell which stably contain the reporter gene with the human mutant ERαG390D, S578P or G390D/S578P gene or the human normal ERα gene.

6.5. Example 5 Reporter Assays of Human Mutant ERα

6.5.1 Preparation of the Stably Transformed ERE Binary Cells for the Reporter Assay About $2 \times 10^4$ cells of the stably transformed ERE binary cells, produced in the above 6.4., were then transferred to the wells of 96-well Luminometer plates (Corning Coaster) to culture overnight the stably transformed ERE binary cells in an E-MEM medium to which a charcoal dextran treated FBS was added to a concentration of 10% (v/v) (hereinafter referred to as charcoal dextran FBS/E-MEM medium).

6.5.2. Introduction of the Plasmids Encoding the Human Mutant ERαK303R, S309F, M396V, G415V, G494V or K531E Seven subcultures which contained, respectively, approximately $2 \times 10^6$ cells of the stably transformed ERE cassette cells produced in 6.3., were cultured for 1 day using dishes having a diameter of about 10 cm (Falcon) in charcoal dextran FBS/E-MEM medium.

For transient expression, the plasmid pRc/RSV-hERα-Kozak (produced in 6.1.1., encoding normal ERα) and a plasmid encoding the mutant ERα (produced in 6.1.2.2., i.e., pRc/RSV-hERαK303R Kozak, pRc/RSV-hERαS309F Kozak, pRc/RSV-hERαM396V Kozak, pRc/RSV-hERαG415V Kozak, pRc/RSV-hERαG494V Kozak or pRc/RSV-hERαK531E Kozak, each encoding a human mutant ERα) were introduced, respectively, into the subcultures of the stably transformed ERE cassette cells by a lipofection method using lipofectamine (Life Technologies). According with the manual provided with the lipofectamine, the conditions for each of the treatments under the lipofection method included 5 hours of treatment, 7 μg/dish of the plasmids and 21 μl/dish of lipofectamine. After culturing the resulting cell subcultures at 37° C. for 16 hours in the presence of 5% $CO_2$, the charcoal dextran FBS/E-MEM medium therein was exchanged to fresh batches of the charcoal dextran FBS/E-MEM medium to further culture each of the cell subcultures for 3 hours. The cell subcultures were then collected, respectively, and uniformly suspended in charcoal dextran FBS/E-MEM medium.

6.5.3. Measurement of the Activity for Transactivation of the Reporter Gene

Four (4) general types of DMSO solutions were used to expose the cells in the subcultures prepared in the above 6.5.1. and 6.5.2. with various concentrations of a pure or partial anti-estrogen. The first DMSO solutions were prepared to contain a partial anti-estrogen (4-hydroxytamoxifen or raloxifene) at various concentrations. The second DMSO solutions were prepared to contain a pure anti-estrogen (ZM189154) at various concentrations. The third DMSO solutions were prepared to contain E2 at 10 nM and a partial anti-estrogen (4-hydroxytamoxifen or raloxifene) at various concentrations. The fourth DMSO solutions were prepared to contain E2 at 10 nM and a pure anti-estrogen (ZM189154) at various concentrations.

The first, second, third or fourth DMSO solution was then added to the subcultures prepared, in the above 6.5.1. and 6.5.2., as shown in Tables 7, 8, 9 and 10 below. The first, second, third or fourth DMSO solution was added to the wells of the 96-well ViewPlates such that the concentration of the first, second, third or fourth DMSO solution in each of the wells was about 0.1% (v/v). Further, 2 controls were prepared for each of the subcultures in the wells of a 96-well ViewPlate. One of the controls was exposed to DMSO (containing no partial or pure anti-estrogen). The second control was exposed to a DMSO solution consisting essentially of 100 pM of E2.

The cells were then cultured for 36 to 40 hours at 37° C. in the presence of 5% $CO_2$. A 5-fold diluted lysis buffer PGC50 (Toyo Ink) was added, respectively, to the cells in the wells at 50 μl per well. The 96-well ViewPlates were periodically and gently shook while being incubated at room temperature for 30 minutes. Ten microliters (10 μl) of the lysed cells were then transferred, respectively, to white 96-well sample plates (Berthold) and were set on a luminometer LB96P (Berthold), which was equipped with an automatic substrate injector. Subsequently, 50 μl of the substrate solution PGL100 (Toyo Ink) was automatically dispensed, respectively, to each of the lysed cells in the white 96-well sample plates to instantaneously measure for 5 seconds the luciferase activity therein with the luminometer LB96P.

The luciferase activities resulting from the cells prepared in 6.5.2. are illustrated in FIGS. 1 to 32.

Figure 1:
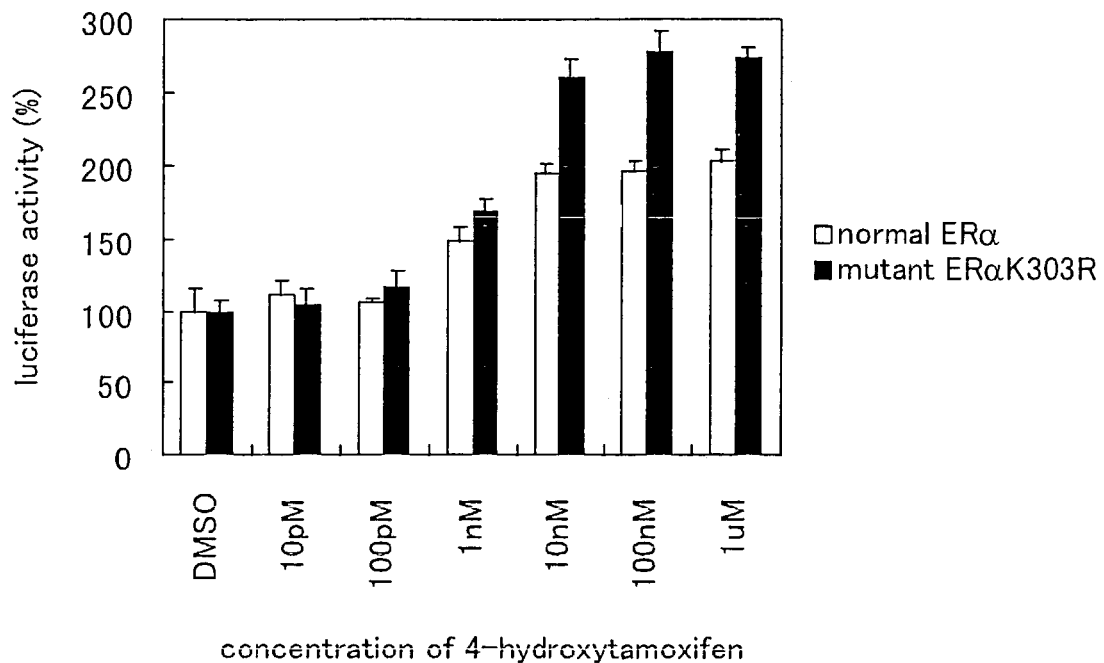
FIGS. 1 and 2 illustrate the luciferase activity provided by the human normal ERα and the human mutant ERαK303R in the presence of 4-hydroxytamoxifen or ZM189154 as the sole possible agent of stimulating the human normal ERα or the human mutant ERαK303R.
Figure 2:
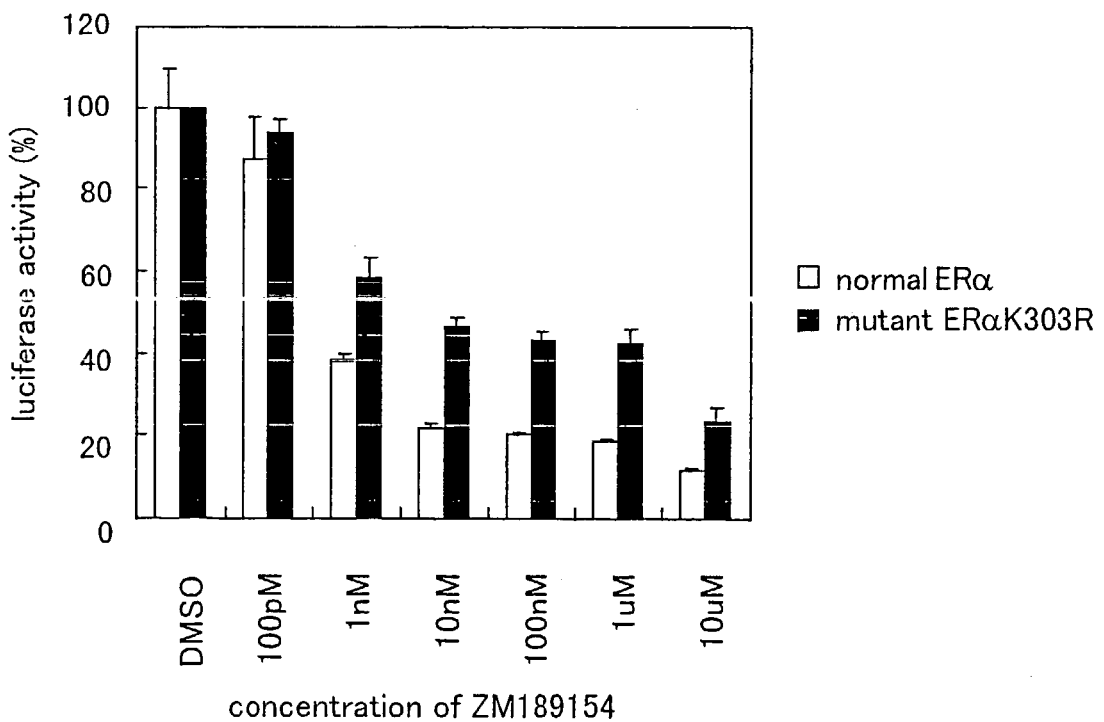
Figure 3:
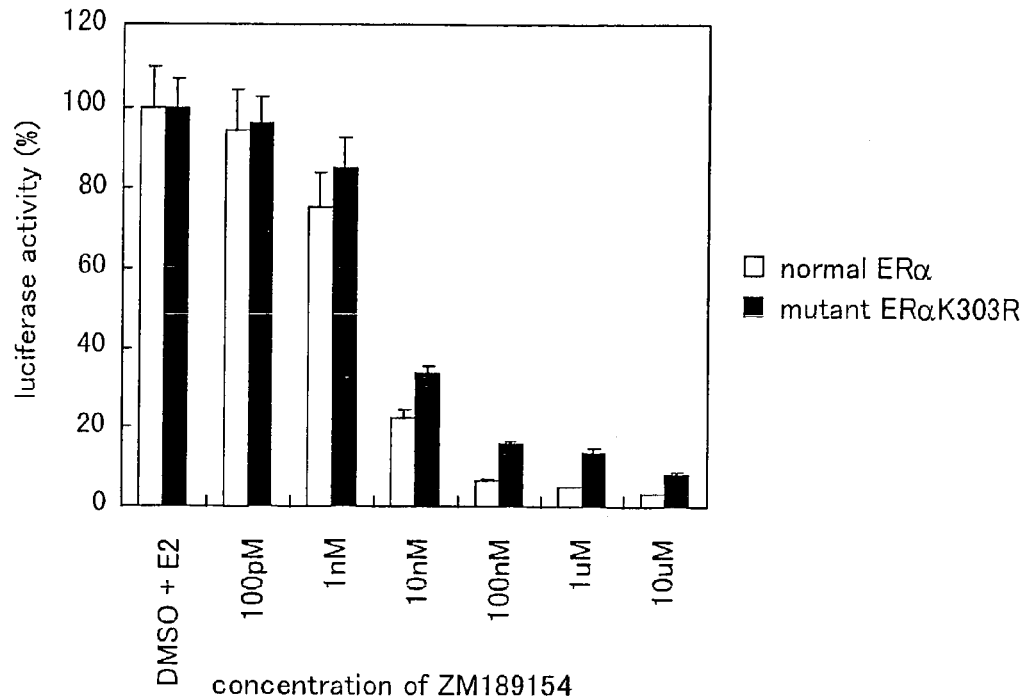
FIG. 3 illustrates the luciferase activity provided by the human normal ERα and the human mutant ERαK303R in the presence of E2 with ZM189154.
Figure 4:
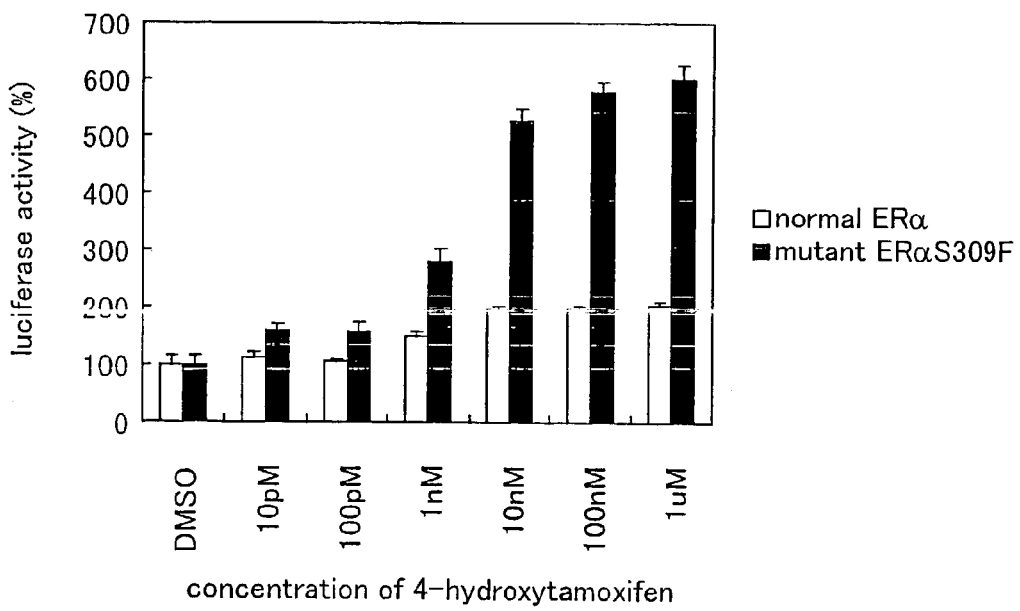
FIGS. 4 and 5 illustrate the luciferase activity provided by the human normal ERα and the human mutant ERαS309F in the presence of 4-hydroxytamoxifen or ZM189154 as the sole possible agent of stimulating the human normal ERα or the human mutant ERαS309F.
Figure 5:
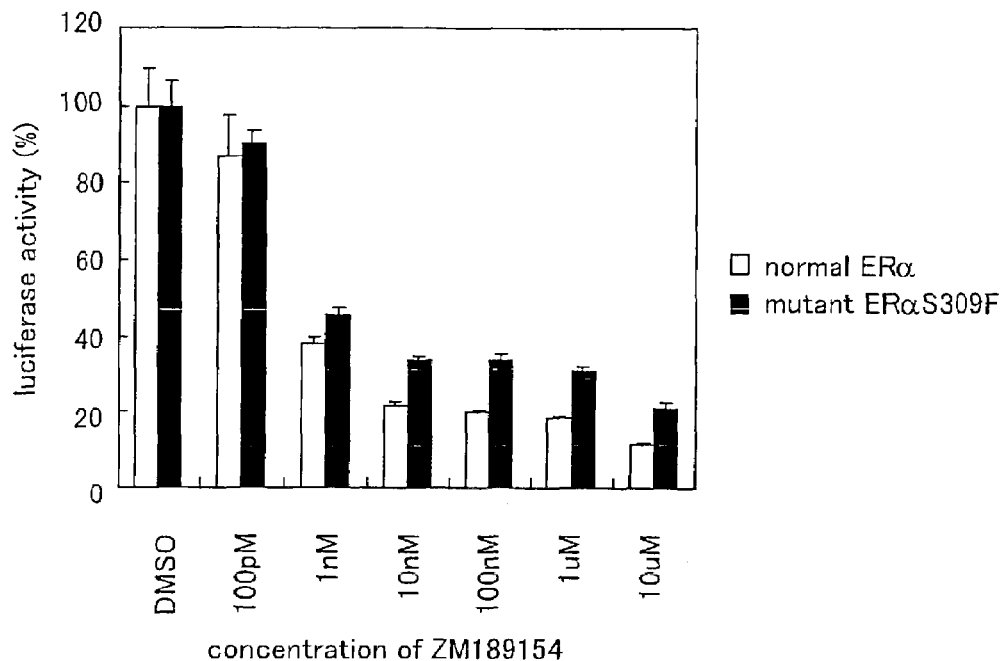
Figure 6:
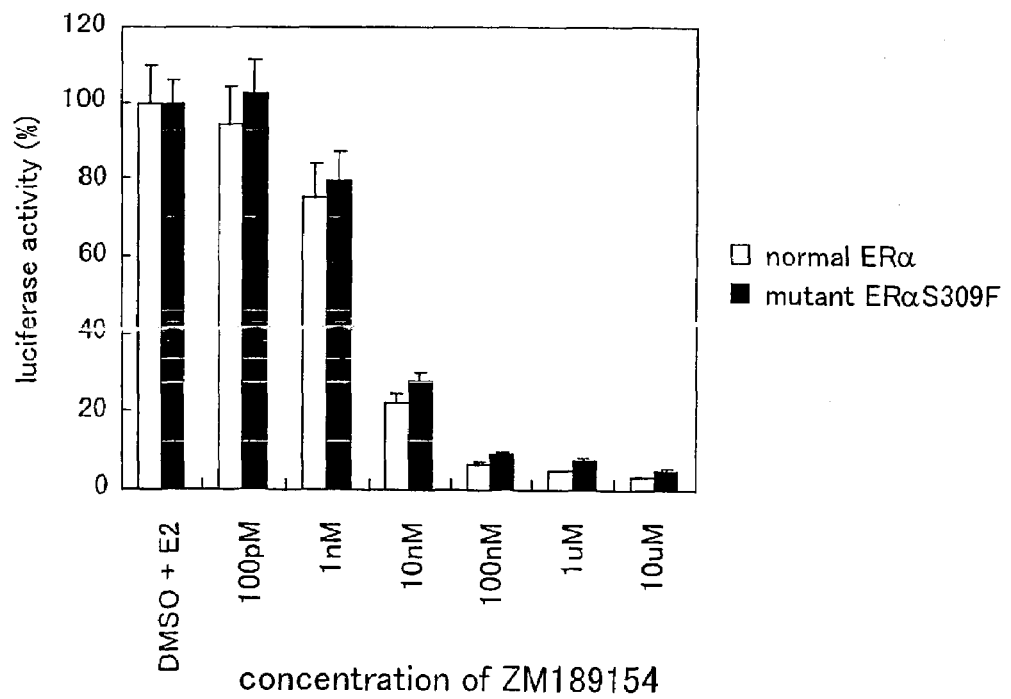
FIG. 6 illustrates the luciferase activity provided by the human normal ERα and the human mutant ERαS309F in the presence of E2 with ZM189154.
Figure 7:
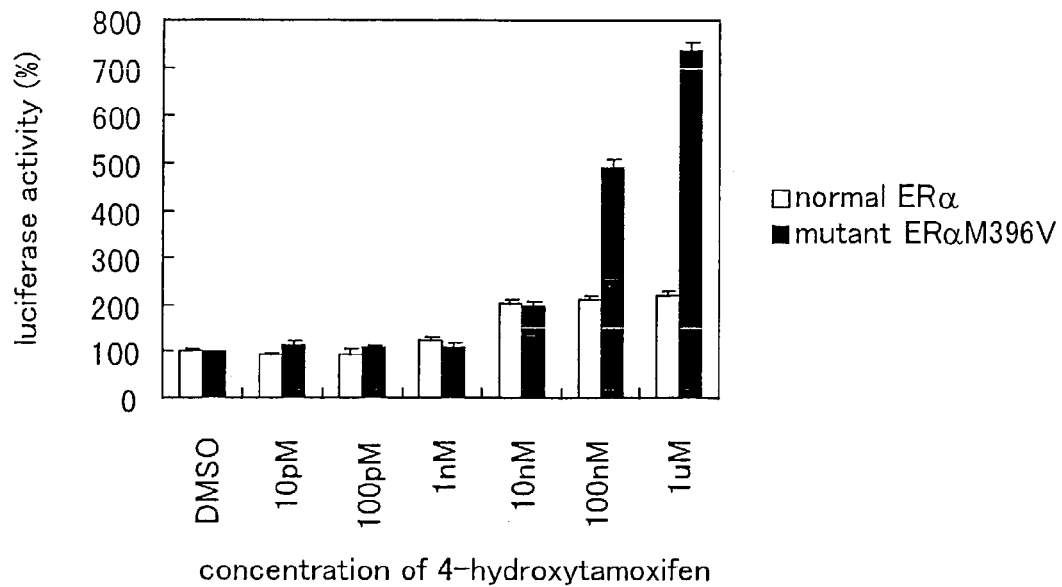
FIGS. 7 and 8 illustrate the luciferase activities provided by the human normal ERα and the human mutant ERαM396V in the presence of 4-hydroxytamoxifen or raloxifene as the sole possible agent of stimulating the human normal ERα or the human mutant ERαM396V.
Figure 8:
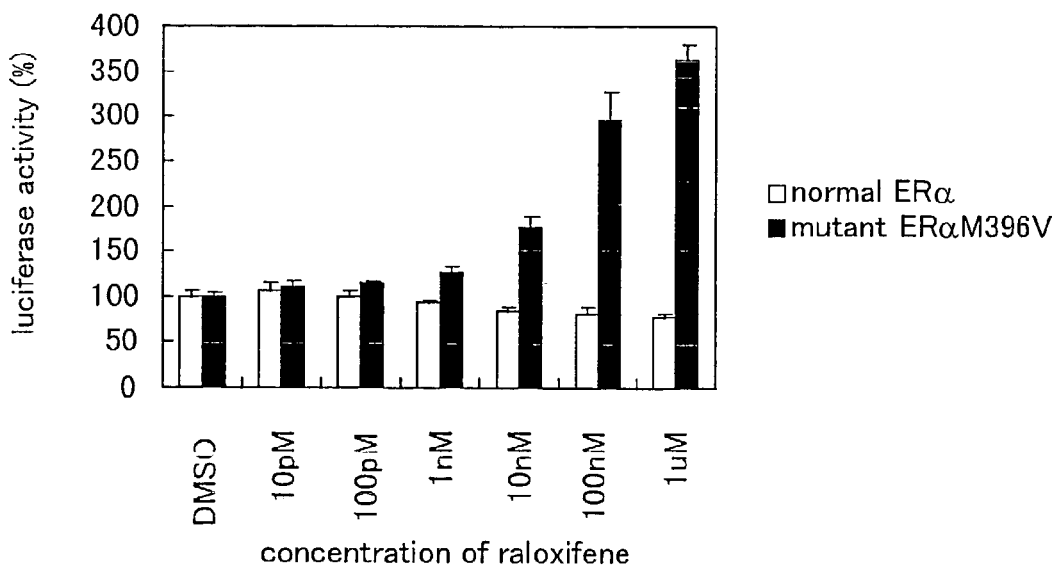
Figure 9:
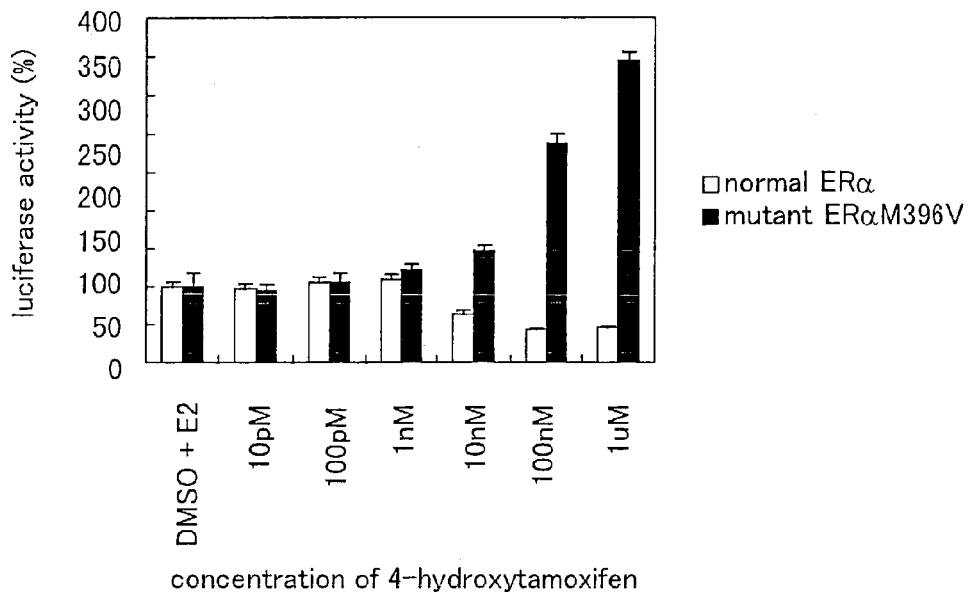
FIGS. 9 to 11 illustrate the luciferase activity provided by the human normal ERα and the human mutant ERαM396V in the presence of E2 with 4-hydroxytamoxifen, raloxifene or ZM189154.
Figure 10:
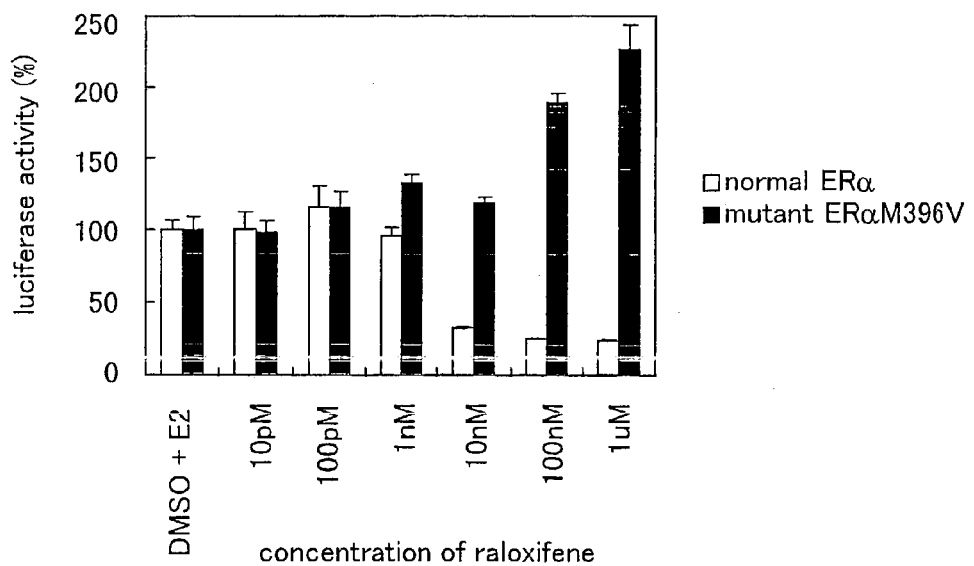
Figure 11:
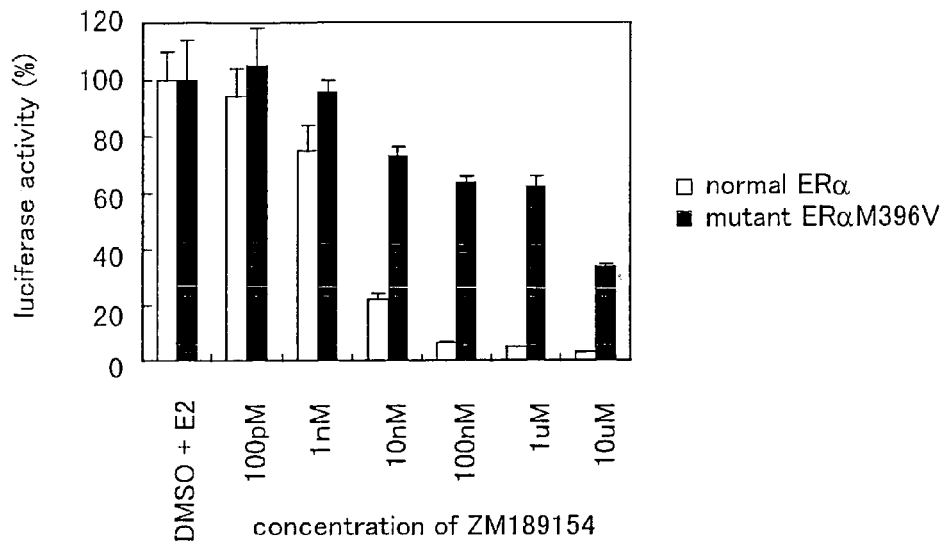
Figure 12:
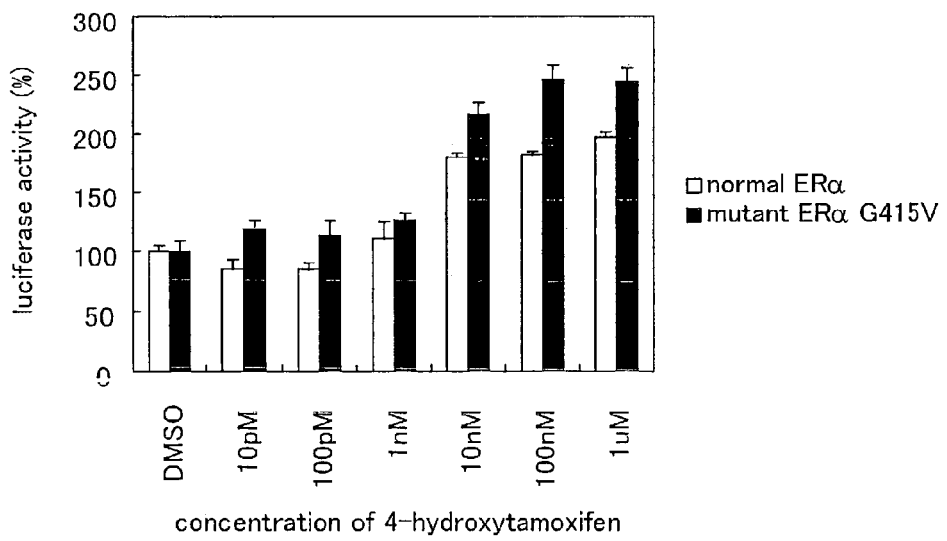
FIGS. 12 and 13 illustrate the luciferase activity provided by the human normal ERα and the human mutant ERαG415V in the presence of 4-hydroxytamoxifen or ZM189154 as the sole possible agent of stimulating the human normal ERα or the human mutant ERαG415V.
Figure 13:
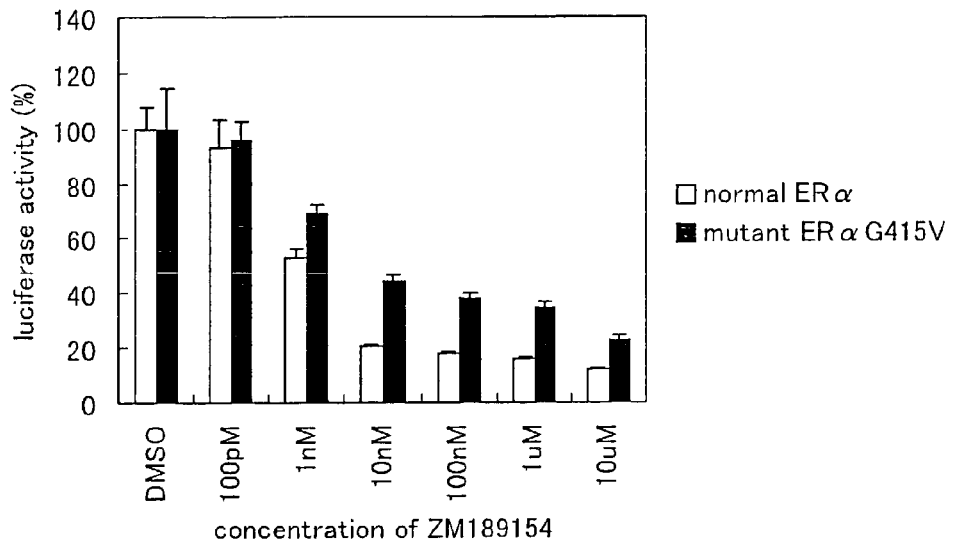
Figure 14:
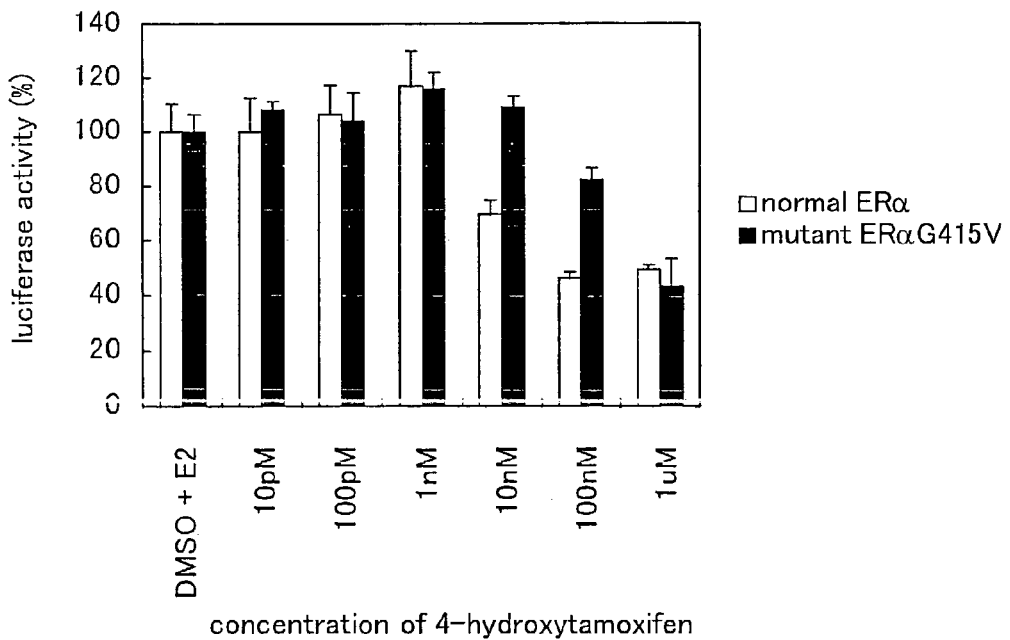
FIGS. 14 and 15 illustrate the luciferase activity provided by the human normal ERα and the human mutant ERαG415V in the presence of E2 with 4-hydroxytamoxifen or ZM189154.
Figure 15:
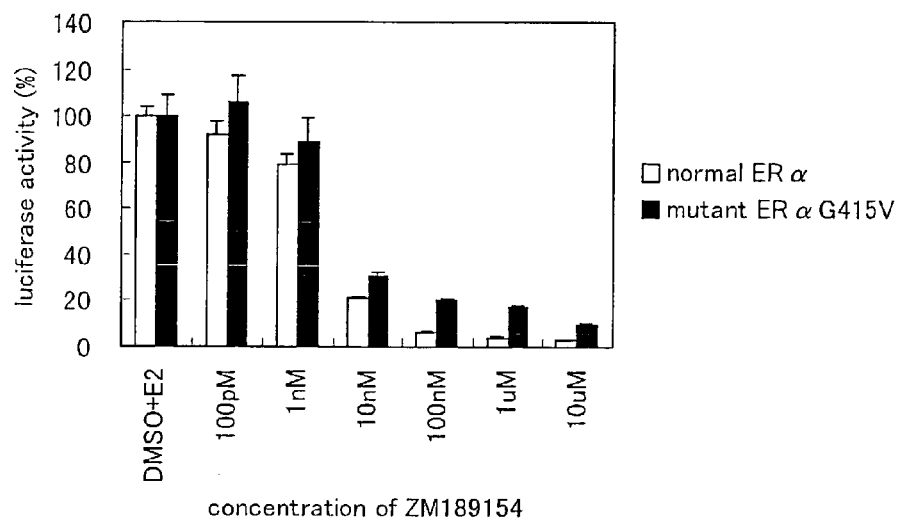
Figure 16:
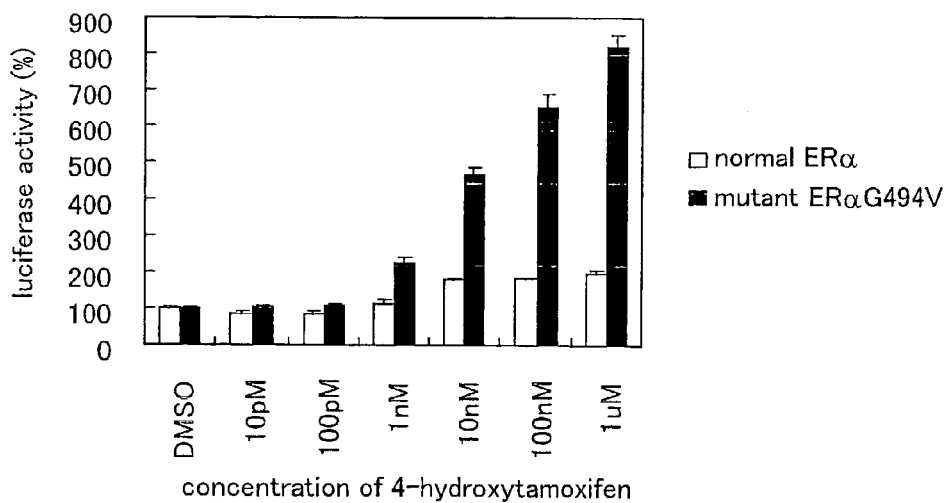
FIGS. 16 to 17 illustrate the luciferase activity provided by the human normal ERα and the human mutant ERαG494V in the presence of 4-hydroxytamoxifen or raloxifene as the sole possible agent of stimulating the human normal ERα or the human mutant ERαG494V.
Figure 17:
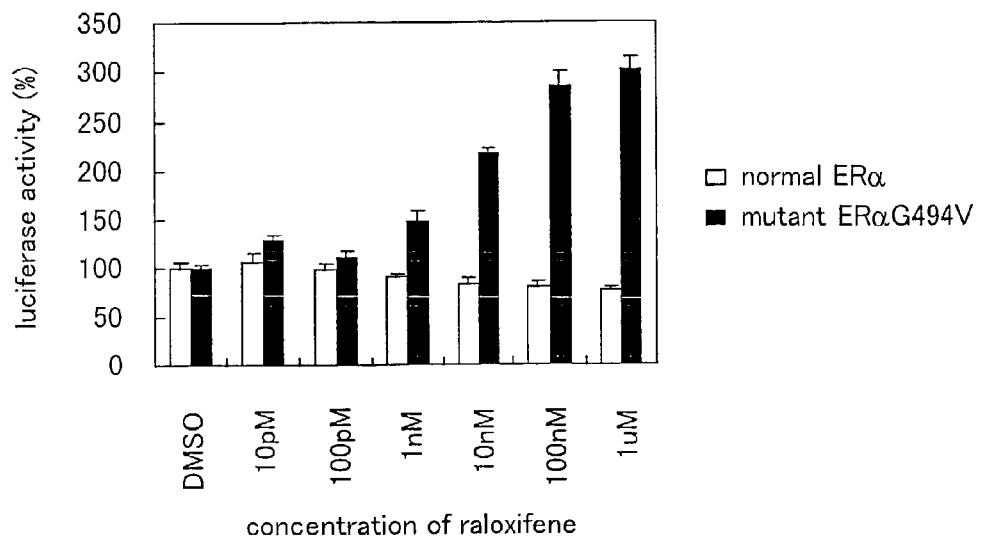
Figure 18:
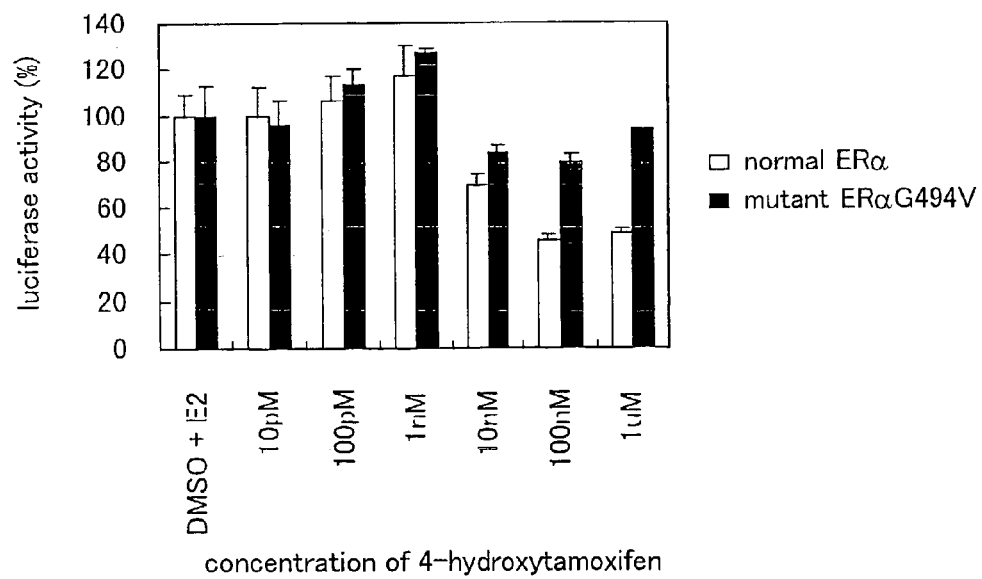
FIGS. 18 to 20 illustrate the luciferase activity provided by the human normal ERα and the human mutant ERαG494V in the presence of E2 with 4-hydroxytamoxifen, raloxifene or ZM189154.
Figure 19:
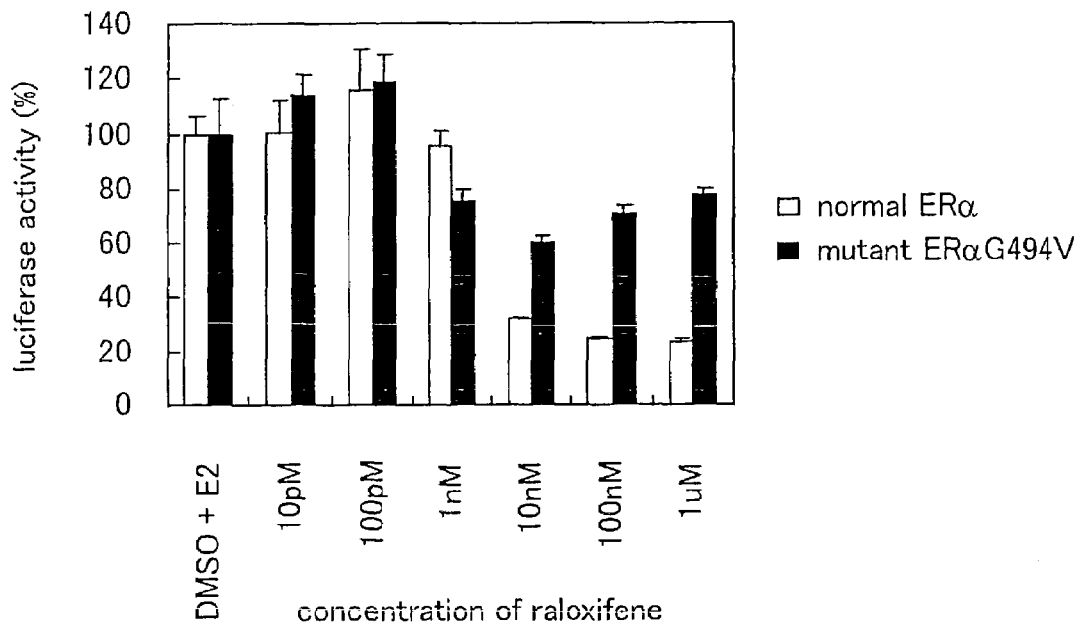
Figure 20:
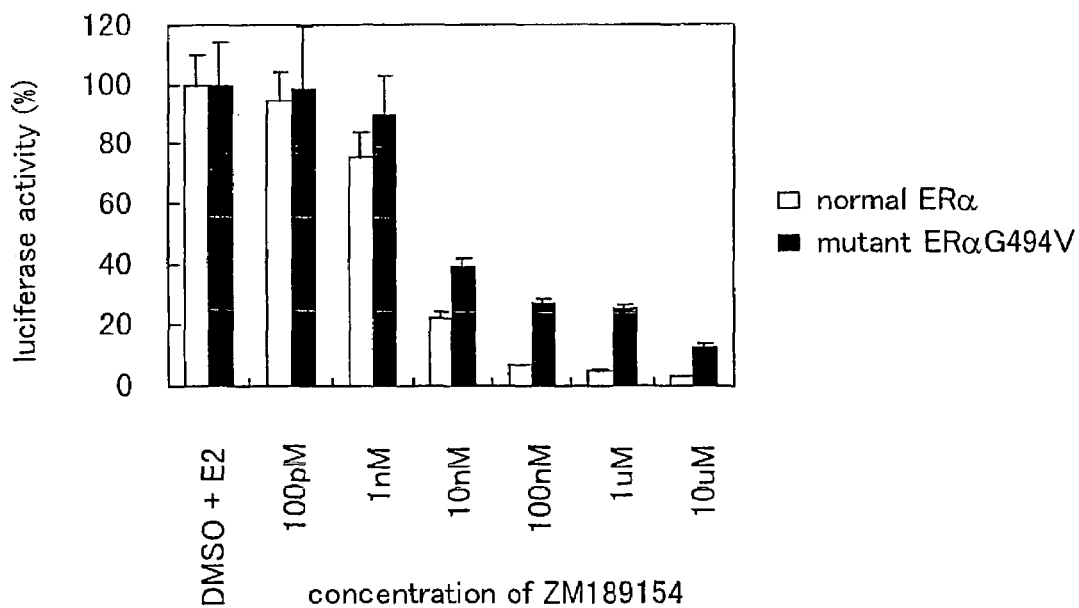
Figure 21:
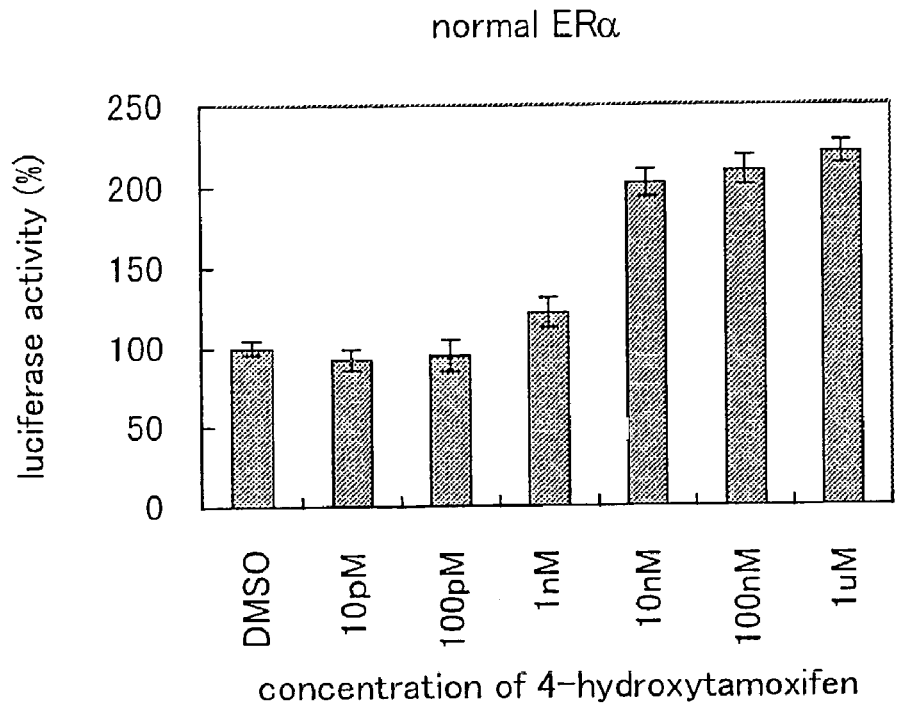
FIGS. 21 to 26 illustrate the luciferase activity provided by the human normal ERα and the human mutant ERαK531E in the presence of 4-hydroxytamoxifen, raloxifene or ZM189154 as the sole possible agent of stimulating the human normal ERα or the human mutant ERαK531E.
Figure 22:
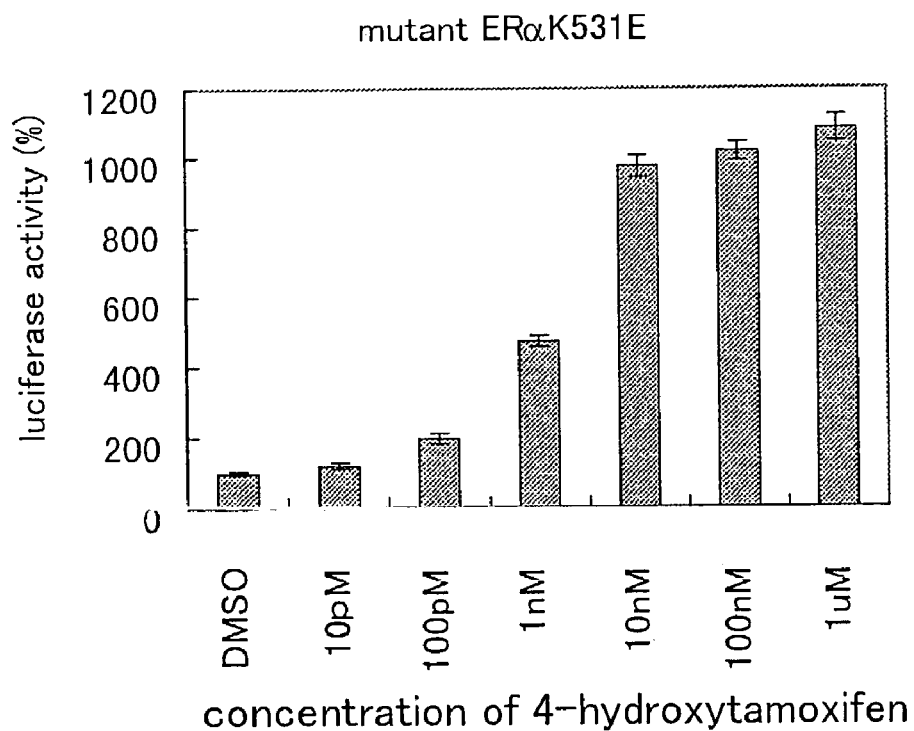
Figure 23:
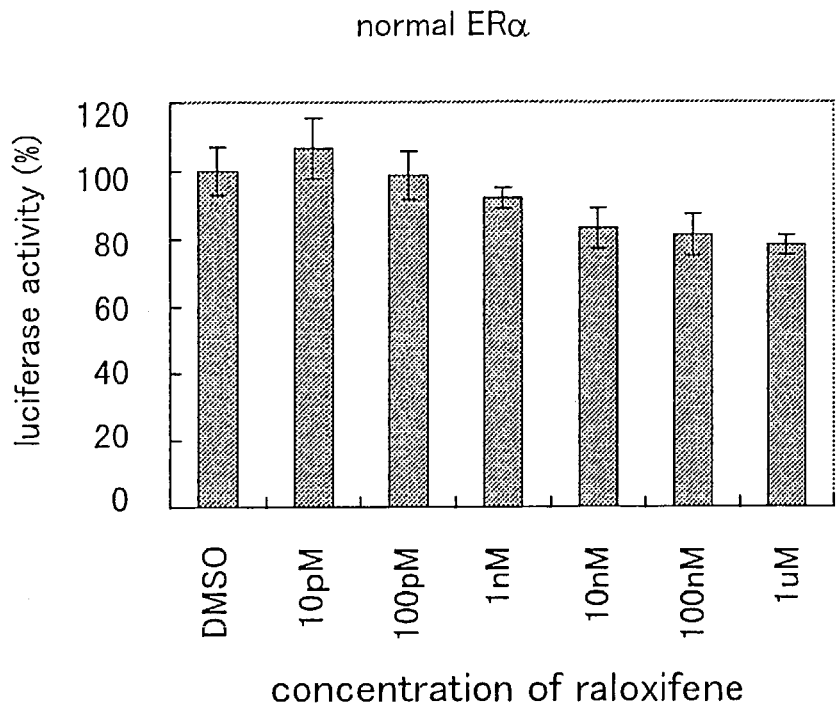
Figure 24:
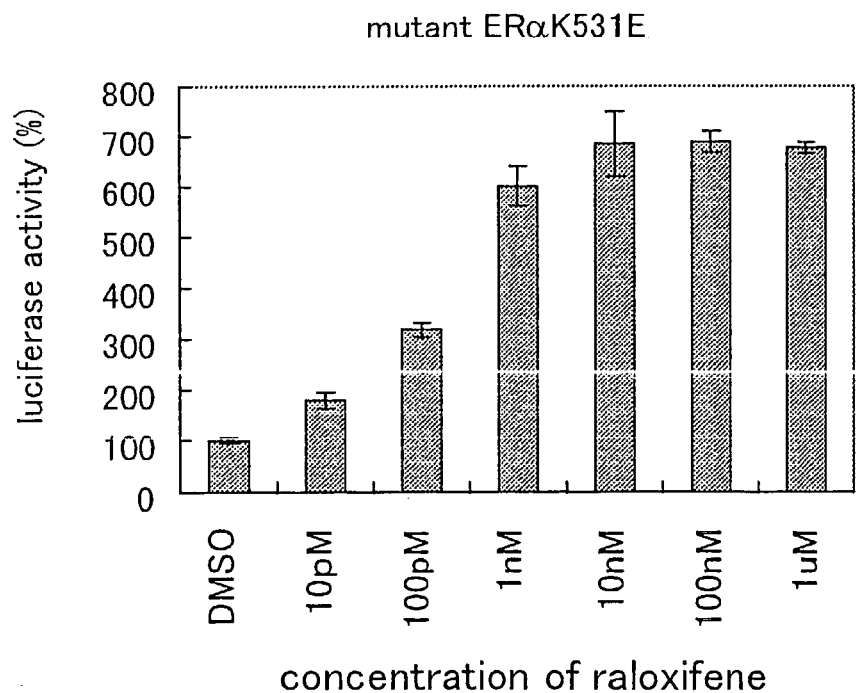
Figure 25:
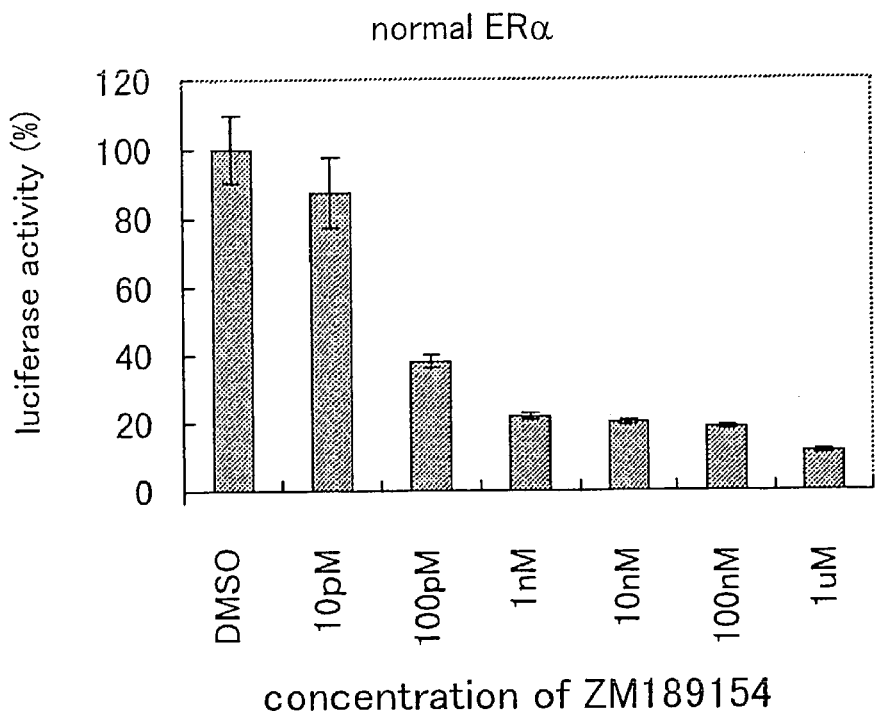
Figure 26:
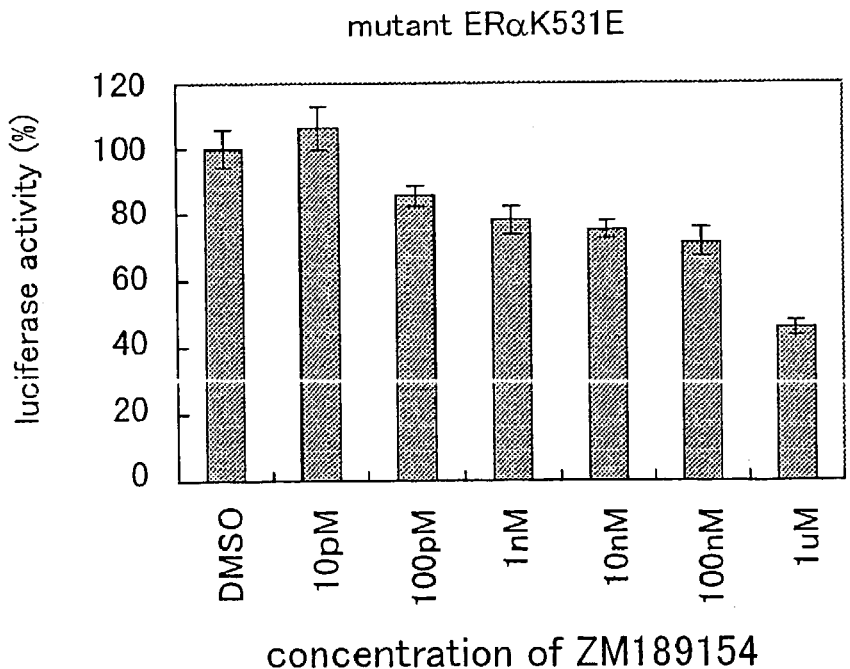
Figure 27:
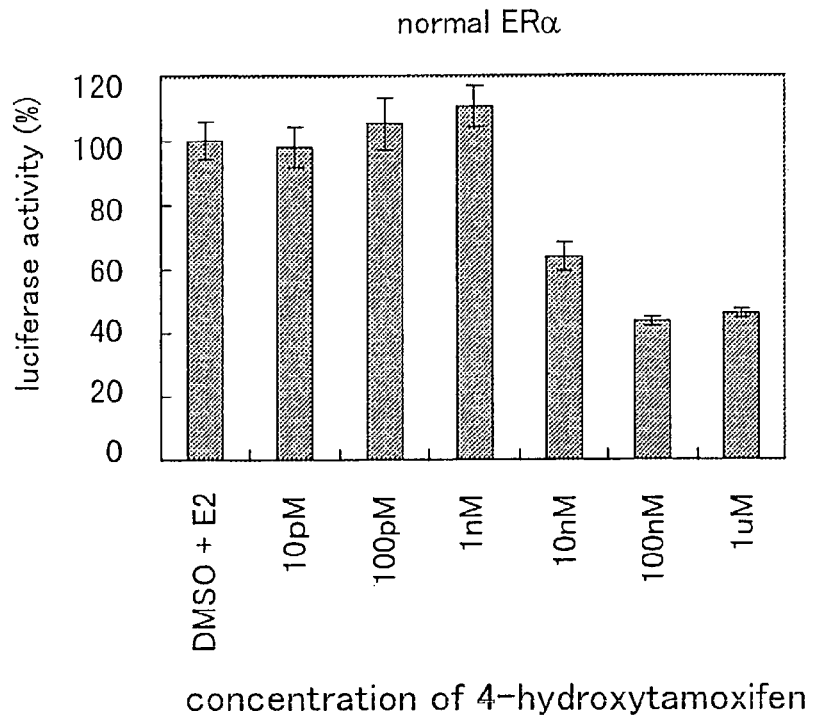
FIGS. 27 to 32 illustrate the luciferase activity provided by the human normal ERα and the human mutant ERαK531E in the presence of E2 with 4-hydroxytamoxifen, raloxifene or ZM189154.
Figure 28:
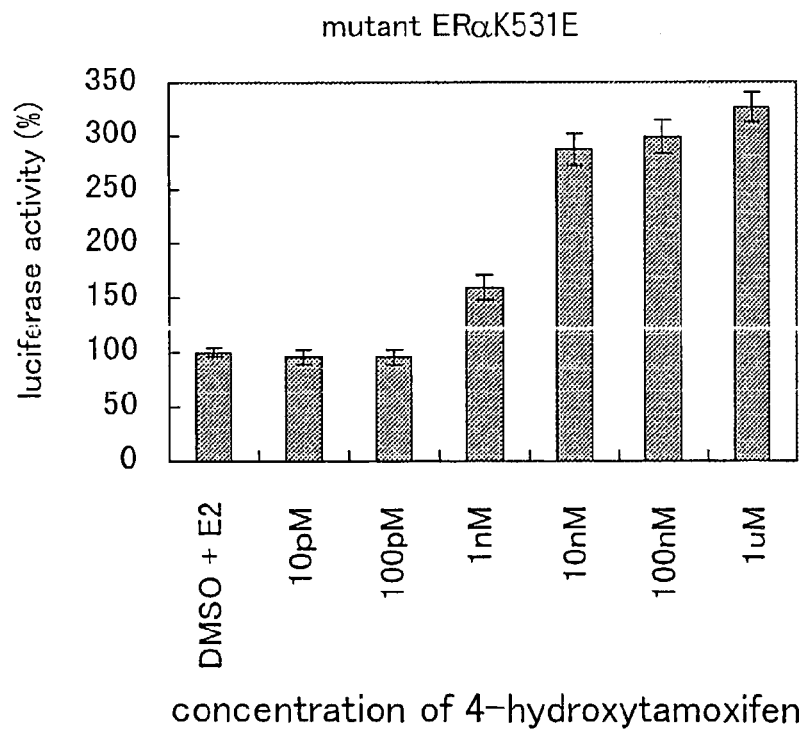
Figure 29:
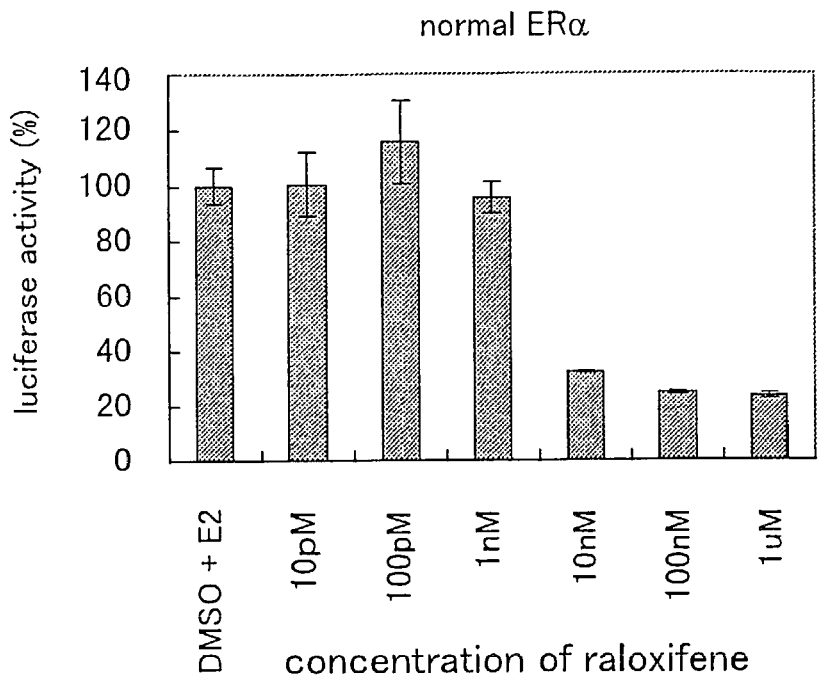
Figure 30:
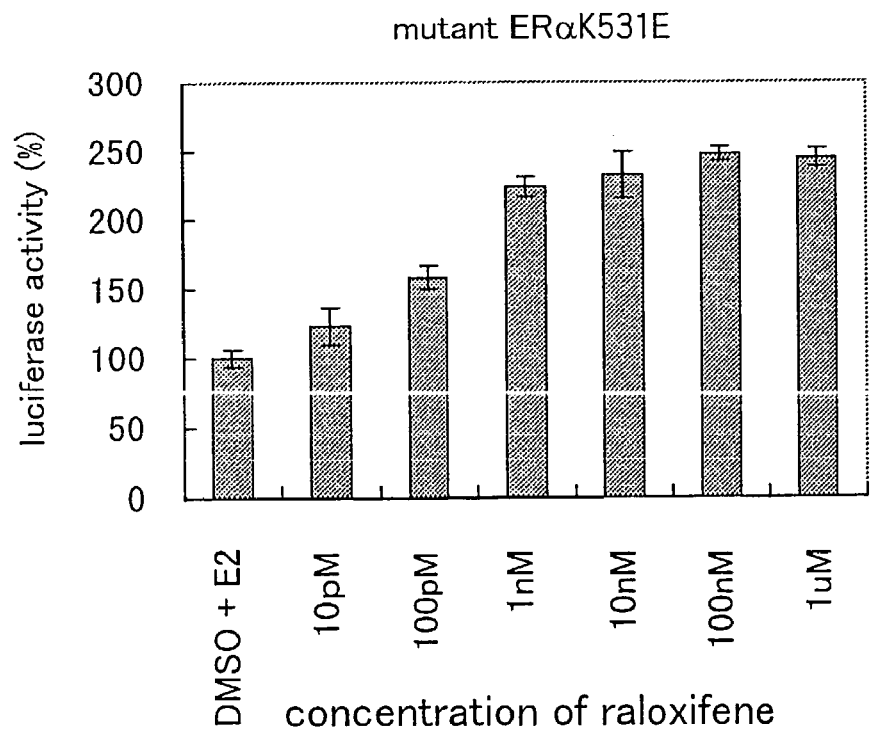
Figure 31:
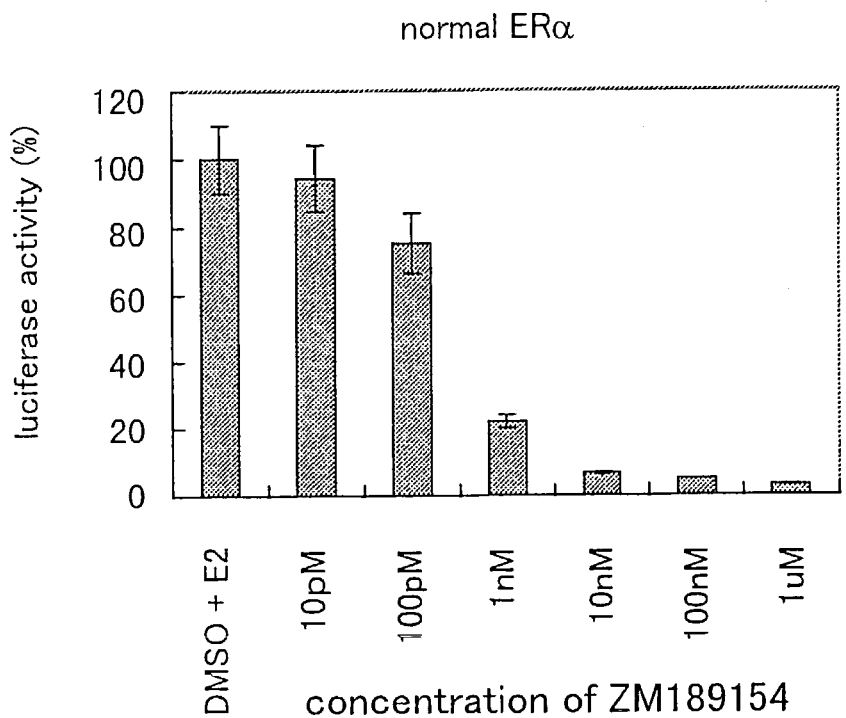
Figure 32:
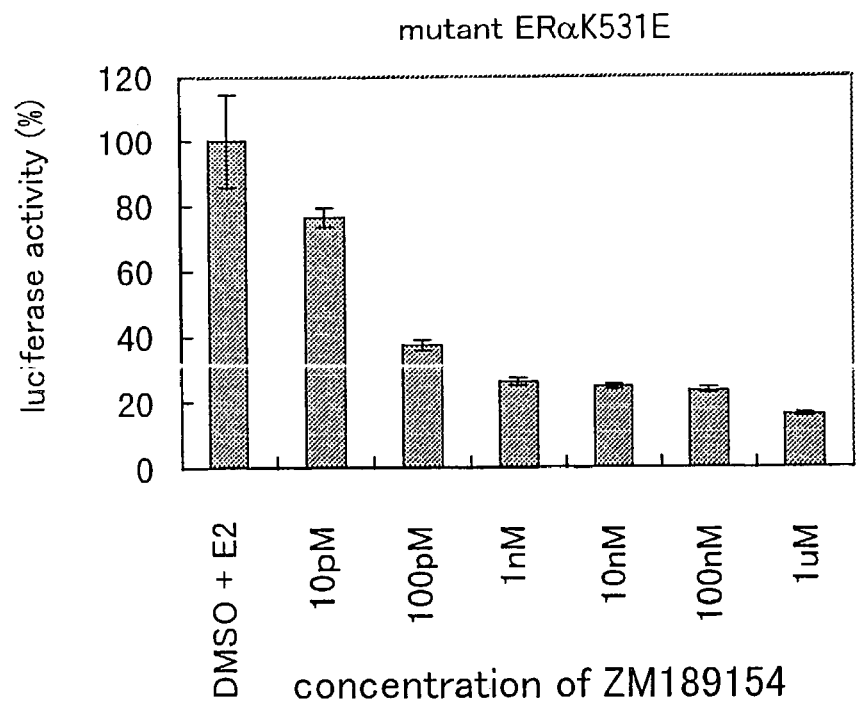
Figure 33:
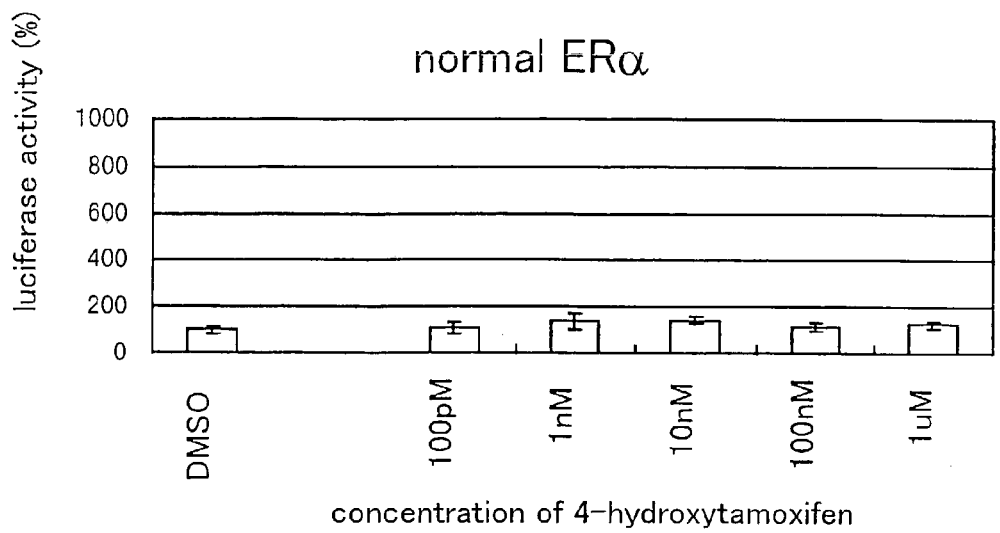
Figure 34:
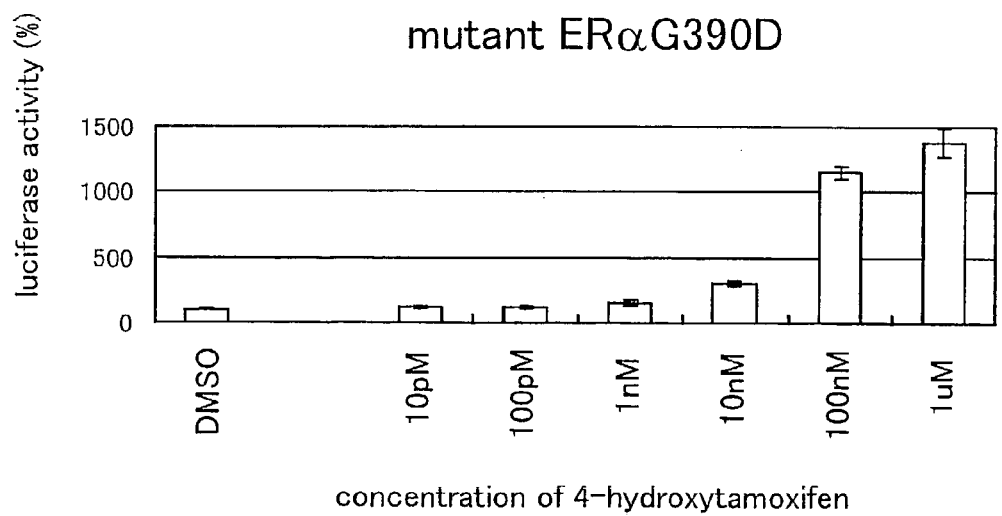
Figure 35:
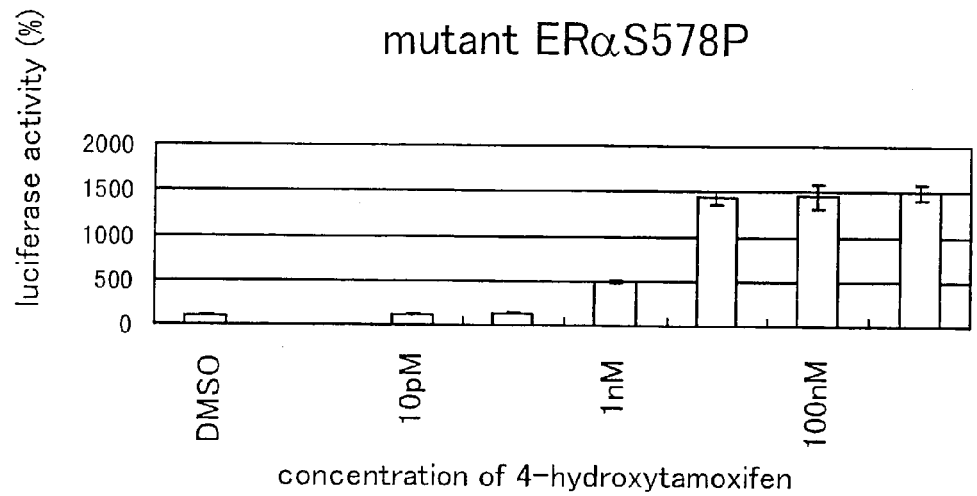
Figure 36:
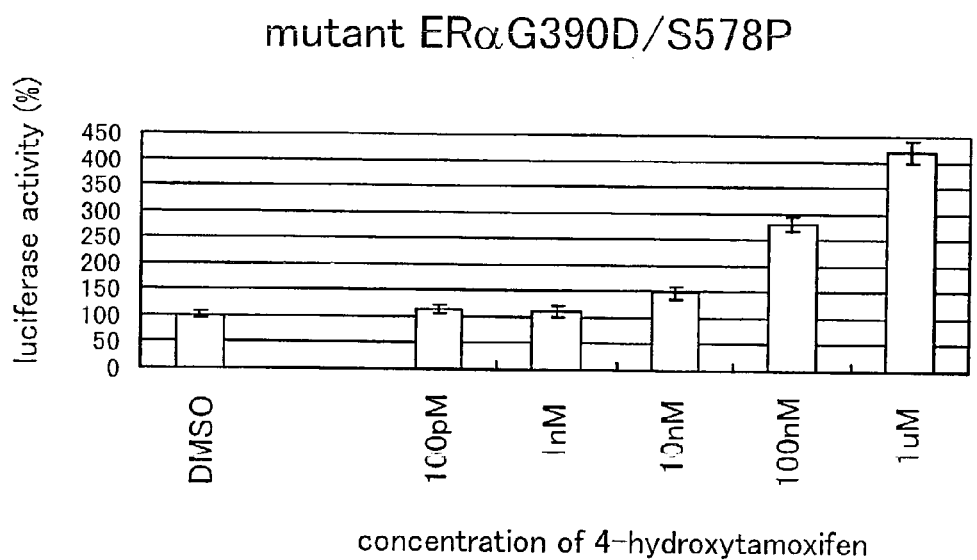
Figure 37:
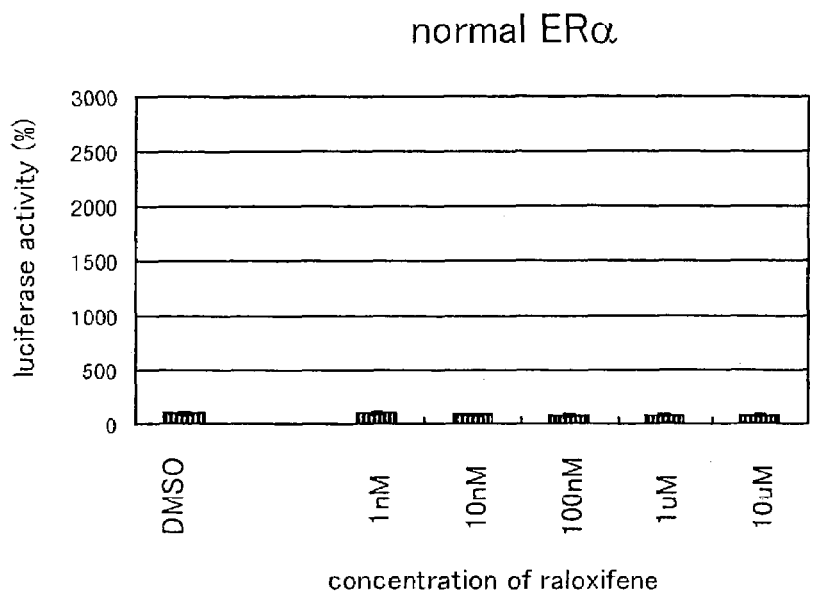
Figure 38:
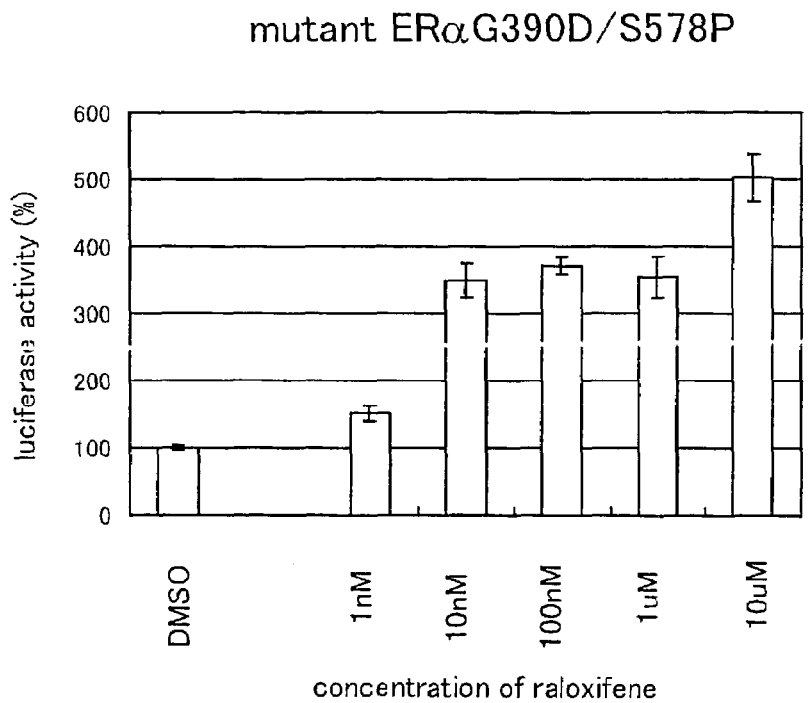
Figure 39:
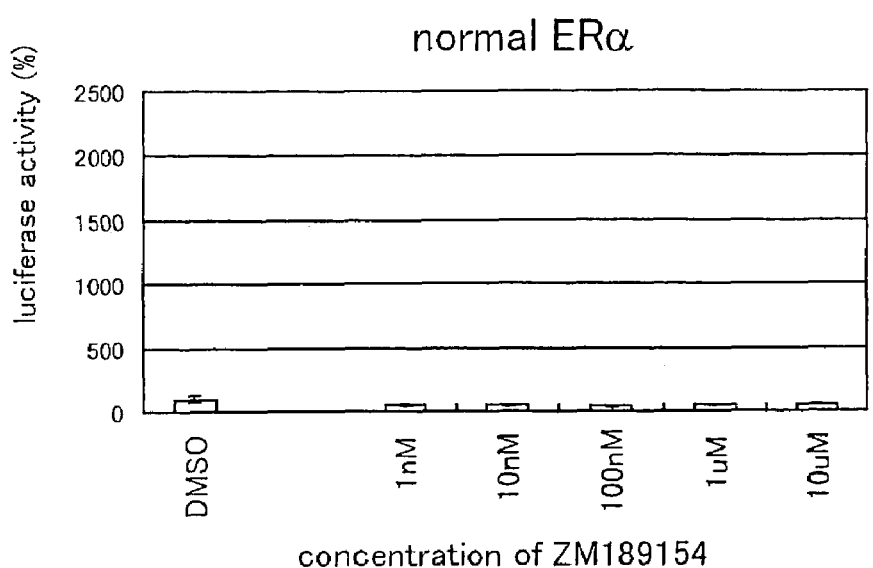
Figure 40:
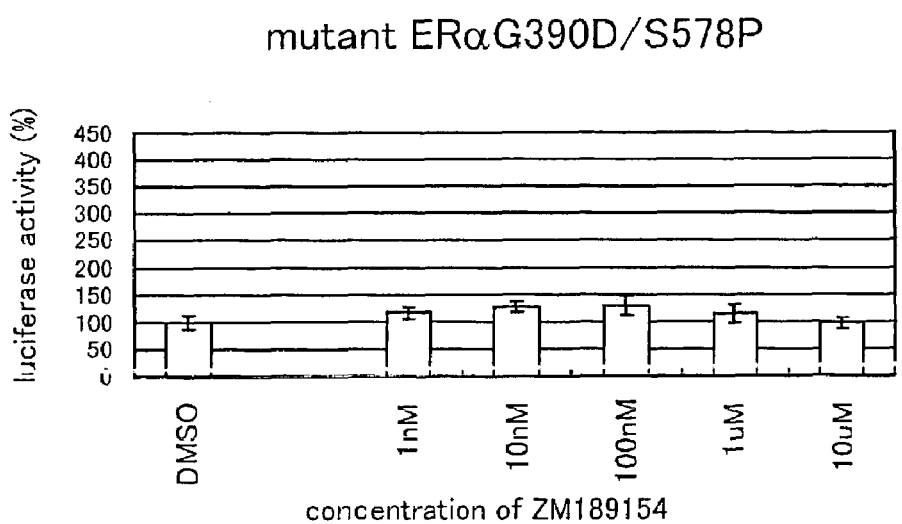
Figure 41:
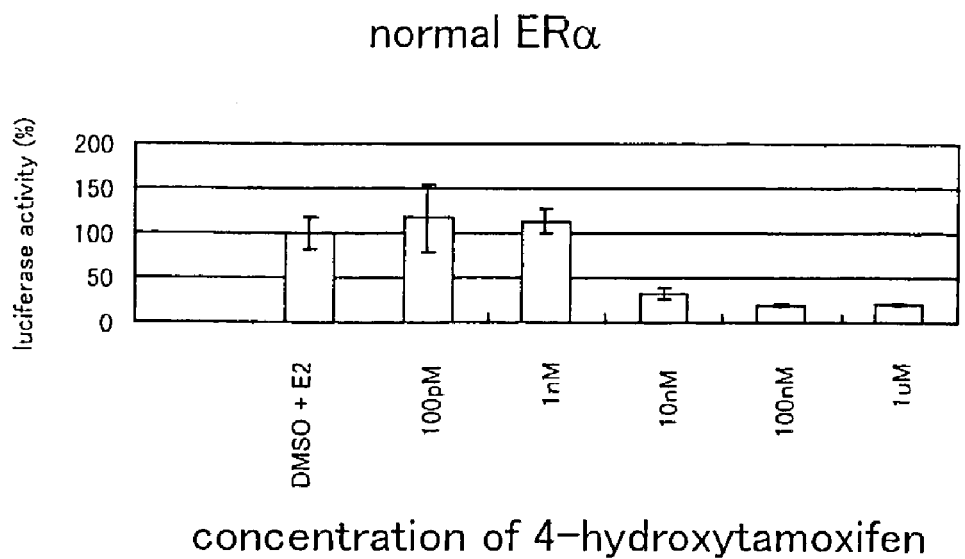
Figure 42:
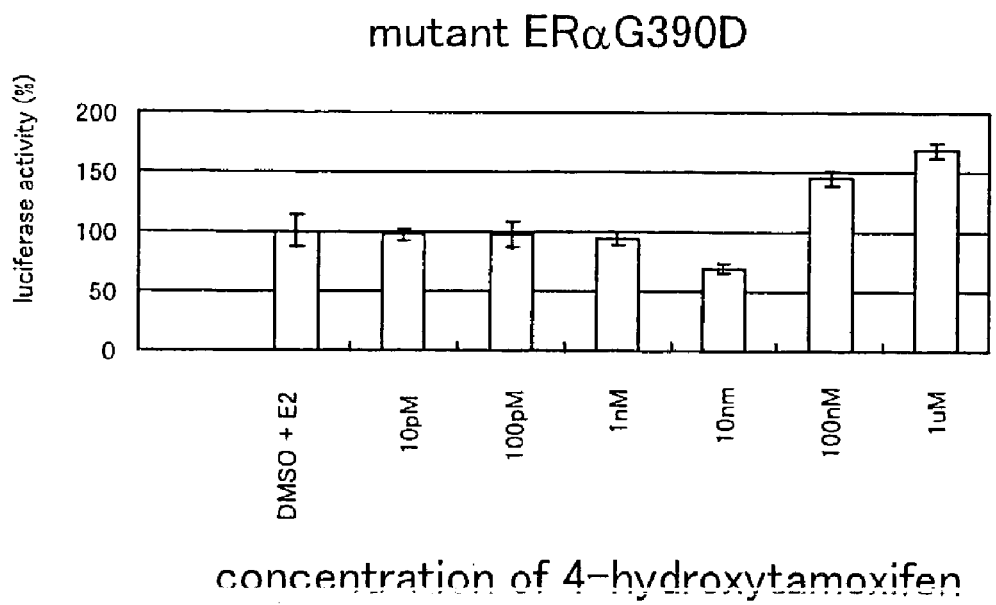
Figure 43:
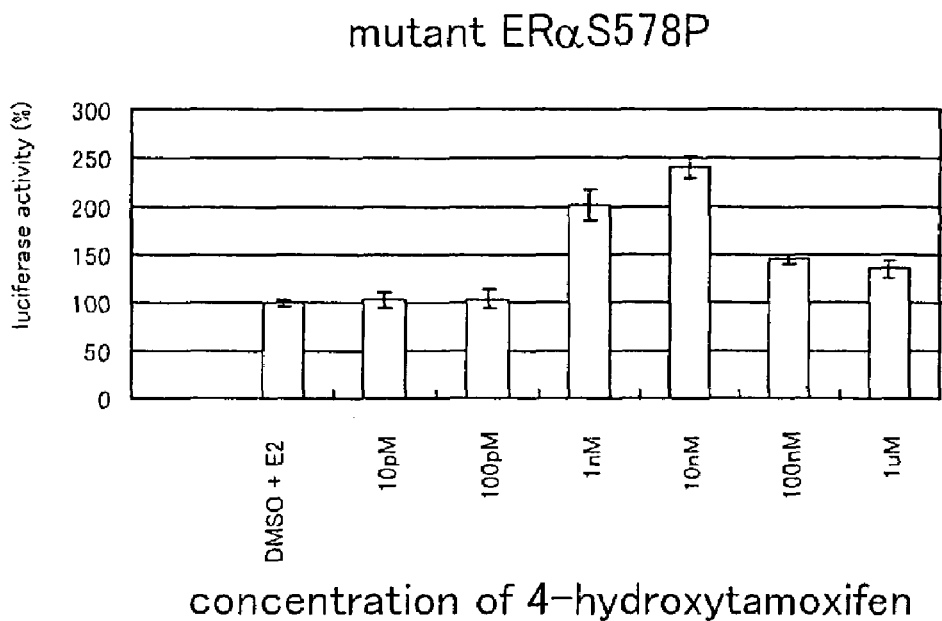
Figure 44:
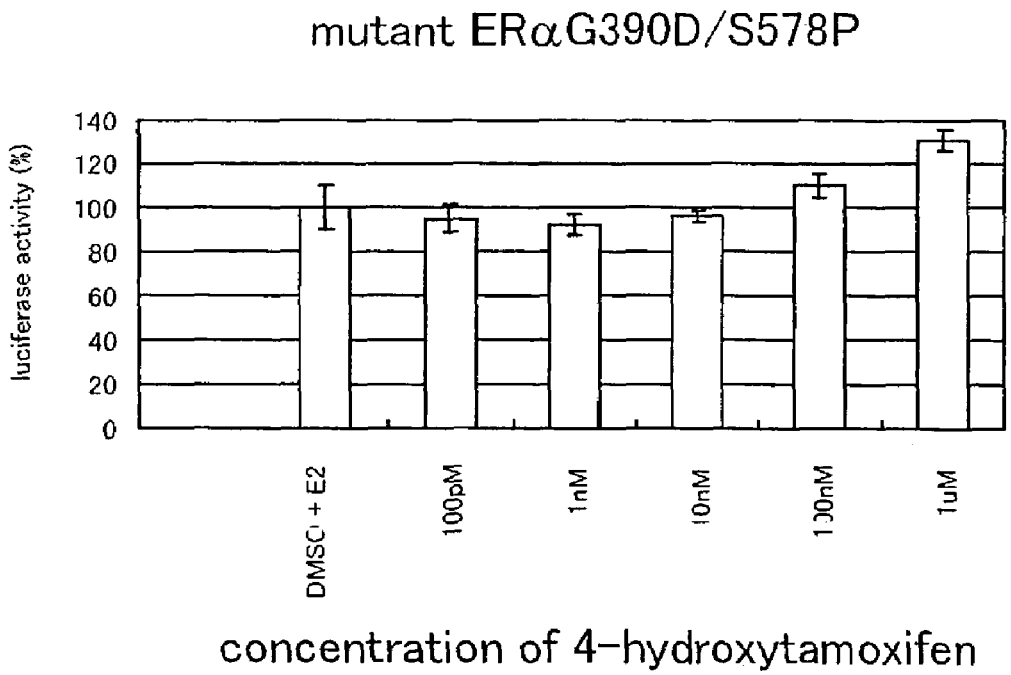
Figure 45:
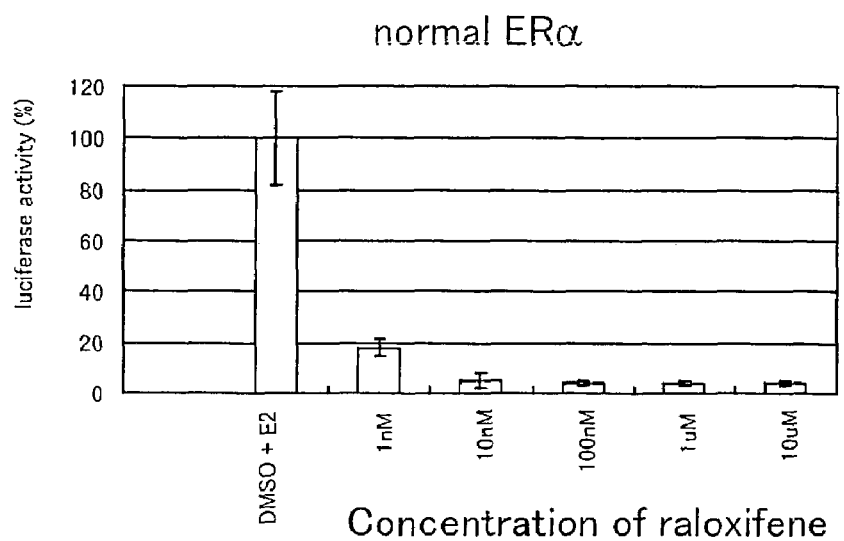
Figure 46:
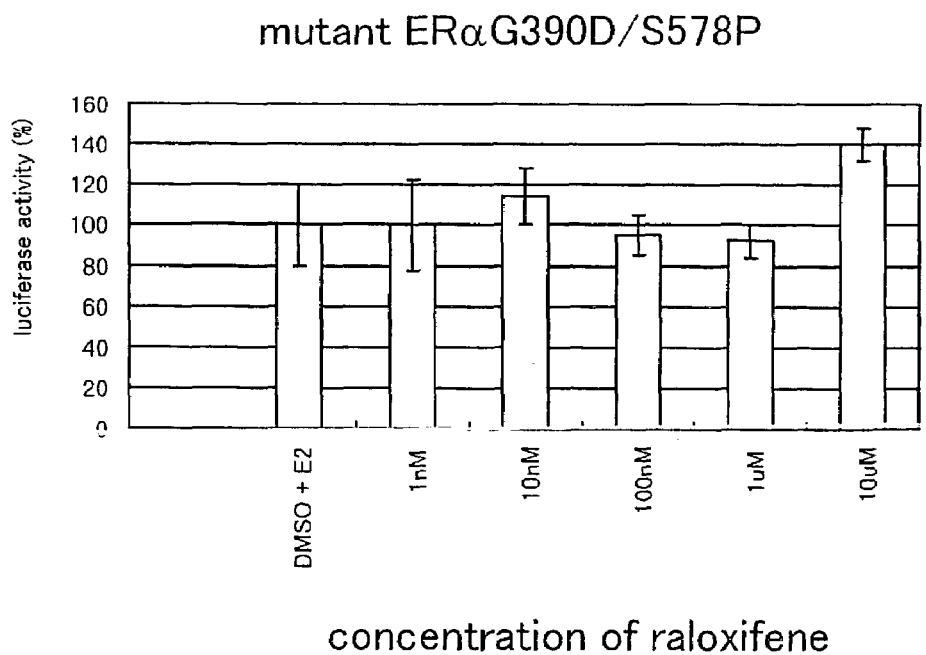
Figure 47:
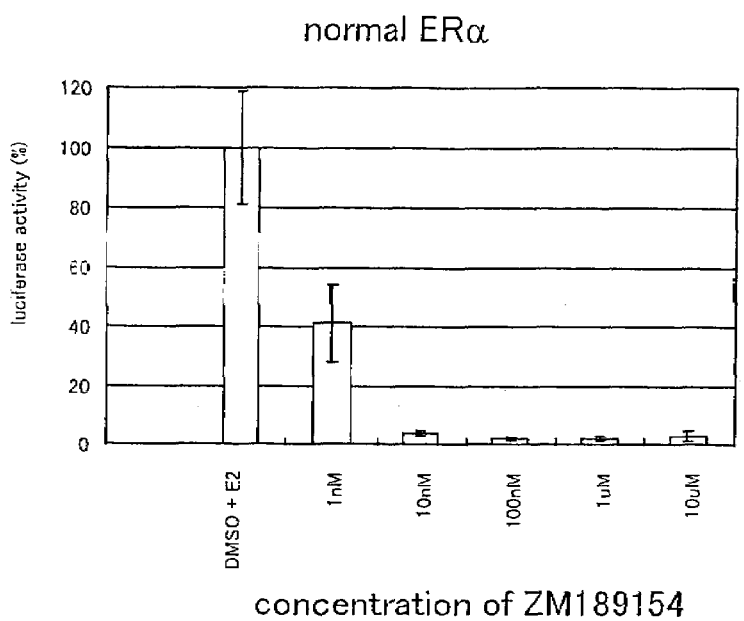
Figure 48:
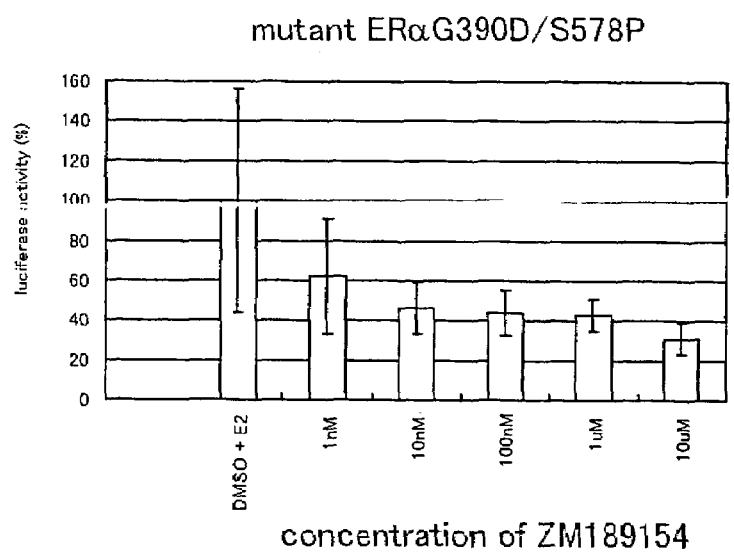

The luciferase activities resulting from the cells prepared in 6.5.1. are illustrated in FIGS. 33 to 48.

FIGS. 33 to 40 illustrate the luciferase activity provided by the human normal ERα, human mutant ERαG390D, human mutant ERαS578P and human mutant ERαG390D/S578P in the presence of 4-hydroxytamoxifen, raloxifene or ZM189154 as the sole probable agent of stimulating the human normal ERα, human mutant ERαG390D, human mutant ERαS578P and human mutant ERαG390D/S578P.

FIGS. 41 to 48 illustrate the luciferase activity provided by the human normal ERα, human mutant ERαG390D, human mutant ERαS578P and human mutant ERαG390D/S578P in the presence of E2 with 4-hydroxytamoxifen, raloxifene or ZM189154.

TABLE 7

|   | utilized plasmid for human normal or mutant ERα | DMSO solution | exposed partial or pure anti-estrogen |
|---|---|---|---|
| 1 | pRC/RSV-hERαKozak | first | 4-hydroxytamoxifen |
| 2 | pRC/RSV-hERαK303R Kozak | first | 4-hydroxytamoxifen |
| 3 | pRC/RSV-hERαKozak | second | ZM189154 |
| 4 | pRC/RSV-hERαK303R Kozak | second | ZM189154 |
| 5 | pRC/RSV-hERαKozak | fourth | ZM189154 |
| 6 | pRC/RSV-hERαK303R Kozak | fourth | ZM189154 |
| 7 | pRC/RSV-hERαKozak | first | 4-hydroxytamoxifen |
| 8 | pRC/RSV-hERαS309F Kozak | first | 4-hydroxytamoxifen |
| 9 | pRC/RSV-hERαKozak | second | ZM189154 |
| 10 | pRC/RSV-hERαS309F Kozak | second | ZM189154 |
| 11 | pRC/RSV-hERαKozak | fourth | ZM189154 |
| 12 | pRC/RSV-hERαS309F Kozak | fourth | ZM189154 |

TABLE 8

|   | utilized plasmid for human normal or mutant ERα | DMSO solution | exposed partial or pure anti-estrogen |
|---|---|---|---|
| 13 | pRC/RSV-hERαKozak | first | 4-hydroxytamoxifen |
| 14 | pRC/RSV-hERαM396V Kozak | first | 4-hydroxytamoxifen |
| 15 | pRC/RSV-hERαKozak | first | raloxifene |
| 16 | pRC/RSV-hERαM396V Kozak | first | raloxifene |
| 17 | pRC/RSV-hERαKozak | third | 4-hydroxytamoxifen |
| 18 | pRC/RSV-hERαM396V Kozak | third | 4-hydroxytamoxifen |
| 19 | pRC/RSV-hERαKozak | third | raloxifene |
| 20 | pRC/RSV-hERαM396V Kozak | third | raloxifene |
| 21 | pRC/RSV-hERαKozak | fourth | ZM189154 |
| 22 | pRC/RSV-hERαM396V Kozak | fourth | ZM189154 |
| 23 | pRC/RSV-hERαKozak | first | 4-hydroxytamoxifen |
| 24 | pRC/RSV-hERαG415V Kozak | first | 4-hydroxytamoxifen |
| 25 | pRC/RSV-hERαKozak | second | ZM189154 |
| 26 | pRC/RSV-hERαG415V Kozak | second | ZM189154 |
| 27 | pRC/RSV-hERαKozak | third | 4-hydroxytamoxifen |
| 28 | pRC/RSV-hERαG415V Kozak | third | 4-hydroxytamoxifen |
| 29 | pRC/RSV-hERαKozak | fourth | ZM189154 |
| 30 | pRC/RSV-hERαG415V Kozak | fourth | ZM189154 |

TABLE 9

|   | utilized plasmid for human normal or mutant ERα | DMSO solution | exposed partial or pure anti-estrogen |
|---|---|---|---|
| 31 | pRC/RSV-hERαKozak | first | 4-hydroxytamoxifen |
| 32 | pRC/RSV-hERαG494V Kozak | first | 4-hydroxytamoxifen |
| 33 | pRC/RSV-hERαKozak | first | raloxifene |
| 34 | pRC/RSV-hERαG494V Kozak | first | raloxifene |
| 35 | pRC/RSV-hERαKozak | third | 4-hydroxytamoxifen |
| 36 | pRC/RSV-hERαG494V Kozak | third | 4-hydroxytamoxifen |
| 37 | pRC/RSV-hERαKozak | third | raloxifene |
| 38 | pRC/RSV-hERαG494V Kozak | third | raloxifene |
| 39 | pRC/RSV-hERαKozak | fourth | ZM189154 |
| 40 | pRC/RSV-hERαG494V Kozak | fourth | ZM189154 |
| 41 | pRC/RSV-hERαKozak | first | 4-hydroxytamoxifen |
| 42 | pRC/RSV-hERαK531E Kozak | first | 4-hydroxytamoxifen |
| 43 | pRC/RSV-hERαKozak | first | raloxifene |
| 44 | pRC/RSV-hERαK531E Kozak | first | raloxifene |
| 45 | pRC/RSV-hERαKozak | second | ZM189154 |
| 46 | pRC/RSV-hERαK531E Kozak | second | ZM189154 |
| 47 | pRC/RSV-hERαKozak | third | 4-hydroxytamoxifen |
| 48 | pRC/RSV-hERαK531E Kozak | third | 4-hydroxytamoxifen |
| 49 | pRC/RSV-hERαKozak | third | raloxifene |
| 50 | pRC/RSV-hERαK531E Kozak | third | raloxifene |
| 51 | pRC/RSV-hERαKozak | fourth | ZM189154 |
| 52 | pRC/RSV-hERαK531E Kozak | fourth | ZM189154 |

TABLE 10

|   | human normal or mutant ERα encoded in the chromosomes | DMSO solution | exposed partial or pure anti-estrogen |
|---|---|---|---|
| 53 | human normal ERα | first | 4-hydroxytamoxifen |
| 54 | human mutant ERαG390D | first | 4-hydroxytamoxifen |
| 55 | human mutant ERαS578P | first | 4-hydroxytamoxifen |
| 56 | human mutant ERαG390D/S578P | first | 4-hydroxytamoxifen |
| 57 | human normal ERα | first | raloxifene |
| 58 | human mutant ERαG390D/S578P | first | raloxifene |
| 59 | human normal ERα | second | ZM189154 |
| 60 | human mutant ERαG390D/S578P | second | ZM189154 |
| 61 | human normal ERα | third | 4-hydroxytamoxifen |
| 62 | human mutant ERα390D | third | 4-hydroxytamoxifen |
| 63 | human mutant ERαS578P | third | 4-hydroxytamoxifen |
| 64 | human mutant ERαG390D/S578P | third | 4-hydroxytamoxifen |
| 65 | human normal ERα | third | raloxifene |
| 66 | human mutant ERαG390D/S578P | third | raloxifene |
| 67 | human normal ERα | fourth | ZM189154 |
| 68 | human mutant ERαG390D/S578P | fourth | ZM189154 |

6.6. Example 6 Comparative Dually Transient Reporter Assay

Approximately $2\times10^6$ HeLa cells were cultured for 1 day using dishes having a diameter of about 10 cm (Falcon) in charcoal dextran FBS/E-MEM medium at 37° C. in the presence of 5% $CO_2$. After culturing the HeLa cells, the HeLa cells were divided into two subcultures.

Subsequently, 3.75 µg of pRc/RSV-hERαKozak and 3.75 µg of pGL3-TATA-EREx5 were introduced into the HeLa cells in the first subculture by a lipofection method using lipofectamine for transient expression. In the second subculture, 3.75 µg of pRc/RSV-hERαK531E Kozak and 3.75 µg of pGL3-TATA-EREx5 were introduced by the lipofection method using lipofectamine for transient expression. The first and second subcultures were then cultured at 37° C. for 16 hours in the presence of 5% $CO_2$. After exchanging the charcoal dextran FBS/E-MEM medium therein with a fresh batch of charcoal dextran FBS/E-MEM medium the first and second subcultures were then similarly cultured for 3 hours. The cells in the first and second subcultures were then collected, respectively, and were uniformly suspended in charcoal dextran FBS/E-MEM medium.

Two (2) general types of DMSO solutions were prepared to expose the cells in the first and second subcultures. The first DMSO solutions were prepared to contain 4-hydroxytamoxifen at various concentrations. The second DMSO solutions were prepared to contain 10 nM of E2 and 4-hydroxytamoxifen at various concentrations.

The first and second DMSO solutions were then nixed, respectively, with the first and second subcultures in 96-well ViewPlates such that the concentration of the first or second DMSO solution in each of the wells was about 0.1% (v/v).

The first and second subcultures were then cultured for 36 hours at 37° C. in the presence of 5% $CO_2$. A 5-fold diluted lysis buffer PGC50 (Nippon Gene) was added, respectively, to the first and second subcultures in the wells at 50 µl per well. The 96-well ViewPlates were periodically and gently shook while being incubated at room temperature for 30 minutes. Ten microliters (10 µl) of the resulting lysed cells were then transferred, respectively, to white 96-well sample plates (Berthold) and were set on a luminometer LB96P (Berthold), which was equipped with an automatic substrate injector. Subsequently, 50 µl of the substrate solution PGL100 (Toyo Ink) was automatically dispensed, respectively, to each of the lysed cells in the white 96-well sample plates to instantaneously measure for 5 seconds the luciferase activity therein with the luminometer LB96P.

The luciferase activity from the dually transient reporter assay are shown in FIGS. 49 to 52.

Figure 49:
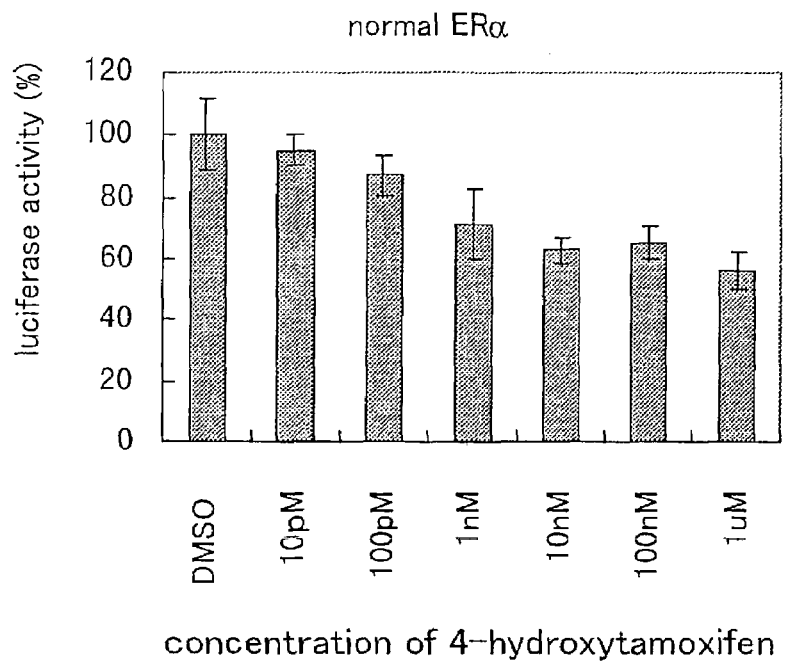
Figure 50:
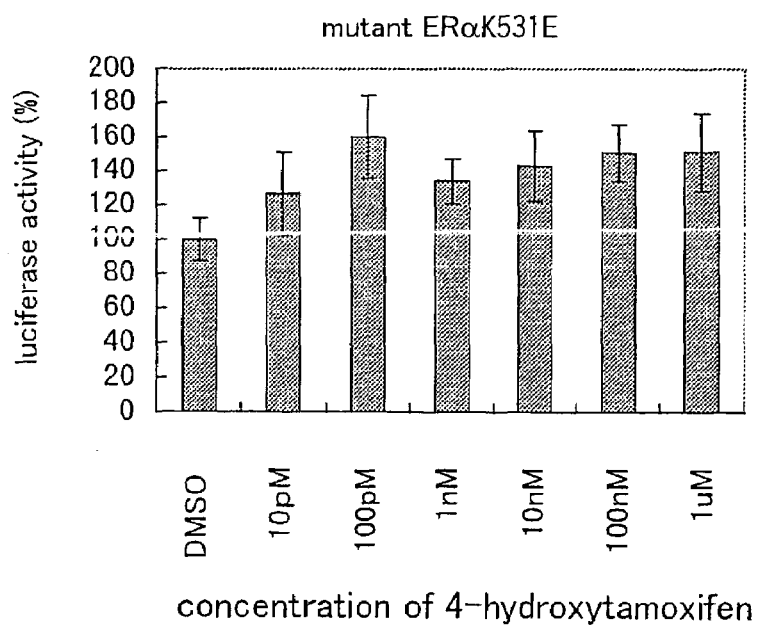

FIGS. 49 and 50 illustrate the luciferase activity provided by the human normal ERα and human mutant ERαK531E in the presence of 4-hydroxytamoxifen as the sole probable agent of stimulating the human normal ERα or human mutant ERαK531E.

Figure 51:
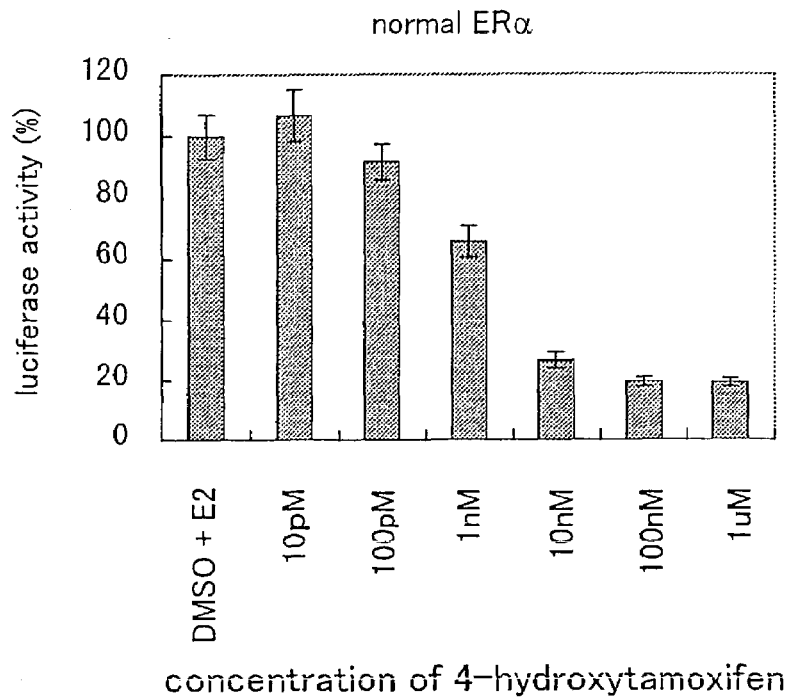
Figure 52:
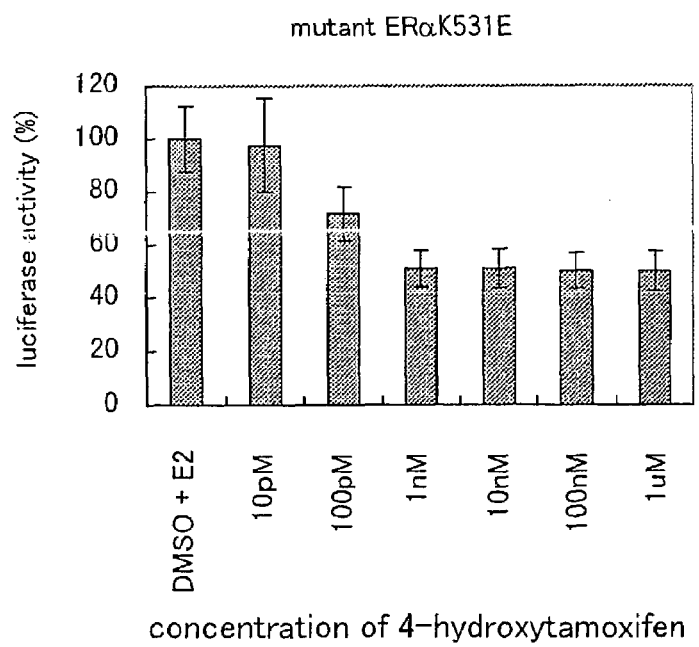

FIGS. 51 and 52 illustrate, respectively, the luciferase activity of mutant human normal ERα and human mutant ERαK531E in the presence of E2 with 4-hydroxytamoxifen.

6.7. Example 7 Search Oligonucleotides

In order to search for a variant codon that encodes a substituted amino acid in a human test ERα, search oligonucleotides are designed so that the search oligonucleotides can anneal to a searching region in a human test ERα gene when the human test ERα gene encodes a human normal ERα. The searching regions include the codon encoding the amino acid at relative position 303, the codon encoding the amino acid at relative position 309, the codon encoding the amino acid at relative position 390, the codon encoding the amino acid at relative position 396, the codon encoding the amino acid at relative position 415, the codon encoding the amino acid at relative position 494, the codon encoding the amino acid at relative position 531 or the codon encoding the amino acid at relative position 578. Further the oligonucleotides are designed to have a GC content of from 30% to 70% and a size of 20 bp. Based on the oligonucleotides so designed, the oligonucleotides of the present invention indicated by the above are synthesized with a DNA synthesizer (Model 394, Applied Biosystems).

6.8 Example 8 Genotype Diagnosis by PCR Amplification and Nucleotide Sequencing Methods A test human liver tissue sample is used to diagnose the genotype of the test ERα polynucleotide therein. In utilizing the test human liver tissue sample, 0.1 g of the test human liver tissue sample is homogenized with a homogenizer in 5 ml of a buffer containing 4M guanidium thiocyanate, 0.1M Tris-HCl (pH 7.5) and 1% β mercaptoethanol. The resulting buffer is layered with 25 ml of an aqueous 5.7M CsCl solution and is ultracentrifuged at 90,000×g for 24 hours to obtain a RNA pellet. After rinsing the RNA pellet with 70% ethanol, the RNA pellet is allowed to air dry at room temperature. The RNA pellet is then dissolved in 10 μl of sterile water to a concentration of 1.2 μg/ml. A solution of test cDNAs is then produced by collectively using the RNAs in the RNA solution as a template in a reverse transcription reaction. In producing the test cDNAs, Superscript II (Gibco) was used with 1 μl of the RNA solution, oligo-dT oligonucleotides (Amerscham-Pharmacia) and the buffer provided with the oligo-dT oligonucleotides. The reverse transcription reaction was allowed to react for 1 hour at 37° C.

Using 1/50 by volume samples of the test cDNAs, a PCR amplification is conducted with combinations of the search oligonucleotides shown in Table 11 below.

TABLE 11

| | Search Oligonucleotides |
|---|---|
| 1 | SEQ ID: 32 and SEQ ID: 38 |
| 2 | SEQ ID: 42 and SEQ ID: 48 |

TABLE 11-continued

| | Search Oligonucleotides |
|---|---|
| 3 | SEQ ID: 52 and SEQ ID: 58 |
| 4 | SEQ ID: 62 and SEQ ID: 68 |
| 5 | SEQ ID: 72 and SEQ ID: 78 |
| 6 | SEQ ID: 82 and SEQ ID: 88 |
| 7 | SEQ ID: 92 and SEQ ID: 98 |
| 8 | SEQ ID: 109 and SEQ ID: 110 |

The PCR mixtures in these PCR amplifications contain the test cDNAs, AmpliTaq DNA polymerase (Perkin Elmer), 100 μM of dNTPs (dATP, dTTP, dGTP, dCTP), one of the combinations of the search oligonucleotides and the buffer provided with the AmpliTaq Polymerase. In this PCR amplification, there are repeated 35 times for each of the PCR amplifications, an incubation cycle entailing an incubation at 95° C. for 1 minute, then an incubation at 55° C. for 30 sec, which is followed by an incubation at 72° C. for 1 minute. The obtained searching region polynucleotides are subjected to 1% low melting point agarose gel electrophoresis (Agarose L, Nippon Gene) and are recovered. Using whole amounts of the recovered searching region polynucleotides, the searching regions are sequenced. The nucleotide sequences of the searching regions are compared to the nucleotide sequence encoding human normal ERα.

6.9. Example 9 Genotype Diagnosis by SSCP Methods

6.9.1. Extraction of Test Genomic DNAs from a Test Tissue Sample

Test genomic DNAs from a test tissue sample is prepared by the methods described in TAKARA PCR Technical news No. 2, Takara Shuzo (September 1991). This procedure in relation with the present invention is described below.

Two (2) to 3 hair samples from a test subject are washed with sterile water and then 100% ethanol. After air drying the hair samples, the hair samples are cut to 2 to 3 mm and are transferred to a plastic test tube. Two hundred microliters (200 μl) of BCL buffer (10 mM Tris-HCl (pH. 7.5), 5 mM MgCl$_2$, 0.32M sucrose, 1% Triton X-100) are added thereto. Subsequently, a Proteinase K solution and a SDS solution are mixed therewith to amount to 100 μg/ml and 0.5% (w/v), respectively.

After incubating the resulting mixture for 1 hour at 70° C., the mixture is phenol-chloroform extracted to recover the aqueous layer therefrom. In the phenol-chloroform extraction, a substantially equal volume of phenol-chloroform is added to the mixture. The mixture is shaken vigorously and is centrifuged (15,000 rpm, 20,000×g, 5 min, 4° C.). The aqueous layer therefrom is extracted with a pipette so that the phenol layer is not disturbed. A second phenol-chloroform extraction is then similarly conducted with the aqueous layer.

A substantially equal volume of chloroform is mixed with the aqueous layer from the second phenol-chloroform extraction, to extract the aqueous layer from the resulting chloroform mixture. In this extraction with chloroform, the chloroform mixture is shaken vigorously and is centrifuged, so that the aqueous layer can be extracted from the chloroform mixture. Five hundred microliters (500 μl) of 100% ethanol is then added to the aqueous layer from the chloroform mixture. The test genomic DNAs therein is precipitated at −80° C. for 20 minutes and is then centrifuged to obtain a pellet of the test genomic DNAs. The obtained pellet of the test genomic DNAs is dried and dissolved in sterile water, to so that test genomic DNAs can provide a test ERα polynucleotide.

Alternatively, peripheral blood can be used as a test sample from which test genomic DNAs can be obtained. Ten milliliters (10 ml) of blood is collected from a test subject and test genomic DNAs are extracted from the blood, using a DNA Extraction kit (Stratagene).

6.9.2. Analysis of Test Genomic DNA by the PCR-SSCP Method

Combinations of a forward search oligonucleotide and a reverse search oligonucleotide are selected for PCR amplifications with the test genomic DNAs. The combinations of the forward and reverse search oligonucleotide are selected, based on the locus of the searching regions in the test ERα polynucleotide. The combinations of the forward and reverse search oligonucleotides in connection with the searching regions which are suspected to contain the valiant codon encoding a substituted amino acid at the provided relative positions are shown in Table 12 below.

TABLE 12

| searching region | Forward search oligonucleotide | Reverse search oligonucleotide |
|---|---|---|
| relative position 303 | SEQ ID: 29, SEQ ID: 30, SEQ ID: 31, SEQ ID: 32 or SEQ ID: 33 | SEQ ID: 34, SEQ ID: 35, SEQ ID: 36, SEQ ID: 37 or SEQ ID: 38 |
| relative position 309 | SEQ ID: 39, SEQ ID: 40, SEQ ID: 41, SEQ ID: 42 or SEQ ID: 43 | SEQ ID: 44, SEQ ID: 45, SEQ ID: 46, SEQ ID: 47 or SEQ ID: 48 |
| relative position 390 | SEQ ID: 49, SEQ ID: 50, SEQ ID: 51, SEQ ID: 52 or SEQ ID: 53 | SEQ ID: 54, SEQ ID: 55, SEQ ID: 56, SEQ ID: 57 or SEQ ID: 58 |
| relative position 396 | SEQ ID: 59, SEQ ID: 60, SEQ ID: 61, SEQ ID: 62 or SEQ ID: 63 | SEQ ID: 64, SEQ ID: 65, SEQ ID: 66, SEQ ID: 67 or SEQ ID: 68 |
| relative position 415 | SEQ ID: 69, SEQ ID: 70, SEQ ID: 71, SEQ ID: 72 or SEQ ID: 73 | SEQ ID: 74, SEQ ID: 75, SEQ ID: 76, SEQ ID: 77 or SEQ ID: 78 |
| relative position 494 | SEQ ID: 79, SEQ ID: 80, SEQ ID: 81, SEQ ID: 82 or SEQ ID: 83 | SEQ ID: 84, SEQ ID: 85, SEQ ID: 86, SEQ ID: 87 or SEQ ID: 88 |
| relative position 531 | SEQ ID: 89, SEQ ID: 90, SEQ ID: 91, SEQ ID: 92 or SEQ ID: 93 | SEQ ID: 94, SEQ ID: 95, SEQ ID: 96, SEQ ID: 97 or SEQ ID: 98 |
| relative position 578 | SEQ ID: 99, SEQ ID: 100, SEQ ID: 101, SEQ ID: 102 or SEQ ID: 103 | SEQ ID: 104, SEQ ID: 105, SEQ ID: 106, SEQ ID: 107 or SEQ ID: 108 |

The combinations of the forward and reverse search oligonucleotides are synthesized with a DNA synthesizer. Each of the forward and reverse search oligonucleotides are labeled with $^{32}P$ using a DNA MEGALABEL kit (Takara Shuzo). The test genomic DNAs are then used, respectively, in the PCR amplifications to provide amplified searching region polynucleotides. Each of the PCR mixtures in these PCR amplifications contain Amplitaq DNA Polymerase (Perkin Elmer), 400 μM of dNTPs (100 μM of dATP, 100 μM of dTTP, 100 μM of dGTP and 100 μM of dCTP), 100 pmol of the $^{32}P$ labeled forward search oligonucleotide, 100 pmol of the $^{32}P$ labeled reverse search oligonucleotide, 1 μg of the test genomic DNA and the buffer provided with the Amplitaq DNA Polymerase. In each of these PCR amplifications, there are repeated 35 times for each of the PCR amplifications, an incubation cycle entailing an incubation at 94° C. for 1 minute, then an incubation at 55° C. for 30 seconds, which is followed by an incubation at 72° C. for 1 minute.

After the PCR amplifications, 1/20 by volume samples from each of the amplified searching region polynucleotides are heat denatured in 80% formamide at 80° C. for 5 minutes. Subsequently, each the heat denatured searching region polynucleotides are subjected to electrophoresis in 5% native polyacrylamide gels using 180 mM Tris-borate buffer (pH 8.0). The conditions for electrophoresis include a room temperature air cooling and a constant power of 40 W for 60 min. After electrophoresis, the 5% native polyacrylamide gels are autoradiographed using X-ray films by using conventional procedures to detect the radioactivity of the searching regions.

Since a product encoding the valiant codon has a different mobility in the 5% native polyacrylamide gel as compared with a product encoding a normal codon, a comparison of each of the mobilities of the searching region polynucleotides with a standard polynucleotide encoding a corresponding region in a human normal ERα detects the presence or absence of a mutation in the searching regions.

6.9.3. Determination of Mutation

After detecting a variant codon in the searching regions, 1 mm square portions containing the searching region polynucleotides are cut out of the 5% native polyacrylamide gels. Each of the 1 mm square portions are treated at 90° C. for 10 min in 100 μl of sterile water to recover the searching region polynucleotides from the 1 mm square portions. Subsequently, 1/20 by volume samples of the searching region polynucleotides are then used, respectively, in a second round of PCR amplifications. The oligonucleotides in these PCR amplifications used the combinations of the search oligonucleotides used in the above 6.9.2. Each of the PCR mixtures in these PCR amplifications contain Amplitaq DNA Polymerase (ABI), 400 μM of dNTPs (100 μM of dATP, 100 μM of dTTP, 100 μM of dGTP and 100 μM of dCTP), the forward search oligonucleotide, the reverse search oligonucleotide, one of the test DNA fragments and the buffer provided with the Amplitaq DNA polymerase. In each of these PCR amplifications, there are repeated 35 times, an incubation cycle entailing an incubation at 94° C. for 1 minute, then an incubation at 55° C. for 30 seconds, which is followed by an incubation at 72° C. for 1 minute.

After completion of the reaction, the amplified searching region polynucleotides are subjected to low melting point agarose gel electrophoresis (Agarose L: Nippon Gene). After recovering the amplified searching region polynucleotides from the low melting point agarose gels, the recovered searching region polynucleotides are prepared with a Dye Terminator cycle sequence ready reaction kit (Applied Biosystems). The prepared sample of the searching region polynucleotides are sequenced, respectively, with an ABI autosequencer (Model 377, Applied Biosystems), to determine the mutation in the valiant codons, if present, in the searching regions.

6.10. Example 10 Genotype Diagnosis by RFLP Methods

Combinations of a forward search oligonucleotide and a reverse search oligonucleotide are selected for PCR amplifications with test genomic DNAs or a test cDNAs. The combinations of the forward and reverse search oligonucleotides are selected, based on the locus of the searching regions in the test ERα polynucleotide. The combinations of the forward and reverse search oligonucleotides are shown in Table 13 below, in connection with the searching regions which are suspected to contain a variant codon encoding a substituted amino acid at the provided relative positions in Table 13 below.

TABLE 13

| Searching region | oligonucleotides |
|---|---|
| Relative position 303 | SEQ ID: 164 and SEQ ID: 165 |
| Relative position 309 | SEQ ID: 166 and SEQ ID: 167 |
| Relative position 396 | SEQ ID: 168 and SEQ ID: 169 |
| Relative position 415 | SEQ ID: 170 and SEQ ID: 171 |
| Relative position 494 | SEQ ID: 172 and SEQ ID: 173 |
| Relative position 531 | SEQ ID: 174 and SEQ ID: 175 |

The test genomic DNAs or test cDNAs are used in the PCR amplifications to provide amplified searching region polynucleotides having a size of about 100 or 160 bp. Each of the PCR mixtures in these PCR amplifications contain Amplitaq DNA Polymerase (ABI), the test genomic DNAs or test cDNAs, dNTPs (dATP, dTTP, dGTP and dCTP), the forward search oligonucleotide, the reverse search oligonucleotide and the buffer provided with the Amplitaq DNA Polymerase. In each of these PCR amplifications, there are repeated 35 times, an incubation cycle entailing an incubation at 94° C. for 1 minute, then an incubation at 55° C. for 30 seconds, which is followed by an incubation at 72° C. for 1 minute.

Samples of each of the searching region polynucleotides are then mixed, respectively, with various restriction enzymes for restriction digestion reactions (one restriction enzyme per restriction digestion reaction) and are incubated at 37° C. at 1 hour. The restriction digestion reaction mixtures are subjected to agarose gel electrophoresis to confirm whether the searching region polynucleotides are successfully restriction digested with one of the various restriction enzymes. A successful restriction digest with the restriction enzymes shown in Table 14 and Table 15 below indicate whether there is in the searching region, a valiant codon encoding a substituted amino acid at the provided relative position in Table 14 and Table 15 below

TABLE 14

|  | relative position 309 | relative position 494 |
|---|---|---|
| restriction enzyme approximate length of searching region when encoding normal codon | Apa I 100 bp | Stu I 150 bp |
| restriction digestion approximate length of resulting DNA fragments | yes 40 bp/60 bp | yes 100 bp/50 bp |

In reference to Table 14, an unsuccessful restriction digestion with the provided restriction enzyme at the codon encoding the amino acid at the provided relative position, indicates that such a codon is a valiant codon. In such cases, the searching regions are sequenced with an ABI autosequencer (Model 377, Applied Biosystems) to determine the mutation in the variant codons, if present, in the searching regions.

TABLE 15

|  | relative position 303 | relative position 396 | relative position 415 | relative position 531 |
|---|---|---|---|---|
| restriction enzyme: approximate length of searching region: when encoding normal codon | Stu I 100 bp | ApaL I 100 bp | Kpn I 100 bp | Sac I 100 bp |
| restriction digestion approximate length of resulting DNA fragments: when encoding variant codon | no — | no — | no — | no — |
| when variant codon sequence is: restriction digestion: approximate length of resulting DNA fragments: | AGG yes 40 bo/ 60 bp | GTG yes 40 bo/ 60 bp | GTA yes 40 bo/ 60 bp | GAG yes 40 bo/ 60 bp |

In reference to Table 15, a successful restriction digestion with the provided restriction enzyme at the codon encoding the amino acid at the provided relative position, indicates that such a codon is a valiant codon. In such cases, it is determined that the mutations in the variant codons, if present, are the nucleotide sequences provided in the above Table 15.

6.11. Example 11 Genotype Diagnosis by Southern Hybridization Methods

Five micrograms (5 µg) of test genomic DNA, provided in 6.9.1., is thoroughly restriction digested with the restriction enzyme Stu I. The restriction digestion reaction mixture is subjected to electrophoresis at 20V for 16 hours with a 4% Nusieve 3:1 agarose gel (FMC BIO). The capillary alkali blotting method (Hybond blotting membrane manual, Amerscham) is used to blot for 2 hours a nylon membrane with the separated DNA fragments in the 4% Nuseive 3:1 agarose gel to the nylon membrane. Followed by lightly washing the blotted filter with 2×SSC buffer (0.3M NaCl, 0.33M Na-Citrate, pH 7.0), the blotted nylon membrane is dried at 80° C. for 90 minutes.

The blotted nylon membrane is treated at 55° C. for 16 hours with prehybridization buffer (6×SSPE (0.9M NaCl, 0.052M $NaH_2PO_4$, 7.5 mM EDTA), 0.5% SDS, 5×Denhart and 0.1 mg/ml of salmon sperm DNA). The prehybridization buffer is then exchanged with an equal volume of hybridization buffer (6×SSPE (0.9M NaCl, 0.052M $NaH_2PO_4$, 7.5 mM EDTA), 0.5% SDS, 5×Denhart, 0.1 mg/ml of salmon sperm DNA and a $^{32}P$ labeled probe oligonucleotide). In the hybridization buffer, the radioactive concentration of the $^{32}P$ labeled probe oligonucleotide is at least $10 \times 10^8$ cpm for every 150 ml of the hybridization buffer. As the $^{32}P$ labeled probe oligonucleotide, there is utilized the oligonucleotide depicted in SEQ ID:81 which is labeled with $^{32}P$ at the ends thereof. The $^{32}P$ labeled probe is produced by incubating at 37° C. for 1 hour with γ $^{32}P$-ATP, T4 polynucleotide kinase and 1 µg of the oligonucleotide depicted in SEQ ID:81 in the buffer provided with the T4 polynucleotide kinase.

After the hybridization, the blotted nylon membrane is washed twice with washing buffer containing 1×SSC (0.15 M NaCl, 15 mM sodium citrate) and 0.5% SDS. In washing the blotting filter twice, the blotted nylon membrane is incubated after each washing at 62° C. for 40 minutes in the washing buffer.

The blotted membrane is then autoradiographed for 10 days with x-ray film to analyze whether the restriction enzyme Stu I is successful in restriction digesting at the restriction site therein overlapping with the codon in the searching region which is suspected to be a variant codon encoding a substituted amino acid at relative position 494. A successful restriction digest with the restriction enzyme Stu I indicates that there is in the test ERα polynucleotide, a nucleotide sequence encompassing AGGCCT, overlapping with the codon encoding the amino acid at relative position 494. In such cases, it is determined that the test ERα is a normal ERα. An unsuccessful restriction digest with the restriction enzyme Stu I at the corresponding locus, indicates that there is in the test ERα polynucleotide, a variant codon encoding a substituted amino acid at relative position 494. In such cases, the searching region is sequenced with an ABI autosequencer (Model 377, Applied Biosystems), to determine the mutation in the variant codon, if present, in the searching region.

6.12. Example 12 Production of a Plasmid Encoding Human Normal AR

A human prostate cDNA library (CLONETECH, Quick clone cDNA#7123-1) is utilized to PCR amplify therefrom a cDNA encoding a human normal AR (Genbank Accession No. M23263). The PCR mixture in this PCR amplification contains 10 ng of the human prostate cDNA library, 10 pmol of an oligonucleotide depicted in SEQ ID:176, 10 pmol of an oligonucleotide depicted in SEQ ID:177, LA-Taq Polymerase (Takara Shuzo), the buffer provided with the LA-Taq Polymerase and dNTPs (dATP, dTTP, dGTP, dCTP). The oligonucleotides depicted in SEQ ID:176 and SEQ ID:177 are synthesized with a DNA synthesizer (Model 394, Applied Biosystems,). In this PCR amplification, there is repeated 35 times with a PCRsystem 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm with ethidium bromide staining, that the cDNA encoding the human normal AR is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the stair codon (ATG) in the cDNA. The PCR mixture in this PCR amplification contains 100 ng of the cDNA encoding the human normal AR, an oligonucleotide depicted in SEQ ID:178 and an oligonucleotide depicted in SEQ ID:179, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L: Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends thereof. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is then treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids is then prepared with a Dye Terminator Sequence Kit FS (Applied Biosystems). The isolated plasmids are sequenced with an ABI autosequencer (Model 377, Applied Biosystems), to confirm that there is a plasmid encoding the human normal AR. Such a plasmid is selected and is designated as pRc/RSV-hAR Kozak.

6.13. Example 13 Production of a Plasmid Encoding a Human Normal GR

A human liver cDNA library (CLONETECH, Quick clone cDNA#7113-1) is utilized to PCR amplify therefrom a cDNA encoding a normal GR (Genbank Accession No. M10901). The PCR mixture in this PCR amplification contains 10 ng of the human liver cDNA library, 10 pmol of an oligonucleotide depicted in SEQ ID:180, 10 pmol of an oligonucleotide depicted in SEQ ID:181, LA-Taq Polymerase (Takara Shuzo), the buffer provided with the LA-Taq Polymerase and dNTPs (dATP, dTTP, dGTP, dCTP). The oligonucleotides depicted in SEQ ID:180 and SEQ ID:181 are synthesized with a DNA synthesizer (Model 394, Applied Biosystems). In this PCR amplification, there is repeated 35 times with a PCRsystem 9700 (Applied Biosystems), an incubation cycle entailing an incubation at 95° C. for 1 minute followed by an incubation at 60° C. for 3 minutes.

The resulting PCR mixture is subjected to low melting point agarose gel electrophoresis (Agarose L: Nippon Gene) to confirm with ethidium bromide staining, that the cDNA encoding the human normal GR is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA encoding the human normal GR, an oligonucleotide depicted in SEQ ID:182 and an oligonucleotide depicted in SEQ ID:183, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 60° C. for 3 minutes. The resulting PCR mixture is subjected to low melting point agarose gel electrophoresis (Agarose L: Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The reaction mixture is used to transform *E. coli* competent DH5α cells (TOYOBO). The transformed *E. coli* cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding the normal GR. The plasmid is selected and is designated as pRc/RSV-hGR Kozak.

6.14. Example 14 Production of a Plasmid Encoding a Human Normal PR

A human liver cDNA library (CLONETECH, Quick clone cDNA#7113-1) is utilized to PCR amplify therefrom a cDNA encoding a normal PR (Genbank Accession No. M15716). The PCR mixture in this PCR amplification contains 10 ng of the human liver cDNA library, 10 pmol of a oligonucleotide depicted in SEQ ID:184, 10 pmol of a oligonucleotide depicted in SEQ ID:185, LA-Taq Polymerase (Takara Shuzo), the buffer provided with the LA-Taq Polymerase and dNTPs (dATP, dTTP, dGTP, dCTP). The oligonucleotides depicted in SEQ ID:184 and SEQ ID:185 are synthesized with a DNA synthesizer (Model 394, Applied Biosystems). In this PCR amplification, there is repeated 35 times with a PCRsystem 9700 (Applied Biosystems), an incubation cycle entailing an incubation at 95° C. for 1 minute followed by an incubation at 55° C. for 3 minutes.

The resulting PCR mixture is subjected to low melting point agarose gel electrophoresis (Agarose L: Nippon Gene) to confirm with ethidium bromide staining, that the cDNA encoding human normal PR is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA encoding normal PR, a oligonucleotide depicted in SEQ ID:186 and a oligonucleotide depicted in SEQ ID:187, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 55° C. for 3 minutes. The resulting PCR mixture is subjected to low melting point agarose gel electrophoresis (Agarose L: Nippon Gene). After recovering the amplified test cDNA from the low melting point agarose gel, 1 µg of the amplified test cDNA is treated with a DNA Blunting Kit (Takara Shuzo) to blunt the ends of the amplified test cDNA. Subsequently, the resulting test cDNA therefrom is allowed to react with a T4 polynucleotide kinase to phosphorylate the ends of the cDNA. After phenol treating the phosphorylated test cDNA, the phosphorylated test cDNA is ethanol precipitated to achieve a purified form of the phosphorylated test cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated test cDNA are used in a ligation reaction with a T4 DNA ligase. The ligation reaction mixture is used to transform *E. coli* competent DH5α cells (TOYOBO). The transformed *E. coli* cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding normal PR. Such a plasmid is selected and is designated as pRc/RSV-hPR Kozak.

6.15. Example 15 Production of a Plasmid Encoding a Human Normal MR

A human liver cDNA library (CLONETECH, Quick clone cDNA#7113-1) is utilized to PCR amplify therefrom a cDNA encoding a normal MR (Genbank Accession No. M16801). The PCR mixture in this PCR amplification contains 10 ng of the human liver cDNA library, 10 pmol of an oligonucleotide depicted in SEQ ID:188, 10 pmol of an oligonucleotide depicted in SEQ ID:189, LA-Taq Polymerase (Takara Shuzo), the buffer provided with the LA-Taq Polymerase and dNTPs (dATP, dTTP, dGTP, dCTP). The oligonucleotides depicted in SEQ ID:188 and SEQ ID:189 are synthesized with a DNA synthesizer (Model 394, Applied Biosystems). In this PCR amplification, there is repeated 35 times with a PCRsystem 9700 (Applied Biosystems), an incubation cycle entailing an incubation at 95° C. for 1 minute followed by an incubation at 60° C. for 3 minutes.

The resulting PCR mixture is subjected to low melting point agarose gel electrophoresis (Agarose L: Nippon Gene) to confirm with ethidium bromide staining, that the cDNA encoding the normal MR is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA encoding the normal MR, a oligonucleotide depicted in SEQ ID:190 and a oligonucleotide depicted in SEQ ID:191, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 60° C. for 3 minutes. The resulting PCR mixture is subjected to low melting point agarose gel electrophoresis (Agarose L: Nippon Gene). After recovering the amplified cDNA from the low melting point agarose gel, 1 µg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding normal MR. The plasmid is selected and is designated as pRc/RSV-hMR Kozak.

6.16. Example 16 Production of a Stably Transformed Cell which Stably Contains in One of its Chromosomes the MMTV Reporter Gene The plasmid pMSG (Pharmacia) is restriction digested with restriction enzymes Hind III and Sma I to provide a DNA fragment encoding a partial sequence of the MMTV-LTR region, which has a size of 1463 bp. The 1463 bp DNA fragment is then treated with a DNA Blunting Kit (Takara Shuzo) to blunt the ends of the 1463 bp DNA fragment.

The plasmid pGL3 (Promega), which encodes the firefly luciferase gene, is restriction digested with restriction enzymes Bgl II and Hind III and is then treated with BAP at 65° C. for 1 hour. The restriction digestion reaction mixture is then subjected to low melting point agarose gel electrophoresis (Agarose L, Nippon Gene) to confirm that there is a DNA fragment having a nucleotide sequence encoding the firefly luciferase. The DNA fragment having the nucleotide sequence encoding the firefly luciferase is then recovered from the low melting point agarose gel. Subsequently, 100 ng of the recovered DNA fragment have the nucleotide sequence encoding firefly luciferase and 1 µg of the 1463 bp DNA fragment are used in a ligation reaction with T4 DNA ligase. The ligation reaction mixture is then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then restriction digested with restriction enzymes Kpn I and Cla I. The restriction digestion reaction mixtures are subjected to agarose gel electrophoresis to confirm that there is a plasmid which contains 1 copy of the 1463 bp DNA fragment operably upstream from the DNA fragment have the nucleotide sequence encoding firefly luciferase (hereinafter referred to as the MMTV reporter gene). Such a plasmid is selected and is designated as pGL3-MMTV.

The plasmid pUCSV-BSD (Funakoshi) is restriction digested with restriction enzyme BamH I to prepare a DNA encoding a blasticidin S deaminase gene expression cassette. Further, the plasmid pGL3-MMTV is restriction digested with restriction enzyme BamH I and is then treated with BAP at 65° C. for 1 hour. The resulting DNA encoding the blasticidin S deaminase gene expression cassette and the restriction digested pGL3-MMTV are mixed together to be used in a ligation reaction with T4 DNA ligase. The ligation reaction mixture is used to transform E. coli competent DH5α cells. The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems) to confirm there is a plasmid which has a structure in which the DNA encoding a blasticidin S Deaminase gene expression cassette has been inserted into the Bam HI restriction site in pGL3-MMTV. Such a plasmid is selected and is designated as pGL3-MMTV-BSD.

In order to produce stably transformed cells which stably contain in one of its chromosomes the MMTV reporter gene (hereinafter referred to as the stably transformed MMTV cassette cell), the plasmid pGL3-MMTV-BSD is linearized and introduced into HeLa cells.

The plasmid pGL3-MMTV-BSD is restriction digested with restriction enzyme Sal I to linearize pGL3-MMTV-BSD.

Approximately $5 \times 10^5$ HeLa cells were cultured as host cells for 1 day using dishes having a diameter of about 10 cm (Falcon) in DMEM medium (Nissui Pharmaceutical Co.) containing 10% FBS at 37° C. under the presence of 5% $CO_2$.

The linearized pGL3-MMTV-BSD is then introduced to the cultured HeLa cells by a lipofection method using lipofectamine (Life Technologies). According with the manual provided with the lipofectamine, the conditions under the lipofection method included 5 hours of treatment, 7 µg/dish of the linearized pGL3-MMTV-BSD and 21 µl/dish of lipofectamine.

After the lipofection treatment, the DMEM medium is exchanged with DMEM medium containing 10% FBS and the transformed HeLa cells are cultured for about 36 hours. Next, the transformed HeLa cells are removed and collected from the dish by trypsin treatment and are transferred into a container containing a medium to which blasticidin S is added to a concentration of 16 µg/ml. The transformed HeLa cells are cultured in such medium containing blasticidin S for 1 month while exchanging the medium every 3 or 4 days to a fresh batch of the medium containing blasticidin S.

The resulting clones, which are able to proliferate and produce a colony having a diameter of from 1 to several mm, are transferred as a whole to the wells of a 96-well ViewPlate (Berthold) to which medium is previously dispensed thereto. The colonies of the clones are further cultured. When the clones proliferated to such a degree that they covered 50% or more of the bottom surface of each of the wells (about 5 days after the transfer), the clones are removed and collected by trypsin treatment. The clones then are divided into 2 subcultures. One of the subcultures is transferred to a 96-well View-Plate, which is designated as the master plate. The other subculture is transferred to a 96-well ViewPlate, which is designated as the assay plate. The master plate and the assay plate contain medium so that the clones can be cultured. The master pate is continuously cultured under similar conditions.

The medium is then removed from the wells of the assay plate and the clones attached to the well walls are washed twice with PBS(-). A 5-fold diluted lysis buffer PGC50 (Toyo Ink) is added, respectively, to the clones in the wells of the assay plate at 20 μl per well. The assay plate is left standing at room temperature for 30 minutes and is set on a luminometer LB96P (Berthold), which is equipped with an automatic substrate injector. Subsequently, 50 μl of the substrate solution PGL100 (Toyo Ink) is automatically dispensed to the lysed clones in the assay plate to measure the luciferase activity therein with the luminometer LB96P. A plurality of the clones, which exhibited a high luciferase activity are selected therefrom.

Samples of the selected clones are then cultured at 37° C. for 1 to 2 weeks in the presence of 5% $CO_2$ using dishes having a diameter of about 10 cm (Falcon) in charcoal dextran FBS/E-MEM medium.

The plasmid pRc/RSV-hAR Kozak is then introduced to the samples of the selected clones by a lipofection method using lipofectamine (Life Technologies) to provide a second round of clones. According with the manual provided with the lipofectamine, the conditions under the lipofection method included 5 hours of treatment, 7 μg/dish of the plasmids above and 21 μl/dish of lipofectamine. A DMSO solution containing dihydrotestosterone (DHT), which is the natural cognate ligand of a normal AR, is then added to the resulting second clones so that the concentration of DHT in the medium is 10 nM. After culturing the second clones for 2 days, the luciferase activity is measured, similarly to the above, for each of the second clones. The clone in the master plate, which provided the second clone exhibiting the highest induction of luciferase activity, is selected as the stably transformed MMTV cassette cell.

In this regard, the stably transformed MMTV cassette cell can be used in reporter assays with AR, GR, PR, MR and the like.

6.17. Example 17 Reporter Assay of the Human Normal AR as a Human Test AR

6.17.1. Preparation of Stably Transformed MMTV Cassette Cell

Approximately $2\times10^6$ stably transformed MMTV cassette cells provided in 6.16., are cultured at 37° C. for 1 day in the presence of 5% $CO_2$ using dishes having a diameter of about 10 cm (Falcon) in charcoal dextran FBS/E-MEM medium.

For transient expression, the plasmid pRc/RSV-hAR Kozak is introduced into a subculture of the stably transformed MMTV cassette cells by a lipofection method using lipofectamine (Life Technologies). According with the manual provided with the lipofectamine, the conditions under the lipofection method include 5 hours of treatment, 7 μg/dish of the pRc/RSV-hAR Kozak and 21 μl/dish of lipofectamine. After culturing the resulting cell subculture at 37° C. for 16 hours in the presence of 5% $CO_2$, the charcoal dextran FBS/E-MEM medium therein is exchanged to fresh batches of the charcoal dextran FBS/E-MEM medium to further culture the cell subculture for 3 hours. The cell subculture is then collected and uniformly suspended in charcoal dextran FBS/E-MEM medium to provide a subculture thereof.

6.17.2. Measurement of the Activity for Transactivation of the MMTV Reporter Gene First DMSO solutions are prepared to contain various concentrations of flutamide. The flutamide is used in the first DMSO solution as an agonist directed to the normal AR. Further, second DMSO solutions are prepared to contain 10 nM of DHT and the various concentrations of the flutamide. The flutamide is used in the second DMSO solution as an antagonist directed to the normal AR.

The first and second DMSO solutions are then mixed, respectively, with the subcultures prepared in the above 6.17.1., in the 96-well ViewPlates such that the concentration of the first or second DMSO solution in each of the wells is about 0.1% (v/v). Further, as a standard, a sample of the cell subculture which is provided in 6.17.1., is nixed with a DMSO solution containing DHT, in the wells of a 96-View-Plate.

The cells are then cultured for 40 hours at 37° C. in the presence of 5% $CO_2$. A 5-fold diluted lysis buffer PGC50 (Toyo Ink) is added, respectively, to the subcultures in the wells at 50 μl per well. The 96-well ViewPlates are periodically and gently shook while being incubated at room temperature for 30 minutes. Ten microliters (10 μl) of the lysed cells are then transferred, respectively, to white 96-well sample plates (Berthold) and are set on a luminometer LB96P (Berthold), which is equipped with an automatic substrate injector. Subsequently, 50 μl of the substrate solution PGL100 (Toyo Ink) is automatically dispensed, respectively, to each of the lysed cells in the white 96-well sample plates to instantaneously measure for 5 seconds the luciferase activity therein with the luminometer LB96P.

Further, the above reporter assay can use as the test AR, a mutant AR. In this regard, a plasmid encoding a mutant AR is used instead of pRc/RSV-hAR Kozak. To provide the plasmid encoding the mutant AR, a Kozak consensus sequence is added operably upstream from a polynucleotide encoding a mutant AR and the resulting polynucleotide is inserted into a restriction site of Hind III in the plasmid pRc/RSV (Invitrogen), as similarly described above.

6.18. Example 18 Reporter Assay of a Human Normal GR as the Human Test GR

6.18.1. Preparation of Stably Transformed MMTV Cassette Cell

Approximately $2\times10^6$ stably transformed MMTV cassette cells provided in 6.16., are cultured at 37° C. for 1 day in the presence of 5% $CO_2$ using dishes having a diameter of about 10 cm (Falcon) in charcoal dextran FBS/E-MEM medium.

For transient expression, the plasmid pRc/RSV-hGR Kozak is introduced into a subculture of the stably transformed MMTV cassette cells by a lipofection method using lipofectamine (Life Technologies). According with the manual provided with the lipofectamine, the conditions under the lipofection method include 5 hours of treatment, 7 μg/dish of the pRc/RSV-hAR Kozak and 21 μl/dish of lipofectamine. After culturing the resulting cell subculture at 37° C. for 16 hours in the presence of 5% $CO_2$, the charcoal dextran FBS/E-MEM medium therein is exchanged to fresh batches of the charcoal dextran FBS/E-MEM medium to further culture the cell subculture for 3 hours. The cell subculture is then collected and uniformly suspended in charcoal dextran FBS/E-MEM medium.

6.18.2. Measurement of the Activity for Transactivation of the MMTV Reporter Gene First DMSO solutions are prepared to contain various concentrations of pregnanolone 16α carbonitrile (PCN). The PCN is used in the first DMSO solutions as an agonist with the normal GR. Further, the second DMSO solutions are prepared to contain 10 nM of corticosterone and the various concentrations of PCN. The PCN is used in the second DMSO solutions as an antagonist with the normal GR.

The first and second DMSO solutions are then mixed, respectively, with the cell subcultures prepared in the above 6.18.1., in wells of the 96-well ViewPlates such that the concentration of the first or second DMSO solution in each of the wells is about 0.1% (v/v). Further, as a standard, a sample of the cell subculture is mixed with a DMSO solution containing corticosterone in the wells of a 96-well ViewPlate.

The cells are then cultured for 40 hours at 37° C. in the presence of 5% $CO_2$. A 5-fold diluted lysis buffer PGC50 (Toyo Ink) is added, respectively, to the subcultures in the wells at 50 µl per well. The 96-well ViewPlates are periodically and gently shook while being incubated at room temperature for 30 minutes. Ten microliters (10 µl) of the lysed cells are then transferred, respectively, to white 96-well sample plates (Berthold) and are set on a luminometer LB96P (Berthold), which is equipped with an automatic substrate injector. Subsequently, 50 µl of the substrate solution PGL100 (Toyo Ink) is automatically dispensed, respectively, to each of the lysed cells in the white 96-well sample plates to instantaneously measure for 5 seconds the luciferase activity therein with the luminometer LB96P.

Further, the above reporter assay can use as the test GR, a mutant GR. In this regard, a plasmid encoding the mutant GR is used instead of pRc/RSV-hGR Kozak. To provide the plasmid encoding the mutant GR, a Kozak consensus sequence is added operably upstream from a polynucleotide encoding a mutant GR and the resulting polynucleotide is inserted into a restriction site of Hind III in the plasmid pRc/RSV (Invitrogen), as similarly described above.

6.19. Example 19 Reporter Assay of Human Normal PR as the Human Test PR

6.19.1. Preparation of Stably Transformed MMTV Cassette Cell

Approximately $2 \times 10^6$ stably transformed MMTV cells provided in 6.16., are cultured at 37° C. for 1 day in the presence of 5% $CO_2$ using dishes having a diameter of about 10 cm (Falcon) in charcoal dextran FBS/E-MEM medium.

For transient expression the plasmid pRc/RSV-hPR Kozak is introduced into a subculture of the stably transformed MMTV cassette cells by a lipofection method using lipofectamine (Life Technologies). According with the manual provided with the lipofectamine, the conditions under the lipofection method include 5 hours of treatment, 7 µg/dish of the pRc/RSV-hAR Kozak and 21 µl/dish of lipofectamine. After culturing the resulting cell subculture at 37° C. for 16 hours in the presence of 5% $CO_2$, the charcoal dextran FBS/E-MEM medium therein is exchanged to fresh batches of the charcoal dextran FBS/E-MEM medium to further culture each of the cell subculture for 3 hours. The cell subculture is then collected and uniformly suspended in charcoal dextran FBS/E-MEM medium.

6.19.2. Measurement of the Activity for Transactivation of the MMTV Reporter Gene First DMSO solutions are prepared to contain various concentrations of RU486. The RU486 is used in the first DMSO solutions as an agonist directed to the normal PR. Further, second DMSO solutions are prepared to contain 10 nM of progesterone and the various concentrations of RU486. The RU486 is used in the second DMSO solutions as an antagonist directed to the normal PR.

The first and second DMSO solutions are mixed, respectively, with the cell subcultures prepared in the above 6.19.1., in the 96-well ViewPlates such that the concentration of the first or second DMSO solution in each of the wells is about 0.1% (v/v). Further, as a standard, a sample of the cell subculture is mixed with a DMSO solution containing progesterone.

The cells are then cultured for 40 hours at 37° C. in the presence of 5% $CO_2$. A 5-fold diluted lysis buffer PGC50 (Toyo Ink) is added, respectively, to the cells in the wells at 50 µl per well. The 96-well ViewPlates are periodically and gently shook while being incubated at room temperature for 30 minutes. Ten microliters (10 µl) of the lysed cells are then transferred, respectively, to white 96-well sample plates (Berthold) and are set on a luminometer LB96P (Berthold), which is equipped with an automatic substrate injector. Subsequently, 50 µl/well of the substrate solution PGL100 (Toyo Ink) is automatically dispensed, respectively, to each of the lysed cells in the white 96-well sample plates to instantaneously measure for 5 seconds the luciferase activity therein with the luminometer LB96P.

Further, the above reporter assay can use as the test PR, a mutant PR. In this regard, a plasmid encoding the mutant PR is used instead of pRc/RSV-hPR Kozak. To provide the plasmid encoding the mutant PR, a Kozak consensus sequence is added operably upstream from a polynucleotide encoding a mutant PR and the resulting polynucleotide is inserted into a restriction site of Hind III in the plasmid pRc/RSV (Invitrogen), as similarly described above.

6.20. Example 20 Production of a Plasmid Encoding Human Normal ERβ

A human prostate cDNA library (CLONETECH, Quick clone cDNA#7123-1) is utilized to PCR amplify therefrom a cDNA encoding a human normal ERβ (Genbank Accession No. AB006590). The PCR mixture in this PCR amplification contains 10 ng of the human liver cDNA library, 10 pmol of an oligonucleotide depicted in SEQ ID:192, 10 pmol of an oligonucleotide depicted in SEQ ID:193, LA-Taq Polymerase (Takara Shuzo), the buffer provided with the LA-Taq Polymerase and dNTPs (dATP, dTTP, dGTP, dCTP). The oligonucleotides depicted in SEQ ID:192 and SEQ ID:193 are synthesized with a DNA synthesizer (Model 394, Applied Biosystems). In this PCR amplification, there is repeated 35 times with a PCR system 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm with ethidium bromide staining, that the cDNA encoding human normal ERβ is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA, 10 pmol of an oligonucleotide depicted in SEQ ID:194 and 10 pmol of an oligonucleotide depicted in SEQ ID:195, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L: Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding human normal ERβ. Such a plasmid is selected and is designated as pRc/RSV-hERβ Kozak.

6.21. Example 21 Reporter Assay of Human Normal ERβ as the Human Test ERβ

6.21.1. Preparation of Stably Transformed ERE Cassette Cell

Approximately $2 \times 10^6$ stably transformed ERE cassette cells provided in 6.3., are cultured at 37° C. for 1 day in the presence of 5% $CO_2$ using dishes having a diameter of about 10 cm (Falcon) in charcoal dextran FBS/E-MEM medium.

For transient expression, the plasmid pRc/RSV-hERβ Kozak is introduced into a subculture of the stably transformed ERE cassette cells by a lipofection method using lipofectamine (Life Technologies). According with the manual provided with the lipofectamine, the conditions under the lipofection method include 5 hours of treatment, 7 μg/dish of the pRc/RSV-hERβ Kozak and 21 μl/dish of lipofectamine. After culturing the resulting cell subculture at 37° C. for 16 hours in the presence of 5% $CO_2$, the charcoal dextran FBS/E-MEM medium therein is exchanged to fresh batches of the charcoal dextran FBS/E-MEM medium to further culture the cell subculture for 3 hours. The cell subculture is then collected and uniformly suspended in charcoal dextran FBS/E-MEM medium.

6.21.2. Measurement of the Activity for Transactivation of the ERE Reporter Gene First DMSO solutions are prepared to contain various concentrations of 4-hydroxytamoxifen. The 4-hydroxytamoxifen is used in the first DMSO solutions as an agonist directed to the human normal ERβ. Further, second DMSO solutions are prepared to contain 10 nM of E2 and the various concentrations of 4-hydroxytamoxifen. The 4-hydroxytamoxifen is used in the second DMSO solutions as an antagonist directed to the ERβ.

The first and second DMSO solutions are mixed, respectively, with the subcultures prepared in the above 6.21.1., in the 96-well ViewPlates such that the concentration of the first or second DMSO solution in each of the wells is about 0.1% (v/v). Further, as a standard, a sample of the cells is mixed with DMSO solutions containing E2 in the wells of a 96-well ViewPlate.

The cells are then cultured for 40 hours at 37° C. in the presence of 5% $CO_2$. A 5-fold diluted lysis buffer PGC50 (Toyo Ink) is added, respectively, to the cells in the wells at 50 μl per well. The 96-well ViewPlates are periodically and gently shook while being incubated at room temperature for 30 minutes. Ten microliters (10 μl) of the lysed cells are then transferred, respectively, to white 96-well sample plates (Berthold) and are set on a luminometer LB96P (Berthold), which is equipped with an automatic substrate injector. Subsequently, 50 μl/well of the substrate solution PGL100 (Toyo Ink) is automatically dispensed, respectively, to each of the lysed cells in the white 96-well sample plates to instantaneously measure for 5 seconds the luciferase activity therein with the luminometer LB96P.

Further, the above reporter assay can use as the test ERβ, a mutant ERβ. In this regard, a plasmid encoding the mutant ERβ is used instead of pRc/RSV-hERβ Kozak. To provide the plasmid encoding the mutant ERβ, a Kozak consensus sequence is added operably upstream from a polynucleotide encoding a mutant ERβ and the resulting polynucleotide is inserted into a restriction site of Hind III in the plasmid pRc/RSV (Invitrogen), as similarly described above.

6.22. Example 22 Production of a Plasmid Encoding a Human Normal TRα

A human liver cDNA library (CLONETECH, Quick clone cDNA#7113-1) is utilized to PCR amplify therefrom a cDNA encoding a human normal TRα (Genbank Accession No. M24748). The PCR mixture in this PCR amplification contains 10 ng of the human liver cDNA library, 10 pmol of an oligonucleotide depicted in SEQ ID:196, 10 pmol of an oligonucleotide depicted in SEQ ID:197, LA-Taq Polymerase (Takara Shuzo), the buffer provided with the LA-Taq Polymerase and dNTPs (dATP, dTTP, dGTP, dCTP). The oligonucleotides depicted in SEQ ID:196 and SEQ ID:197 are synthesized with a DNA synthesizer (Model 394, Applied Biosystems). In this PCR amplification, there is repeated 35 times with a PCRsystem 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm with ethidium bromide staining, that the cDNA encoding human normal TRα is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA encoding human normal TRα, 10 pmol of an oligonucleotide depicted in SEQ ID:198 and 10 pmol of an oligonucleotide depicted in SEQ ID:199, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L: Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform *E. coli* competent DH5α cells (TOYOBO). The transformed *E. coli* cells are cultured in LB-amp. The clones thereof showing an ampicillin resistance are then recovered. Some of the clones are then used to isolate therefrom the plasmids derived from the ligation reaction. An aliquot sample of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding human normal TRα. Such a plasmid is selected and is designated as pRc/RSV-hTRα-Kozak.

6.23. Example 23 Production of a Plasmid Encoding a Human Normal TRβ

A human liver cDNA library (CLONETECH, Quick clone cDNA#7113-1) is utilized to PCR amplify therefrom a cDNA encoding a human normal TRβ (Genbank Accession No. M26747). The PCR mixture in this PCR amplification contains 10 ng of the human liver cDNA library, 10 pmol of an oligonucleotide depicted in SEQ ID:200, 10 pmol of an oligonucleotide depicted in SEQ ID:201, LA-Taq Polymerase (Takara Shuzo), the buffer provided with the LA-Taq Polymerase and dNTPs (dATP, dTTP, dGTP, dCTP). The oligonucleotides depicted in SEQ ID:200 and SEQ ID:201 are synthesized with a DNA synthesizer (Model 394, Applied Biosystems). In this PCR amplification, there is repeated 35 times with a PCR system 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm with ethidium bromide staining, that the cDNA encoding human normal TRβ is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the stair codon (ATG) in the cDNA. The PCR mixture in this PCR amplification contains 100 ng of the cDNA encoding normal TRα, 10 pmol of an oligonucleotide depicted in SEQ ID:202 and 10 pmol of an oligonucleotide depicted in SEQ ID:203, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L, Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform *E. coli* competent DH5α cells (TOYOBO). The transformed *E. coli* cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding human normal TRβ. Such a plasmid is selected and is designated as pRc/RSV-hTRβ Kozak.

6.24. Example 24 Production of a Plasmid Containing an DR4 Reporter Gene

An oligonucleotide depicted in SEQ ID:204 and an oligonucleotide having a nucleotide sequence complementary thereto are synthesized with a DNA synthesizer. The oligonucleotide depicted in SEQ ID: 204 is synthesized to encode one of the strands of an DR4. The second oligonucleotide is synthesized to have a nucleotide sequence complementary to the first oligonucleotide. The two oligonucleotides are annealed together to produce a DNA encoding a DR4 sequence (hereinafter referred to as the DR4 DNA). A T4 polynucleotide kinase is allowed to react with the DR4 DNA to phosphorylate the ends thereof. The DR4 DNA is then ligated together with a T4 DNA ligase to provide a DR4x5 DNA having a 5 tandem repeat of the DR4 sequence. The ligation reaction mixture is then subjected to low melting point agarose gel electrophoresis (Agarose L, Nippon Gene), and the DR4x5 DNA is recovered from the gel.

The plasmid pGL3-TATA provided in 6.2., is restriction digested with restriction enzyme Sma I and is then treated with BAP at 65° C. for 1 hour. The restriction digested reaction mixture is then subjected to low melting point agarose gel electrophoresis (Agarose L, Nippon Gene). After recovering the DNA fragment having a nucleotide sequence encoding firefly luciferase from the low melting point agarose gel, 100 ng of the recovered DNA fragment and 1 µg of the DR4x5 DNA are used in a ligation reaction. The resulting ligation reaction mixture is then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then restriction digested with restriction enzymes Kpn I and Xho I. The restriction digestion reaction mixtures are subjected to agarose gel electrophoresis to confirm that there is a plasmid having a structure in which the DR4x5 DNA is inserted into the restriction site of restriction enzyme Sma I in the pGL3-TATA. Such a plasmid is selected and is designated as pGL3-TATA-DR4x5.

The plasmid pGL3-TATA-DR4x5 is then restriction digested with restriction enzyme Sal I. After a Blunting Kit (Takara Shuzo) is used to blunt the ends of the restriction digested pGL3-TATA-DR4x5, the restriction digested pGL3-TATA-DR4x5 is treated with BAP at 65° C. for 1 hour. The Blunting Kit is also used to blunt the ends of the DNA fragment encoding the blasticidin S deaminase gene (BamH I-BamH I fragment) provided in 6.2.

The DNA fragment encoding a blasticidin S deaminase gene expression cassette and the restriction digested pGL3-TATA-DR4x5 are then mixed together for a ligation reaction with T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems) to confirm whether there is a plasmid which has structure in which the DNA encoding a blasticidin S deaminase gene expression cassette is inserted into the restriction site of restriction enzyme Sal I in pGL3-TATA-DR4x5. Such a plasmid is selected and is designated as pGL3-TATA-DR4x5-BSD.

6.25. Example 25 Production of a Stably Transformed Cell which Stably Contains in One of its Chromosomes the DR4 Reporter Gene In order to produce stably transformed cells which stably contains in one of its chromosomes the DR4 reporter gene (hereinafter referred to as the stably transformed DR4 cassette cell, the plasmid pGL3-TATA-DR4x5-BSD was linearized and introduced into HeLa cells.

The plasmid pGL3-TATA-DR4x5-BSD is restriction digested with restriction enzyme Not I to linearize pGL3-TATA-DR4x5-BSD.

Approximately $5 \times 10^5$ HeLa cells are cultured as host cells for 1 day using dishes having a diameter of about 10 cm (Falcon) in DMEM medium (Nissui Pharmaceutical Co.) containing 10% FBS at 37° C. in the presence of 5% $CO_2$.

The linearized pGL3-TATA-DR4x5-BSD is then introduced to the cultured HeLa cells by a lipofection method using lipofectamine (Life Technologies). According with the manual provided with the lipofectamine, the conditions under the lipofection method include 5 hours of treatment, 7 µg/dish of the linearized pGL3-TATA-DR4x5-BSD and 21 µl/dish of lipofectamine.

After the lipofection treatment, the DMEM medium is exchanged with DMEM medium containing 10% FBS and the transformed HeLa cells are cultured for about 36 hours. Next, the transformed HeLa cells are removed and collected from the dish by trypsin treatment and are transferred into a container containing a medium to which blasticidin S is added to a concentration of 16 µg/ml. The transformed HeLa cells are cultured in such medium containing blasticidin S for 1 month while exchanging the medium containing blasticidin S every 3 or 4 days to a fresh batch of the medium containing blasticidin S.

The resulting clones, which are able to proliferate and produce a colony having a diameter of from 1 to several mm, are transferred, respectively, as a whole to the wells of a 96-well ViewPlate (Berthold) to which medium is previously dispensed thereto. The clones are further cultured. When the clones proliferated to such a degree that clones therein covered 50% or more of the bottom surface of each of the wells (about 5 days after the transfer), the clones are removed and collected by trypsin treatment. Each of the clones then are divided into 2 subcultures. One of the subcultures is transferred to a 96-well ViewPlate, which is designated as the master plate. The other subculture was transferred to a 96-well ViewPlate, which is designated as the assay plate. The master plate and the assay plate contain medium so that the clones can be cultured. The master pate is continuously cultured under similar conditions.

The medium in the wells of the assay plate is then removed therefrom and the clones attached to the well walls are washed twice with PBS(−). A 5-fold diluted lysis buffer PGC50 (Toyo Ink) is added, respectively, to the clones in the wells of the assay plate at 20 µl/well. The assay plate is left standing at room temperature for 30 minutes and is set on a luminometer LB96P (Berthold), which is equipped with an automatic substrate injector. Subsequently, 50 µl of the substrate solution PGL100 (Toyo Ink) is automatically dispensed to the lysed clones in the assay plate to measure the luciferase activity therein with the luminometer LB96P. A plurality of the clones, which exhibited a luciferase activity are selected therefrom.

Samples of the selected clones are then cultured at 37° C. for 1 day in the presence of 5% $CO_2$ using dishes having a diameter of about 10 cm (Falcon) in charcoal dextran FBS/E-MEM medium.

The plasmid pRc/RSV-hTRαKozak is then introduced to the samples of the selected clones by a lipofection method using lipofectamine (Life Technologies) to provide a second round of clones. According with the manual provided with the lipofectamine, the conditions under the lipofection method included 5 hours of treatment, 7 µg/dish of pRc/RSV-hTRα-Kozak above and 21 µl/dish of lipofectamine. A DMSO solution containing triiodothyronine (T3), which is the natural cognate ligand of a human normal TRα, is then added to the resulting second clones so that the concentration of T3 in the medium is 10 nM. After culturing the second clones for 2 days, the luciferase activity is measured, similarly to the above, for each of the second clones. The clone in the master plate, which provided the second clone exhibiting the highest induction of luciferase activity, is selected as the stably transformed DR4 cassette cell.

In this regard, the stably transformed DR4 cassette cell can be used in reporter assays with TRα, TRβ, CAR, LXR, PXR and the like.

6.26. Example 26 Production of a Plasmid Encoding Human Normal VDR

A human liver cDNA library (CLONETECH, Quick clone cDNA#7113-1) is utilized to PCR amplify therefrom a cDNA encoding a human normal VDR (Genbank Accession No. J03258). The PCR mixture in this PCR amplification contains 10 ng of the human liver cDNA library, 10 pmol of an oligonucleotide depicted in SEQ ID:205, 10 pmol of an oligonucleotide depicted in SEQ ID:206, LA-Taq Polymerase (Takara Shuzo), the buffer provided with the LA-Taq Polymerase and dNTPs (dATP, dTTP, dGTP, dCTP). The oligonucleotides depicted in SEQ ID:205 and SEQ ID:206 are synthesized with a DNA synthesizer (Model 394, Applied Biosystems). In this PCR amplification, there is repeated 35 times with a PCR system 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L, Nippon Gene) to confirm with ethidium bromide staining, that the cDNA encoding human normal VDR is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA encoding normal. The PCR mixture in this PCR amplification contains 100 ng of the cDNA encoding normal, 10 pmol of an oligonucleotide depicted in SEQ ID:207 and 10 pmol of an oligonucleotide depicted in SEQ ID:208, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L, Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA is used in a ligation reaction with a T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems), to confirm that there is a plasmid encoding human normal VDR. Such a plasmid is selected and is designated as pRc/RSV-hVDR Kozak.

6.27. Example 27 Production of a Plasmid Containing a DR3 Reporter Gene

An oligonucleotide depicted in SEQ ID:209 and an oligonucleotide having a nucleotide sequence complementary thereto are synthesized with a DNA synthesizer. The oligonucleotide depicted in SEQ ID: 209 is synthesized to encode one of the strands of a DR3. The second oligonucleotide is synthesized to have a nucleotide sequence complementary to the first oligonucleotide. The two oligonucleotides are annealed together to produce a DNA encoding a DR3 sequence (hereinafter referred to as the DR3 DNA). A T4 polynucleotide kinase is allowed to react with the DR3 DNA to phosphorylate the ends thereof. The DR3 DNA is then ligated together with a T4 DNA ligase to provide a DR3x5 DNA having a 5 tandem repeat of the DR3 sequence. The ligation reaction mixture is then subjected to low melting point agarose gel electrophoresis (Agarose L, Nippon Gene), and the DR3x5 DNA is recovered from the gel.

The plasmid pGL3-TATA provided in 6.2., is restriction digested with restriction enzyme Sma I and is then treated with BAP at 65° C. for 1 hour. The restriction digested reaction mixture is then subjected to low melting point agarose gel electrophoresis (Agarose L, Nippon Gene). After recovering the DNA fragment having a nucleotide sequence encoding firefly luciferase from the low melting point agarose gel, 100 ng of the recovered DNA fragment and 1 μg of the DR3x5 DNA are used in a ligation reaction. The resulting ligation reaction mixture is then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids is then restriction digested with restriction enzymes Kpn I and Xho I. The restriction digestion reaction mixtures are subjected to agarose gel electrophoresis to confirm that there is a plasmid having a structure in which the DR3x5 DNA is inserted into the restriction site of restriction enzyme Sma I in the pGL3-TATA. Such a plasmid is selected and is designated as pGL3-TATA-DR3x5.

The plasmid pGL3-TATA-DR3x5 is then restriction digested with restriction enzyme Sal I. After a Blunting Kit (Takara Shuzo) is used to blunt the ends of the restriction digested pGL3-TATA-DR3x5, the restriction digested pGL3-TATA-DR3x5 is treated with BAP at 65° C. for 1 hour. The Blunting Kit is also used to blunt the ends of the DNA fragment having the blasticidin S deaminase gene expression cassette (BamH I-BamH I fragment) provided in 6.2. The blunt ended pGL3-TATA-DR3x5 and the blunt ended DNA fragment having the blasticidin S deaminase gene expression cassette are used in a ligation reaction with T4 DNA ligase. The resulting ligation reaction mixture is then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. The isolated plasmid in which the DNA fragment having the blasticidin S deaminase gene expression cassette is inserted to the restriction site of restriction enzyme Sal I in pGL3-TATA-DR3x5 is selected and is designated as pGL3-TATA-DR3x5-BSD.

6.28. Example 28 Production of a Stably Transformed Cassette Cell which Stably Contains in One of its Chromosomes the DR3 Reporter Gene In order to produce stably transformed cells which stably contain in one of its chromosomes the DR3 reporter gene (hereinafter referred to as the stably transformed DR3 cassette cell, the plasmid pGL3-TATA-DR3x5-BSD was linearized and introduced into HeLa cells.

The plasmid pGL3-TATA-DR3x5-BSD is restriction digested with restriction enzyme Not I to linearize pGL3-TATA-DR3x5-BSD.

Approximately $5 \times 10^5$ HeLa cells are cultured as host cells for 1 day using dishes having a diameter of about 10 cm (Falcon) in DMEM medium (Nissui Pharmaceutical Co.) containing 10% FBS at 37° C. under the presence of 5% $CO_2$.

The linearized pGL3-TATA-DR3x5-BSD are then introduced to the cultured HeLa cells by a lipofection method using lipofectamine (Life Technologies). According with the manual provided with the lipofectamine, the conditions under the lipofection method include 5 hours of treatment, 7 μg/dish of the linearized pGL3-TATA-DR3x5-BSD and 21 μl/dish of lipofectamine.

After the lipofection treatment, the DMEM medium is exchanged with DMEM medium containing 10% FBS and the transformed HeLa cells are cultured for about 36 hours. Next, the transformed HeLa cells are removed and collected from the dish by trypsin treatment and are transferred into a container containing a medium to which blasticidin S is added to a concentration of 16 μg/ml. The transformed cells are cultured in such medium containing blasticidin S for 1 month while exchanging the medium containing blasticidin S every 3 or 4 days to a fresh batch of the DMEM medium containing blasticidin S.

The clones, which are able to proliferate and produce a colony having a diameter of from 1 to several mm, are transferred, respectively, as a whole to the wells of a 96-well ViewPlate (Berthold) to which medium is previously dispensed thereto. The clones are further cultured. When the clones proliferated to such a degree that eukaryotic clones therein covered 50% or more of the bottom surface of each of the wells (about 5 days after the transfer), the clones are removed and collected by trypsin treatment. The clones then are divided into 2 subcultures. One of the subcultures is transferred to a 96-well ViewPlate, which is designated as the master plate. The other subculture is transferred to a 96-well ViewPlate, which is designated as the assay plate. The master plate and the assay plate contain medium so that the clones can be cultured. The master pate is continuously cultured under similar conditions.

The medium in the wells of the assay plate is then removed therefrom and the clones attached to the well walls are washed twice with PBS(−). A 5-fold diluted lysis buffer PGC50 (Toyo Ink) is added, respectively, to the clones in the wells of the assay plate at 20 μl/well. The assay plate is left standing at room temperature for 30 minutes and is set on a luminometer LB96P (Berthold), which is equipped with an automatic substrate injector. Subsequently, 50 μl of the substrate solution PGL100 (Toyo Ink) is automatically dispensed to the lysed clones in the assay plate to measure the luciferase activity therein with the luminometer LB96P. A plurality of the clones, which exhibited a high luciferase activity are selected therefrom.

Samples of the selected clones are then cultured at 37° C. for 1 to 2 weeks in the presence of 5% $CO_2$ using dishes having a diameter of about 10 cm (Falcon) in charcoal dextran FBS/E-MEM medium.

The plasmid pRc/RSV-hVDR Kozak is then introduced to the samples of the selected clones by a lipofection method using lipofectamine (Life Technologies) to provide a second round of clones. According with the manual provided with the lipofectamine, the conditions under the lipofection method included 5 hours of treatment, 7 μg/dish of pRc/RSV-VDR Kozak above and 21 μl/dish of lipofectamine. A DMSO solution containing 1.25-(OH) Vitamin $D_3$, which is the natural cognate ligand of a human normal VDR, is then added to the resulting second clones so that the concentration of 1.25-(OH) Vitamin $D_3$ in the medium is 10 nM. After culturing the second clones for 2 days, the luciferase activity is measured, similarly to the above, for each of the second clones. The clone in the master plate, which provided the second clone exhibiting the highest induction of luciferase activity, is selected as the stably transformed DR3 cassette cell.

6.29. Example 29 Production of a Plasmid Encoding Normal PPAR γ

A human liver cDNA library (CLONETECH, Quick clone cDNA#7113-1) is utilized to PCR amplify therefrom a cDNA encoding a human normal PPAR γ (Genbank Accession No. U79012). The PCR mixture in this PCR amplification contains 10 ng of the human liver cDNA library, 10 pmol of an oligonucleotide depicted in SEQ ID:210, 10 pmol of an oligonucleotide depicted in SEQ ID:211, LA-Taq Polymerase (Takara Shuzo), the buffer provided with the LA-Taq Polymerase and dNTPs (dATP, dTTP, dGTP, dCTP). The oligonucleotides depicted in SEQ ID:210 and SEQ ID:211 are synthesized with a DNA synthesizer (Model 394, Applied Biosystems). In this PCR amplification, there is repeated 35 times with a PCR system 9700 (Applied Biosystems), an incubation cycle entailing an incubation at 95° C. for 1 minute followed by an incubation at 68° C. for 3 minutes.

The resulting PCR mixture is subjected to low melting point agarose gel electrophoresis (Agarose L: Nippon Gene) to confirm with ethidium bromide staining, that the cDNA encoding human normal PPAR γ is PCR amplified. After recovering the amplified cDNA from the low melting point agarose gel, a sample of the recovered cDNA is prepared with a Dye Terminator Sequence Kit FS (Applied Biosystems). The prepared sample of the cDNA is sequenced with an ABI autosequencer (Model 377, Applied Biosystems).

Another PCR amplification is then conducted to add a Kozak consensus sequence immediately upstream from the start codon (ATG) in the cDNA. The PCR mixture in this PCR amplification contains 100 ng of the cDNA encoding normal PPAR γ and Kozak consensus sequence, an oligonucleotide depicted in SEQ ID:212 and an oligonucleotide depicted in SEQ ID:211, LA-Taq Polymerase (Takara Shuzo), the buffer provided with the LA-Taq Polymerase and dNTPs (dATP, dTTP, dGTP, dCTP). In this PCR amplification, there is repeated 25 times an incubation cycle entailing an incubation at 95° C. for 1 minute followed by an incubation at 68° C. for 3 minutes. The resulting PCR mixture is subjected to low melting point agarose gel electrophoresis (Agarose L, Nippon Gene). After recovering the amplified cDNA from the low melting point agarose gel, 1 μg of the amplified cDNA is treated with a DNA Blunting Kit (Takara Shuzo) to blunt the ends of the amplified cDNA. Subsequently, the resulting cDNA therefrom is allowed to react with a T4 polynucleotide kinase to phosphorylate the ends of the cDNA. After phenol treating the phosphorylated cDNA, the phosphorylated cDNA is ethanol precipitated to achieve a purified form of the phosphorylated cDNA.

The plasmid pRc/RSV (Invitrogen) is restriction digested with restriction enzyme Hind III and is then treated with BAP for 1 hour at 65° C. The restriction digested pRc/RSV is then purified by a phenol treatment and ethanol precipitation. The restriction digested pRc/RSV is treated with a DNA Blunting Kit (Takara Shuzo) to blunt the ends thereof and is subjected to low melting point agarose gel electrophoresis (Agarose L, Nippon Gene). After recovering the restriction digested pRc/RSV from the low melting point agarose gel, 100 ng of the restriction digested pRc/RSV and all of the above purified form of the phosphorylated cDNA are used in a ligation reaction with a T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. Each of isolated plasmids is then prepared with a Dye Terminator Sequence Kit FS (Applied Biosystems). The isolated plasmids are sequenced with an ABI autosequencer (Model 377, Applied Biosystems), to confirm that there is a plasmid encoding human normal PPAR γ. Such a plasmid is selected and is designated as pRc/RSV-hPPAR γ Kozak.

6.30. Example 30 Production of a Plasmid Containing a DR1 Reporter Gene

An oligonucleotide depicted in SEQ ID:213 and an oligonucleotide having a nucleotide sequence complementary thereto are synthesized with a DNA synthesizer. The oligonucleotide depicted in SEQ ID: 213 is synthesized to encode one of the strands of a DR1 sequence. The second oligonucleotide is synthesized to have a nucleotide sequence complementary to the first oligonucleotide. The two oligonucleotides are annealed together to produce a DNA encoding a DR1 sequence (hereinafter referred to as the DR1 DNA). A T4 polynucleotide kinase is allowed to react with the DR1 DNA to phosphorylate the ends thereof. The DR1 DNA is then ligated together with a T4 DNA ligase to provide a DR1x5 DNA having a 5 tandem repeat of the DR 1 sequence. The ligation reaction mixture is then subjected to low melting point agarose gel electrophoresis (Agarose L, Nippon Gene), and the DR1x5 DNA is recovered from the gel.

The plasmid pGL3-TATA provided in 6.2., is restriction digested with restriction enzyme Sma I and is then treated with BAP at 65° C. for 1 hour. The restriction digestion reaction mixture is then subjected to low melting point agarose gel electrophoresis (Agarose L, Nippon Gene). After recovering the DNA fragment having a nucleotide sequence encoding firefly luciferase from the low melting point agarose gel, 100 ng of the recovered DNA fragment and 1 μg of the DR1x5 DNA are used in a ligation reaction with T4 DNA ligase. The resulting ligation reaction mixture is then used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids is then restriction digested with restriction enzymes Kpn I and Xho I. The restriction digestion reaction mixtures are subjected to agarose gel electrophoresis to confirm that there is a plasmid in which the DR1x5 DNA is inserted into the restriction site of restriction enzyme Sma I in the pGL3-TATA. The plasmid is then sequenced with an ABI autosequencer (Model 377, Applied Biosystems), to confirm that there is provided a plasmid having a 5 tandem repeat of the DR1 sequence. Such a plasmid is selected and is designated as pGL3-TATA-DR1x5.

The plasmid pGL3-TATA-DR1x5 is then restriction digested with restriction enzyme Sal I. After a Blunting Kit (Takara Shuzo) is used to blunt the ends of the restriction digested pGL3-TATA-DR1x5, the restriction digested pGL3-TATA-DR1x5 is treated with BAP at 65° C. for 1 hour. The Blunting Kit is also used to blunt the ends of the DNA fragment encoding the blasticidin S deaminase gene (BamH I-BamH I fragment derived from pUCSV-BSD (Funakoshi)) provided in 6.2.

The DNA fragment encoding a blasticidin S deaminase gene expression cassette and the restriction digested pGL3-TATA-DR1x5 are then mixed together for a ligation reaction with T4 DNA ligase. The ligation reaction mixture is used to transform E. coli competent DH5α cells (TOYOBO). The transformed E. coli cells are cultured in LB-amp. The clones thereof showing an ampicillin resistance are then recovered. Some of the clones are then used to isolate therefrom the plasmids derived from the ligation reaction. An aliquot sample of each of the isolated plasmids are then prepared with a Dye Terminator Sequence Kit FS (Applied Biosystems). The isolated plasmids are sequenced with an ABI autosequencer (Model 377, Applied Biosystems) to confirm whether the plasmid has a structure in which the DNA encoding a blasticidin S deaminase gene expression cassette has been inserted into the restriction site of restriction enzyme Sal I in pGL3-TATA-DR1x5. The plasmid is selected and is designated as pGL3-TATA-DR1x5-BSD.

6.31. Example 31 Production or a Stably Transformed Cassette Cell which Stably Contain in One of its Chromosomes the DR1 Reporter Gene In order to produce stably transformed cassette cells which stably contain in one of its chromosomes the DR1 reporter gene (hereinafter referred to as the stably transformed DR1 cassette cell), the plasmid pGL3-TATA-DR1x5-BSD is linearized and introduced into HeLa cells.

The plasmid pGL3-TATA-DR1x5-BSD is restriction digested with restriction enzyme Not I to linearize pGL3-TATA-DR1x5-BSD.

Approximately $5 \times 10^5$ HeLa cells are cultured as host cells for 1 day using dishes having a diameter of about 10 cm (Falcon) in DMEM medium (Nissui Pharmaceutical Co.) containing 10% FBS at 37° C. under the presence of 5% $CO_2$.

The linearized pGL3-TATA-DR1x5-BSD is then introduced to the cultured HeLa cells by a lipofection method using lipofectamine (Life Technologies). According with the manual provided with the lipofectamine, the conditions under the lipofection method include 5 hours of treatment, 7 µg/dish of the linearized pGL3-TATA-DR1x5-BSD and 21 µl/dish of lipofectamine.

After the lipofection treatment, the DMEM medium is exchanged with DMEM medium containing 10% FBS and the transformed HeLa cells are cultured for about 36 hours. Next, the transformed HeLa cells are removed and collected from the dish by trypsin treatment and are transferred into a container containing a medium to which blasticidin S is added to a concentration of 16 µg/ml. The transformed HeLa cells are cultured in such medium containing blasticidin S for 1 month while exchanging the medium containing blasticidin S every 3 or 4 days to a fresh batch of the medium containing blasticidin S.

The clones, which are able to proliferate and produce a colony having a diameter of from 1 to several mm, are transferred, respectively, as a whole to the wells of a 96-well ViewPlate (Berthold) to which medium is previously dispensed thereto. The clones are further cultured. When the clones proliferated to such a degree that clones therein covered 50% or more of the bottom surface of each of the wells (about 5 days after the transfer), the clones are removed and collected by trypsin treatment. The clones then are divided into 2 subcultures. One of the subcultures is transferred to a 96-well ViewPlate, which is designated as the master plate. The other subculture was transferred to a 96-well ViewPlate, which is designated as the assay plate. The master plate and the assay plate contain medium so that the clones can be cultured. The master pate is continuously cultured under similar conditions.

The medium in the wells of the assay plate is then removed therefrom and the clones attached to the well walls are washed twice with PBS(-). A 5-fold diluted lysis buffer PGC50 (Toyo Ink) is added, respectively, to the clones in the wells of the assay plate at 20 µl/well. The assay plate is left standing at room temperature for 30 minutes and is set on a luminometer LB96P (Berthold), which is equipped with an automatic substrate injector. Subsequently, 50 µl of the substrate solution PGL100 (Toyo Ink) is automatically dispensed to the lysed clones in the assay plate to measure the luciferase activity therein with the luminometer LB96P. A plurality of clones, which exhibited a high luciferase activity are selected therefrom.

Samples of the selected clones are then cultured at 37° C. for 1 to 2 weeks in the presence of 5% $CO_2$ using dishes having a diameter of about 10 cm (Falcon) in charcoal dextran FBS/E-MEM medium.

The plasmid pRc/RSV-hPPAR γ Kozak is then introduced to the samples of the selected clones by a lipofection method using lipofectamine (Life Technologies) to provide a second round of clones. According with the manual provided with the lipofectamine, the conditions under the lipofection method included 5 hours of treatment, 7 µg/dish of pRc/RSV-hPPAR γ Kozak and 21 µl/dish of lipofectamine. A DMSO solution containing 15d prostaglandin J2, which is the natural cognate ligand of a human normal PPAR γ, is then added to the resulting second clones so that the concentration of 15d prostaglandin J2 in the medium is 10 nM. After culturing the second clones for 2 days, the luciferase activity is measured, similarly to the above, for each of the second clones. The clone in the master plate, which provided the second clone exhibiting the highest induction of luciferase activity, is selected as the stably transformed DR1 cassette cell.

In this regard, the stably transformed DR1 cassette cell can be used in reporter assays with PPAR, RAR, retinoin X receptor, HNF-4, TR-2, TR-4 and the like.

7. SEQUENCE FREE TEXT

SEQ ID:1 human normal ERα

SEQ ID:2 human mutant ERαK303R

SEQ ID:3 human mutant ERαS309F

SEQ ID:4 human mutant ERαG390D

SEQ ID:5 human mutant ERαM396V

SEQ ID:6 human mutant ERαG415V

SEQ ID:7 human mutant ERαG494V

SEQ ID:8 human mutant ERαK531E

SEQ ID:9 human mutant ERαS578P

SEQ ID:10 human mutant ERαG390D/S578P

SEQ ID:11 Designed oligonucleotide primer for PCR

SEQ ID:12 Designed oligonucleotide primer for PCR

SEQ ID:13 Designed oligonucleotide for mutagenesis

SEQ ID:14 Designed oligonucleotide for mutagenesis

SEQ ID:15 Designed oligonucleotide for mutagenesis

SEQ ID:16 Designed oligonucleotide for mutagenesis

SEQ ID:17 Designed oligonucleotide for mutagenesis

SEQ ID:18 Designed oligonucleotide for mutagenesis

SEQ ID:19 Designed oligonucleotide for mutagenesis

SEQ ID:20 Designed oligonucleotide for mutagenesis

SEQ ID:21 Designed oligonucleotide for mutagenesis

SEQ ID:22 Designed oligonucleotide for mutagenesis

SEQ ID:23 Designed oligonucleotide for mutagenesis

SEQ ID:24 Designed oligonucleotide for mutagenesis

SEQ ID:25 Designed oligonucleotide for mutagenesis

SEQ ID:26 Designed oligonucleotide for mutagenesis

SEQ ID:27 Designed oligonucleotide for mutagenesis

SEQ ID:28 Designed oligonucleotide for mutagenesis

SEQ ID:29 Designed oligonucleotide primer for PCR

SEQ ID:30 Designed oligonucleotide primer for PCR

SEQ ID:31 Designed oligonucleotide primer for PCR

SEQ ID:32 Designed oligonucleotide primer for PCR

SEQ ID:33 Designed oligonucleotide primer for PCR

SEQ ID:34 Designed oligonucleotide primer for PCR

SEQ ID:35 Designed oligonucleotide primer for PCR

SEQ ID:36 Designed oligonucleotide primer for PCR

SEQ ID:37 Designed oligonucleotide primer for PCR

SEQ ID:38 Designed oligonucleotide primer for PCR

SEQ ID:39 Designed oligonucleotide primer for PCR

SEQ ID:40 Designed oligonucleotide primer for PCR

SEQ ID:41 Designed oligonucleotide primer for PCR

SEQ ID:42 Designed oligonucleotide primer for PCR

SEQ ID:43 Designed oligonucleotide primer for PCR

SEQ ID:44 Designed oligonucleotide primer for PCR
SEQ ID:45 Designed oligonucleotide primer for PCR
SEQ ID:46 Designed oligonucleotide primer for PCR
SEQ ID:47 Designed oligonucleotide primer for PCR
SEQ ID:48 Designed oligonucleotide primer for PCR
SEQ ID:49 Designed oligonucleotide primer for PCR
SEQ ID:50 Designed oligonucleotide primer for PCR
SEQ ID:51 Designed oligonucleotide primer for PCR
SEQ ID:52 Designed oligonucleotide primer for PCR
SEQ ID:53 Designed oligonucleotide primer for PCR
SEQ ID:54 Designed oligonucleotide primer for PCR
SEQ ID:55 Designed oligonucleotide primer for PCR
SEQ ID:56 Designed oligonucleotide primer for PCR
SEQ ID:57 Designed oligonucleotide primer for PCR
SEQ ID:58 Designed oligonucleotide primer for PCR
SEQ ID:59 Designed oligonucleotide primer for PCR
SEQ ID:60 Designed oligonucleotide primer for PCR
SEQ ID:61 Designed oligonucleotide primer for PCR
SEQ ID:62 Designed oligonucleotide primer for PCR
SEQ ID:63 Designed oligonucleotide primer for PCR
SEQ ID:64 Designed oligonucleotide primer for PCR
SEQ ID:65 Designed oligonucleotide primer for PCR
SEQ ID:66 Designed oligonucleotide primer for PCR
SEQ ID:67 Designed oligonucleotide primer for PCR
SEQ ID:68 Designed oligonucleotide primer for PCR
SEQ ID:69 Designed oligonucleotide primer for PCR
SEQ ID:70 Designed oligonucleotide primer for PCR
SEQ ID:71 Designed oligonucleotide primer for PCR
SEQ ID:72 Designed oligonucleotide primer for PCR
SEQ ID:73 Designed oligonucleotide primer for PCR
SEQ ID:74 Designed oligonucleotide primer for PCR
SEQ ID:75 Designed oligonucleotide primer for PCR
SEQ ID:76 Designed oligonucleotide primer for PCR
SEQ ID:77 Designed oligonucleotide primer for PCR
SEQ ID:78 Designed oligonucleotide primer for PCR
SEQ ID:79 Designed oligonucleotide primer for PCR
SEQ ID:80 Designed oligonucleotide primer for PCR
SEQ ID:81 Designed oligonucleotide primer for PCR
SEQ ID:82 Designed oligonucleotide primer for PCR
SEQ ID:83 Designed oligonucleotide primer for PCR
SEQ ID:84 Designed oligonucleotide primer for PCR
SEQ ID:85 Designed oligonucleotide primer for PCR
SEQ ID:86 Designed oligonucleotide primer for PCR
SEQ ID:87 Designed oligonucleotide primer for PCR
SEQ ID:88 Designed oligonucleotide primer for PCR
SEQ ID:89 Designed oligonucleotide primer for PCR
SEQ ID:90 Designed oligonucleotide primer for PCR
SEQ ID:91 Designed oligonucleotide primer for PCR
SEQ ID:92 Designed oligonucleotide primer for PCR
SEQ ID:93 Designed oligonucleotide primer for PCR
SEQ ID:94 Designed oligonucleotide primer for PCR
SEQ ID:95 Designed oligonucleotide primer for PCR
SEQ ID:96 Designed oligonucleotide primer for PCR
SEQ ID:97 Designed oligonucleotide primer for PCR
SEQ ID:98 Designed oligonucleotide primer for PCR
SEQ ID:99 Designed oligonucleotide primer for PCR
SEQ ID:100 Designed oligonucleotide primer for PCR
SEQ ID:101 Designed oligonucleotide primer for PCR
SEQ ID:102 Designed oligonucleotide primer for PCR
SEQ ID:103 Designed oligonucleotide primer for PCR
SEQ ID:104 Designed oligonucleotide primer for PCR
SEQ ID:105 Designed oligonucleotide primer for PCR
SEQ ID:106 Designed oligonucleotide primer for PCR
SEQ ID:107 Designed oligonucleotide primer for PCR
SEQ ID:108 Designed oligonucleotide primer for PCR
SEQ ID:109 Designed oligonucleotide primer for PCR
SEQ ID:110 Designed oligonucleotide primer for PCR
SEQ ID:111 Designed oligonucleotide probe for Southern hybridization
SEQ ID:112 Designed oligonucleotide probe for Southern hybridization
SEQ ID:113 Designed oligonucleotide probe for Southern hybridization
SEQ ID:114 Designed oligonucleotide probe for Southern hybridization
SEQ ID:115 Designed oligonucleotide probe for Southern hybridization
SEQ ID:116 Designed oligonucleotide probe for Southern hybridization
SEQ ID:117 Designed oligonucleotide probe for Southern hybridization
SEQ ID:118 Designed oligonucleotide probe for Southern hybridization
SEQ ID:119 Designed oligonucleotide probe for Southern hybridization
SEQ ID:120 Designed oligonucleotide probe for Southern hybridization
SEQ ID:121 Designed oligonucleotide probe for Southern hybridization
SEQ ID:122 Designed oligonucleotide probe for Southern hybridization
SEQ ID:123 Designed oligonucleotide probe for Southern hybridization SEQ ID:124 Designed oligonucleotide probe for Southern hybridization
SEQ ID:125 Designed oligonucleotide probe for Southern hybridization
SEQ ID:126 Designed oligonucleotide probe for Southern hybridization
SEQ ID:127 Designed oligonucleotide probe for Southern hybridization
SEQ ID:128 Designed oligonucleotide probe for Southern hybridization
SEQ ID:129 Designed oligonucleotide probe for Southern hybridization
SEQ ID:130 Designed oligonucleotide probe for Southern hybridization
SEQ ID:131 Designed oligonucleotide probe for Southern hybridization.
SEQ ID:132 Designed oligonucleotide probe for Southern hybridization
SEQ ID:133 Designed oligonucleotide probe for Southern hybridization
SEQ ID:134 Designed oligonucleotide probe for Southern hybridization
SEQ ID:135 Designed oligonucleotide probe for Southern hybridization
SEQ ID:136 Designed oligonucleotide probe for Southern hybridization
SEQ ID:137 Designed oligonucleotide probe for Southern hybridization
SEQ ID:138 Designed oligonucleotide probe for Southern hybridization
SEQ ID:139 Designed oligonucleotide probe for Southern hybridization
SEQ ID:140 Designed oligonucleotide probe for Southern hybridization
SEQ ID:141 Designed oligonucleotide probe for Southern hybridization
SEQ ID:142 Designed oligonucleotide probe for Southern hybridization
SEQ ID:143 Designed oligonucleotide probe for Southern hybridization
SEQ ID:144 Designed oligonucleotide probe for Southern hybridization
SEQ ID:145 Designed oligonucleotide probe for Southern hybridization
SEQ ID:146 Designed oligonucleotide probe for Southern hybridization
SEQ ID:147 Designed oligonucleotide probe for Southern hybridization
SEQ ID:148 Designed oligonucleotide probe for Southern hybridization
SEQ ID:149 Designed oligonucleotide probe for Southern hybridization
SEQ ID:150 Designed oligonucleotide probe for Southern hybridization
SEQ ID:151 Designed oligonucleotide primer for PCR
SEQ ID:152 Designed oligonucleotide for mutagenesis
SEQ ID:153 Designed oligonucleotide for mutagenesis
SEQ ID:154 Designed oligonucleotide for mutagenesis
SEQ ID:155 Designed oligonucleotide for mutagenesis
SEQ ID:156 Designed oligonucleotide for mutagenesis
SEQ ID:157 Designed oligonucleotide for mutagenesis
SEQ ID:158 Designed oligonucleotide primer for PCR
SEQ ID:159 Designed oligonucleotide primer for PCR
SEQ ID:160 Designed oligonucleotide primer for PCR
SEQ ID:161 Designed oligonucleotide for synthesis
SEQ ID:162 Designed oligonucleotide for synthesis
SEQ ID:163 Designed oligonucleotide for synthesis
SEQ ID:164 Designed oligonucleotide primer for PCR
SEQ ID:165 Designed oligonucleotide primer for PCR
SEQ ID:166 Designed oligonucleotide primer for PCR
SEQ ID:167 Designed oligonucleotide primer for PCR
SEQ ID:168 Designed oligonucleotide primer for PCR
SEQ ID:169 Designed oligonucleotide primer for PCR
SEQ ID:170 Designed oligonucleotide primer for PCR
SEQ ID:171 Designed oligonucleotide primer for PCR
SEQ ID:172 Designed oligonucleotide primer for PCR
SEQ ID:173 Designed oligonucleotide primer for PCR
SEQ ID:174 Designed oligonucleotide primer for PCR
SEQ ID:175 Designed oligonucleotide primer for PCR
SEQ ID:176 Designed oligonucleotide primer for PCR
SEQ ID:177 Designed oligonucleotide primer for PCR
SEQ ID:178 Designed oligonucleotide primer for PCR
SEQ ID:179 Designed oligonucleotide primer for PCR
SEQ ID:180 Designed oligonucleotide primer for PCR
SEQ ID:181 Designed oligonucleotide primer for PCR
SEQ ID:182 Designed oligonucleotide primer for PCR
SEQ ID:183 Designed oligonucleotide primer for PCR
SEQ ID:184 Designed oligonucleotide primer for PCR
SEQ ID:185 Designed oligonucleotide primer for PCR
SEQ ID:186 Designed oligonucleotide primer for PCR
SEQ ID:187 Designed oligonucleotide primer for PCR
SEQ ID:188 Designed oligonucleotide primer for PCR
SEQ ID:189 Designed oligonucleotide primer for PCR
SEQ ID:190 Designed oligonucleotide primer for PCR
SEQ ID:191 Designed oligonucleotide primer for PCR
SEQ ID:192 Designed oligonucleotide primer for PCR
SEQ ID:193 Designed oligonucleotide primer for PCR
SEQ ID:194 Designed oligonucleotide primer for PCR
SEQ ID:195 Designed oligonucleotide primer for PCR SEQ ID:196 Designed oligonucleotide primer for PCR
SEQ ID:197 Designed oligonucleotide primer for PCR
SEQ ID:198 Designed oligonucleotide primer for PCR
SEQ ID:199 Designed oligonucleotide primer for PCR
SEQ ID:200 Designed oligonucleotide primer for PCR
SEQ ID:201 Designed oligonucleotide primer for PCR
SEQ ID:202 Designed oligonucleotide primer for PCR
SEQ ID:203 Designed oligonucleotide primer for PCR
SEQ ID:204 Designed oligonucleotide for synthesis
SEQ ID:205 Designed oligonucleotide primer for PCR
SEQ ID:206 Designed oligonucleotide primer for PCR
SEQ ID:207 Designed oligonucleotide primer for PCR
SEQ ID:208 Designed oligonucleotide primer for PCR
SEQ ID:209 Designed oligonucleotide for synthesis
SEQ ID:210 Designed oligonucleotide primer for PCR
SEQ ID:211 Designed oligonucleotide primer for PCR
SEQ ID:212 Designed oligonucleotide primer for PCR
SEQ ID:213 designed oligonucleotide for synthesis

The invention claimed is:

1. An artificial cell comprising: (i) a chromosome which comprises a reporter polynucleotide, wherein the reporter polynucleotide comprises an ERE, a TATA sequence and a reporter sequence heterologous to the ERE; and
 (ii) a mutant ERα which has an activity for transactivation of the reporter polynucleotide,
 wherein in the presence of a partial anti-estrogen and E2 the activity is higher than that of ERα encoded by SEQ ID NO:1 in the presence of the partial anti-estrogen and E2, or in the presence of a partial anti-estrogen the activity is higher than that of ERα encoded by SEQ ID NO:1 in the presence of the partial anti-estrogen, and
 wherein the mutant ERα has an amino acid sequence of an ERα comprising one or more substituted amino acids at one or more relative positions selected from 303, 309, 390, 396, 494 and 578, or two or more substituted amino acids at two or more relative positions selected from 303, 309, 390, 396, 415, 494, 531 and 578, wherein the relative positions are based on a homology alignment to an amino acid sequence shown in SEQ ID NO:1.

2. The artificial cell according to claim 1, wherein the polynucleotide encoding the mutant ERα is operably linked to a promoter and comprised by a vector.

3. The artificial cell according to claim 1, wherein the partial anti-estrogen is tamoxifen, raloxifene or 4-hydroxytamoxifen.

4. The artificial cell according to claim 1, wherein the activity is also an activity for transactivation of the reporter gene which is inhibited in the presence of a pure anti-estrogen.

5. An artificial cell comprising: (i) a chromosome which comprises a reporter polynucleotide, wherein the reporter polynucleotide comprises an ERE, a TATA sequence and a reporter sequence heterologous to the ERE; and
 (ii) a mutant ERα which activates transcription of a polynucleotide downstream from an ERE while exposed to an anti-estrogen which is not antagonistic to an AF1 region of ERα encoded by SEQ ID NO:1 and is antagonistic to an AF2 region of ERα encoded by SEQ ID NO:1, said mutant ERα comprising:
 an amino acid sequence of an ERα comprising one or more substituted amino acids at one or more relative positions selected from 303, 309, 390, 396, 494 and 578, or two or more substituted amino acids at two or more relative positions selected from 303, 309, 390, 396, 415, 494, 531 and 578, wherein the relative positions are based on a homology alignment to an amino acid sequence shown in SEQ ID NO:1.

6. The artificial cell according to claim 5, wherein the mutant ERα is one which also activates transcription of the polynucleotide downstream from an EKE while bound to E2, wherein the activation is not inhibited by the anti-estrogen which is not antagonistic to an AF1 region of ERα encoded by SEQ ID NO:1 and is antagonistic to an AF2 region of ERα encoded by SEQ ID NO:1.

7. An isolated mutant ERα having:
 an activity for transactivation of a reporter polynucleotide, the reporter polynucleotide comprising an EKE, a TATA sequence and a reporter sequence heterologous to the ERE, wherein
 in the presence of a partial anti-estrogen and E2 the activity is higher than that of ERα encoded by SEQ ID NO:1 in the presence of the partial anti-estrogen and E2, or
 in the presence of a partial anti-estrogen the activity is higher than that of ERα encoded by SEQ ID NO:1 in the presence of the partial anti-estrogen; and
 an amino acid sequence of an ERα comprising one or more substituted amino acids at one or more relative positions selected from 303, 309, 390, 396, 494 and 578, or two or more substituted amino acids at two or more relative positions selected from 303, 309, 390, 396, 415, 494, 531 and 578, wherein the relative positions are based on a homology alignment to an amino acid sequence shown in SEQ ID:1.

8. The isolated mutant ERα according to claim 7, wherein the substituted amino acid is an arginine at relative position 303, a phenylalanine at relative position 309, an asparaginic acid at relative position 390, a valine at relative position 396, a valine at relative position 494 or a proline at a relative position 578, wherein the relative positions are based on a homology alignment to an amino acid sequence shown in SEQ ID:1.

9. The isolated mutant ERα according to claim 7, wherein the substituted amino acid is an amino acid other than lysine at relative position 303, an amino acid other than serine at relative position 309, an amino acid other than glycine at relative position 390, an amino acid other than methionine at relative position 396, an amino acid other than glycine at relative position 494 and an amino acid other than serine at relative position 578, wherein the relative positions are based on a homology alignment to an amino acid sequence shown in SEQ ID:1.

10. An isolated mutant ERα having an amino acid sequence shown in SEQ ID:2.

11. An isolated mutant ERα having an amino acid sequence shown in SEQ ID:3.

12. An isolated mutant ERα having an amino acid sequence shown in SEQ ID:4.

13. An isolated mutant ERα having an amino acid sequence shown in SEQ ID:5.

14. An isolated mutant ERα having an amino acid sequence shown in SEQ ID:7.

15. An isolated mutant ERα having an amino acid sequence shown in SEQ ID:9.

16. An isolated mutant ERα having an amino acid sequence shown in SEQ ID:10.

17. An isolated polynucleotide encoding the mutant ERα of claim 7.

18. An isolated polynucleotide encoding the mutant ERα of claim 10.

19. An isolated polynucleotide encoding the mutant ERα of claim 11.

20. An isolated polynucleotide encoding the mutant ERα of claim 12.

21. An isolated polynucleotide encoding the mutant ERα of claim 13.

22. An isolated polynucleotide encoding the mutant ERα of claim 14.

23. An isolated polynucleotide encoding the mutant ERα of claim 15.

24. An isolated polynucleotide encoding the mutant ERα of claim 16.

25. A vector comprising the polynucleotide of claim 17.

26. A virus comprising the vector of claim 25.

* * * * *

```
                          SEQUENCE LISTING

<160> NUMBER OF SEQ ID NOS: 213

<210> SEQ ID NO 1
<211> LENGTH: 595
<212> TYPE: PRT
<213> ORGANISM: Homo sapiens

<400> SEQUENCE: 1

Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
             20                  25                  30

Ile Pro Leu Glu Arg Pro Leu Gly Glu Val Tyr Leu Asp Ser Ser Lys
         35                  40                  45

Pro Ala Val Tyr Asn Tyr Pro Glu Gly Ala Ala Tyr Glu Phe Asn Ala
     50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Ala Phe Gly Ser Asn Gly Leu Gly Gly
                 85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270
```

```
Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Pro Leu Gln Lys Tyr Tyr Ile Thr Gly Glu Ala Glu Gly Phe Pro
            580                 585                 590

Ala Thr Val
        595

<210> SEQ ID NO 2
<211> LENGTH: 595
<212> TYPE: PRT
<213> ORGANISM: Homo sapiens

<400> SEQUENCE: 2

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
```

-continued

```
                  35                  40                  45
Pro Ala Val Tyr Asn Tyr Pro Glu Gly Ala Ala Tyr Glu Phe Asn Ala
 50                  55                  60
Ala Ala Ala Ala Asn Ala Gln Val Tyr Gly Gln Thr Gly Leu Pro Tyr
 65                  70                  75                  80
Gly Pro Gly Ser Glu Ala Ala Ala Phe Gly Ser Asn Gly Leu Gly Gly
                 85                  90                  95
Phe Pro Pro Leu Asn Ser Val Ser Pro Ser Pro Leu Met Leu Leu His
                100                 105                 110
Pro Pro Pro Gln Leu Ser Pro Phe Leu Gln Pro His Gly Gln Gln Val
                115                 120                 125
Pro Tyr Tyr Leu Glu Asn Glu Pro Ser Gly Tyr Thr Val Arg Glu Ala
130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                165                 170                 175
Glu Ser Ala Lys Glu Thr Arg Tyr Cys Ala Val Cys Asn Asp Tyr Ala
                180                 185                 190
Ser Gly Tyr His Tyr Gly Val Trp Ser Cys Glu Gly Cys Lys Ala Phe
                195                 200                 205
Phe Lys Arg Ser Ile Gln Gly His Asn Asp Tyr Met Cys Pro Ala Thr
                210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
                260                 265                 270
Asp Gly Glu Gly Arg Gly Glu Val Gly Ser Ala Gly Asp Met Arg Ala
                275                 280                 285
Ala Asn Leu Trp Pro Ser Pro Leu Met Ile Lys Arg Ser Lys Arg Asn
                290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
                340                 345                 350
Glu Leu Val His Met Ile Asn Trp Ala Lys Arg Val Pro Gly Phe Val
                355                 360                 365
Asp Leu Thr Leu His Asp Gln Val His Leu Leu Glu Cys Ala Trp Leu
                370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
                435                 440                 445
Lys Ser Ile Ile Leu Leu Asn Ser Gly Val Tyr Thr Phe Leu Ser Ser
                450                 455                 460
```

```
Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Pro Leu Gln Lys Tyr Tyr Ile Thr Gly Glu Ala Glu Gly Phe Pro
            580                 585                 590

Ala Thr Val
        595

<210> SEQ ID NO 3
<211> LENGTH: 595
<212> TYPE: PRT
<213> ORGANISM: Homo sapiens

<400> SEQUENCE: 3

Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
             20                  25                  30

Ile Pro Leu Glu Arg Pro Leu Gly Glu Val Tyr Leu Asp Ser Ser Lys
         35                  40                  45

Pro Ala Val Tyr Asn Tyr Pro Glu Gly Ala Ala Tyr Glu Phe Asn Ala
     50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Ala Phe Gly Ser Asn Gly Leu Gly Gly
                 85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
```

```
                225                 230                 235                 240
Arg Leu Arg Lys Cys Tyr Glu Val Gly Met Met Lys Gly Gly Ile Arg
                    245                 250                 255
Lys Asp Arg Arg Gly Gly Arg Met Leu Lys His Lys Arg Gln Arg Asp
                260                 265                 270
Asp Gly Glu Gly Arg Gly Glu Val Gly Ser Ala Gly Asp Met Arg Ala
            275                 280                 285
Ala Asn Leu Trp Pro Ser Pro Leu Met Ile Lys Arg Ser Lys Lys Asn
        290                 295                 300
Ser Leu Ala Leu Phe Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                    325                 330                 335
Phe Ser Glu Ala Ser Met Met Gly Leu Leu Thr Asn Leu Ala Asp Arg
                340                 345                 350
Glu Leu Val His Met Ile Asn Trp Ala Lys Arg Val Pro Gly Phe Val
            355                 360                 365
Asp Leu Thr Leu His Asp Gln Val His Leu Leu Glu Cys Ala Trp Leu
        370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                    405                 410                 415
Cys Val Glu Gly Met Val Glu Ile Phe Asp Met Leu Leu Ala Thr Ser
                420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                    485                 490                 495
Leu Gln Gln Gln His Gln Arg Leu Ala Gln Leu Leu Leu Ile Leu Ser
                500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
        530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                    565                 570                 575
His Pro Leu Gln Lys Tyr Tyr Ile Thr Gly Glu Ala Glu Gly Phe Pro
                580                 585                 590
Ala Thr Val
        595

<210> SEQ ID NO 4
<211> LENGTH: 595
<212> TYPE: PRT
<213> ORGANISM: Homo sapiens

<400> SEQUENCE: 4
```

-continued

```
Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
                 20                  25                  30

Ile Pro Leu Glu Arg Pro Leu Gly Glu Val Tyr Leu Asp Ser Ser Lys
             35                  40                  45

Pro Ala Val Tyr Asn Tyr Pro Glu Gly Ala Ala Tyr Glu Phe Asn Ala
         50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Phe Gly Ser Asn Gly Leu Gly Gly
                 85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
370                 375                 380

Glu Ile Leu Met Ile Asp Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
```

-continued

```
               420                 425                 430
Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
            530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 5
<211> LENGTH: 595
<212> TYPE: PRT
<213> ORGANISM: Homo sapiens

<400> SEQUENCE: 5

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190
```

-continued

```
Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Val Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
    515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Pro Leu Gln Lys Tyr Tyr Ile Thr Gly Glu Ala Glu Gly Phe Pro
                580                 585                 590

Ala Thr Val
    595
```

```
<210> SEQ ID NO 6
<211> LENGTH: 595
<212> TYPE: PRT
<213> ORGANISM: Homo sapiens

<400> SEQUENCE: 6

Met Thr Met Thr Leu His Thr Lys Ala Ser Gly Met Ala Leu Leu His
 1               5                  10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380
```

```
Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Val Lys
            405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Pro Leu Gln Lys Tyr Tyr Ile Thr Gly Glu Ala Glu Gly Phe Pro
            580                 585                 590

Ala Thr Val
        595

<210> SEQ ID NO 7
<211> LENGTH: 595
<212> TYPE: PRT
<213> ORGANISM: Homo sapiens

<400> SEQUENCE: 7

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160
```

```
Gly Arg Glu Arg Leu Ala Ser Thr Asn Asp Lys Gly Ser Met Ala Met
            165                 170                 175

Glu Ser Ala Lys Glu Thr Arg Tyr Cys Ala Val Cys Asn Asp Tyr Ala
        180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Val Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575
```

His Pro Leu Gln Lys Tyr Tyr Ile Thr Gly Glu Ala Glu Gly Phe Pro
            580                 585                 590

Ala Thr Val
        595

<210> SEQ ID NO 8
<211> LENGTH: 595
<212> TYPE: PRT
<213> ORGANISM: Homo sapiens

<400> SEQUENCE: 8

Met Thr Met Thr Leu His Thr Lys Ala Ser Gly Met Ala Leu Leu His
  1               5                  10                  15

Gln Ile Gln Gly Asn Glu Leu Glu Pro Leu Asn Arg Pro Gln Leu Lys
             20                  25                  30

Ile Pro Leu Glu Arg Pro Leu Gly Glu Val Tyr Leu Asp Ser Ser Lys
         35                  40                  45

Pro Ala Val Tyr Asn Tyr Pro Glu Gly Ala Ala Tyr Glu Phe Asn Ala
     50                  55                  60

Ala Ala Ala Ala Asn Ala Gln Val Tyr Gly Gln Thr Gly Leu Pro Tyr
 65                  70                  75                  80

Gly Pro Gly Ser Glu Ala Ala Ala Phe Gly Ser Asn Gly Leu Gly Gly
                 85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

```
Glu Leu Val His Met Ile Asn Trp Ala Lys Arg Val Pro Gly Phe Val
            355                 360                 365
Asp Leu Thr Leu His Asp Gln Val His Leu Glu Cys Ala Trp Leu
        370                 375                 380
Glu Ile Leu Met Ile Gly Leu Val Trp Arg Ser Val Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
        450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
Lys Cys Glu Asn Val Val Pro Leu Tyr Asp Leu Leu Leu Glu Met Leu
        530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Ser Leu Gln Lys Tyr Tyr Ile Thr Gly Glu Ala Glu Gly Phe Pro
            580                 585                 590
Ala Thr Val
        595

<210> SEQ ID NO 9
<211> LENGTH: 595
<212> TYPE: PRT
<213> ORGANISM: Homo sapiens

<400> SEQUENCE: 9

Met Thr Met Thr Leu His Thr Lys Ala Ser Gly Met Ala Leu Leu His
1               5                   10                  15
Gln Ile Gln Gly Asn Glu Leu Glu Pro Leu Asn Arg Pro Gln Leu Lys
            20                  25                  30
Ile Pro Leu Glu Arg Pro Leu Gly Glu Val Tyr Leu Asp Ser Ser Lys
        35                  40                  45
Pro Ala Val Tyr Asn Tyr Pro Glu Gly Ala Ala Tyr Glu Phe Asn Ala
    50                  55                  60
Ala Ala Ala Ala Asn Ala Gln Val Tyr Gly Gln Thr Gly Leu Pro Tyr
65                  70                  75                  80
Gly Pro Gly Ser Glu Ala Ala Ala Phe Gly Ser Asn Gly Leu Gly Gly
                85                  90                  95
Phe Pro Pro Leu Asn Ser Val Ser Pro Ser Pro Leu Met Leu Leu His
            100                 105                 110
Pro Pro Pro Gln Leu Ser Pro Phe Leu Gln Pro His Gly Gln Gln Val
```

```
            115                 120                 125
Pro Tyr Tyr Leu Glu Asn Glu Pro Ser Gly Tyr Thr Val Arg Glu Ala
            130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
            210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
            370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
            515                 520                 525

Lys Cys Lys Asn Val Val Pro Leu Tyr Asp Leu Leu Leu Glu Met Leu
530                 535                 540
```

```
Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Pro Leu Gln Lys Tyr Tyr Ile Thr Gly Glu Ala Glu Gly Phe Pro
                580                 585                 590

Ala Thr Val
        595

<210> SEQ ID NO 10
<211> LENGTH: 595
<212> TYPE: PRT
<213> ORGANISM: Homo sapiens

<400> SEQUENCE: 10

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
                20                  25                  30

Ile Pro Leu Glu Arg Pro Leu Gly Glu Val Tyr Leu Asp Ser Ser Lys
            35                  40                  45

Pro Ala Val Tyr Asn Tyr Pro Glu Gly Ala Ala Tyr Glu Phe Asn Ala
        50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
```

```
                305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Asp Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
                500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
        530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                565                 570                 575
His Pro Leu Gln Lys Tyr Tyr Ile Thr Gly Glu Ala Glu Gly Phe Pro
            580                 585                 590
Ala Thr Val
        595

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 11
cctgcgggga cacggtctgc accctgcccg cggcc                               35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 12
```
cagggagctc tcagactgtg gcagggaaac cctct                                  35

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 13
atgatcaaac gctctaagag gaacagcctg gccttgtccc tgacggccg                   49

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 14
ggacaaggcc aggctgttcc tcttagagcg tttgatcatg agcgggctt                   49

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 15
aagaacagcc tggccttgtt cctgacggcc gaccagatgg tcagtgcct                   49

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 16
catctggtcg gccgtcagga acaaggccag gctgttcttc ttagagcgt                   49

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 17
gctagagatc ctgatgattg atctcgtctg gcgctccatg gagc                        44

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 18

-continued

```
gctccatgga gcgccagacg agatcaatca tcaggatctc tagc         44
```

<210> SEQ ID NO 19
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 19

```
tggtctcgtc tggcgctccg tggagcaccc agggaagcta ctgtttgct    49
```

<210> SEQ ID NO 20
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 20

```
agcaaacagt agcttccctg ggtgctccac ggagcgccag acgagacca    49
```

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 21

```
ctcttggaca ggaaccaggt aaaatgtgta gagggcatgg tggagatct    49
```

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 22

```
catgccctct acacatttta cctggttcct gtccaagagc aagttagga    49
```

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 23

```
ccacctgatg gccaaggcag tcctgaccct gcagcagcag cagcagcac    49
```

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 24

```
ggtgctgctg ctgcagggtc aggactgcct tggccatcag gtggatcaa    49
```

```
<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 25
atctgtacag catgaagtgc gagaacgtgg tgcccctcta tgac                    44

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 26
gtcatagagg ggcaccacgt tctcgcactt catgctgtac agat                    44

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 27
gcgggctcta cttcatcgca tcccttgcaa aagtattaca tcacg                   45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence:Designed
      oligonucleotide for mutagenesis

<400> SEQUENCE: 28
cgtgatgtaa tacttttgca agggatgcga tgaagtagag cccgc                   45

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 29
tggagacatg agagctgcca                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 30
acctttggcc aagcccgctc                                               20
```

```
<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 31
ccgctcatga tcaaacgctc                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 32
agggcagggg tgaagtgggg                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 33
ccaacctttg gccaagcccg                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 34
tactcggaat agagtatggg                                                   20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 35
ggctcagcat ccaacaaggc                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 36
tgaccatctg gtcggccgtc                                                   20
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 37
aagggtctgg taggatcata                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 38
catctggtcg gccgtcaggg                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 39
agagctgcca acctttggcc                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 40
aagcccgctc atgatcaaac                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 41
gctctaagaa gaacagcctg                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 42
agacatgaga gctgccaacc                                               20

<210> SEQ ID NO 43
```

```
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 43
ggccaagccc gctcatgatc                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 44
agcttcactg aagggtctgg                                                20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 45
taggatcata ctcggaatag                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 46
agtatggggg gctcagcatc                                                20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 47
caacaaggca ctgaccatct                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 48
aagggtctgg taggatcata                                                20

<210> SEQ ID NO 49
<211> LENGTH: 20
```

```
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 49
gagctggttc acatgatcaa                                                 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 50
tgggcgaaga gggtgccagg                                                 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 51
ttgtggattt gaccctccat                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 52
atcaggtcca ccttctagaa                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 53
gtgcctggct agagatcctg                                                 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 54
tgggtgctcc atggagcgcc                                                 20

<210> SEQ ID NO 55
<211> LENGTH: 20
<212> TYPE: DNA
```

```
<213> ORGANISM: Artificial Sequence
<220> FEATURE:
<223> OTHER INFORMATION: Description of Artificial Sequence:Designed
      oligonucleotide primer for PCR

<400> SEQUENCE: 55
ttaggagcaa acagtagctt                                             20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 56
tggttcctgt ccaagagca                                              19

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 57
tccaccatgc cctctacaca                                             20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 58
agccagcagc atgtcgaaga                                             20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 59
ggctttggtg atttgaccct                                             20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 60
ccatgatcag gtccaccttc                                             20

<210> SEQ ID NO 61
<211> LENGTH: 20
<212> TYPE: DNA
<213> ORGANISM: Artificial Sequence
```

```
<220> FEATURE:
<223> OTHER INFORMATION: Description of Artificial Sequence:Designed
      oligonucleotide primer for PCR

<400> SEQUENCE: 61
tagaatgtgc ctggctagag                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 62
gctggttcac atgatcaact                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 63
gccaggcttt gtggatttga                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 64
atgatgtagc cagcaggtcg                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 65
gccctctaca cattttccct                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 66
aagagcaagt taggagcaaa                                                    20

<210> SEQ ID NO 67
<211> LENGTH: 20
<212> TYPE: DNA
<213> ORGANISM: Artificial Sequence
<220> FEATURE:
```

-continued

```
<223> OTHER INFORMATION: Description of Artificial Sequence:Designed
      oligonucleotide primer for PCR

<400> SEQUENCE: 67
ggatcaaagt gtctgtgatc                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 68
tctccaccat gccctctaca                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 69
ggtctcgtct ggcgctccat                                              20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 70
ggagcaccca gtgaagctac                                              20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 71
tgtttgctcc taacttggac                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 72
tcctgatgat tggtctcgtc                                              20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence:Designed
``` oligonucleotide primer for PCR

<400> SEQUENCE: 73
cacccagtga agctactgtt                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 74
ttcatcatgc ggaaccgaga                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 75
gatgtagcca gcagcatgtc                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 76
aagatctcca ccatgcccct                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 77
ctccaccatg cccctctaca                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 78
atgtcgaaga tctccaccat                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

```
<400> SEQUENCE: 79
agagaaggac catatccacc                                               20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 80
gagtcctgga caagatcaca                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 81
gacactttga tccacctgat                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 82
ccctgaagtc tctggaagag                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 83
acaagatcac agacactttg                                               20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 84
tgtgcctgat gtgggagagg                                               20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR
```

<400> SEQUENCE: 85
atgaggagga gctgggccag                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 86
ccgctggtgc tgctgctgca                                              20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 87
gctgggccag ccgctggtgc                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 88
cctttgttac tcatgtgcct                                              20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 89
aggcacatga gtaacaaagg                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 90
catggagcat ctgtacagca                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 91
ttgtggattt gaccctccat                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 92
ccaccgagtc ctggacaaga                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 93
ggccaaggca ggcctgaccc                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 94
gtaggcggtg ggcgtccagc                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 95
atctccagca gcaggtcata                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 96
cagcaggtca tagaggggca                                              20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 97
cagtggccaa gtggctttgg                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 98
ccacggctag tgggcgcatg                                              20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 99
aagtgcaaga acgtggtgcc                                              20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 100
tctatgacct gctgctggag                                              20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 101
tgctggacgc ccaccgccta                                              20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 102
atgcgcccac tagccgtgga                                              20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 103
gcatccgtgg aggagacgga                                              20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 104
tcccccgtga tgtaatactt                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 105
tctgcctccc ccgtgatgta                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 106
aaaccctctg cctcccccgt                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 107
gtggcaggga aaccctctgc                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 108
actgtggcag ggaaaccctc                                               20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 109
atatgtgtcc agccaccaac                                               20

```
<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 110
tatctgaacc gtgtgggagc                                            20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 111
tgatcaaacg ctctaagaag                                            20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 112
caaacgctct aagaagaaca                                            20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 113
cgctctaaga agaacagcct                                            20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 114
ctaagaagaa cagcctggcc                                            20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 115
gaagaacagc ctggccttgt                                            20
```

```
<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 116
agaacagcct ggccttgtcc                                               20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 117
cagcctggcc ttgtccctga                                               20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 118
ctggccttgt ccctgacggc                                               20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 119
ccttgtccct gacggccgac                                               20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 120
gtccctgacg gccgaccaga                                               20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 121
gagatcctga tgattggtct                                               20

<210> SEQ ID NO 122
```

```
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 122
atcctgatga ttggtctcgt                                                    20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 123
ctgatgattg gtctcgtctg                                                    20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 124
atgattggtc tcgtctggcg                                                    20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 125
attggtctcg tctggcgctc                                                    20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 126
gtctcgtctg gcgctccatg                                                    20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 127
acgtctggcg ctccatggag                                                    20

<210> SEQ ID NO 128
<211> LENGTH: 20
```

-continued

<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 128
ggcgctccat ggaggcaccc                                              20

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 129
gctccatgga ggcacccagg g                                            21

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 130
catggaggca cccagggaag                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 131
tcttggacag gaaccaggga                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 132
ggacaggaac cagggaaaat                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 133
aggaaccagg gaaaatgtgt                                              20

<210> SEQ ID NO 134
<211> LENGTH: 20
<212> TYPE: DNA

```
-continued

<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 134
accagggaaa atgtgtagag                                          20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 135
gggaaaatgt gtagagggca                                          20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 136
acctgatggc caaggcaggc                                          20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 137
gatggccaag gcaggcctga                                          20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 138
gccaaggcag gcctgaccct                                          20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 139
aggcaggcct gaccctgcag                                          20

<210> SEQ ID NO 140
<211> LENGTH: 20
<212> TYPE: DNA
<213> ORGANISM: Artificial Sequence
```

```
<220> FEATURE:
<223> OTHER INFORMATION: Description of Artificial Sequence:Designed
      oligonucleotide probe for Southern hybridization

<400> SEQUENCE: 140
aggcctgacc ctgcagcagc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe for Southern hybridization

<400> SEQUENCE: 141
ctgtacagca tgaagtgcaa                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe for Southern hybridization

<400> SEQUENCE: 142
acagcatgaa gtgcaagaac                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe for Southern hybridization

<400> SEQUENCE: 143
atgaagtgca agaacgtggt                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe for Southern hybridization

<400> SEQUENCE: 144
agtgcaagaa cgtggtgccc                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe for Southern hybridization

<400> SEQUENCE: 145
caagaacgtg gtgcccctct                                              20

<210> SEQ ID NO 146
<211> LENGTH: 20
<212> TYPE: DNA
<213> ORGANISM: Artificial Sequence
<220> FEATURE:
```

```
<223> OTHER INFORMATION: Description of Artificial Sequence:Designed
      oligonucleotide probe  for Southern hybridization

<400> SEQUENCE: 146
gctctacttc atcgcattcc                                                    20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 147
ctacttcatc gcattccttg                                                    20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 148
cttcatcgca ttccttgcaa                                                    20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 149
catcgcattc cttgcaaaag                                                    20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide probe  for Southern hybridization

<400> SEQUENCE: 150
cgcattcctt gcaaaagtat                                                    20

<210> SEQ ID NO 151
<211> LENGTH: 40
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 151
cccagccacc atgaccatga ccctccacac caaagcatct                              40

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence:Designed
```

```
            oligonucleotide primer  for mutagenesis

<400> SEQUENCE: 152
caggctgttc ctcttagagc g                                                    21

<210> SEQ ID NO 153
<211> LENGTH: 31
<212> TYPE: DNA
<213> ORGANISM: Artificial Sequence
<220> FEATURE:
<223> OTHER INFORMATION: Description of Artificial Sequence:Designed
      oligonucleotide primer  for mutagenesis

<400> SEQUENCE: 153
tggtcggccg tcaggaacaa ggccaggctg t                                         31

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence:Designed
      oligonucleotide primer  for mutagenesis

<400> SEQUENCE: 154
gggtgctcca cggagcgcca g                                                    21

<210> SEQ ID NO 155
<211> LENGTH: 31
<212> TYPE: DNA
<213> ORGANISM: Artificial Sequence
<220> FEATURE:
<223> OTHER INFORMATION: Description of Artificial Sequence:Designed
      oligonucleotide primer  for mutagenesis

<400> SEQUENCE: 155
ccctctacac attttacctg gttcctgtcc a                                         31

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence:Designed
      oligonucleotide primer  for mutagenesis

<400> SEQUENCE: 156
tgctgcaggg tcaggactgc cttggccatc a                                         31

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence:Designed
      oligonucleotide primer  for mutagenesis

<400> SEQUENCE: 157
caaagcctgg ctccctcttc gcc                                                  23

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence:Designed
      oligonucleotide primer for PCR
```

```
<400> SEQUENCE: 158
ggaatgatga aaggtgggat acga                                              24

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 159
aatttatgct acaacaaggc aaggc                                             25

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 160
ggagtggcac cttccagggt caag                                              24

<210> SEQ ID NO 161
<211> LENGTH: 33
<212> TYPE: DNA
<213> ORGANISM: Artificial Sequence
<220> FEATURE:
<223> OTHER INFORMATION: Description of Artificial Sequence :Designed
      oligonucleotide  for synthesis

<400> SEQUENCE: 161
tcgacaaagt caggtcacag tgacctgatc aag                                    33

<210> SEQ ID NO 162
<211> LENGTH: 52
<212> TYPE: DNA
<213> ORGANISM: Artificial Sequence
<220> FEATURE:
<223> OTHER INFORMATION: Description of Artificial Sequence :Designed
      oligonucleotide  for synthesis

<400> SEQUENCE: 162
gatctcgact ataaagaggg caggctgtcc tctaagcgtc accacgactt ca               52

<210> SEQ ID NO 163
<211> LENGTH: 52
<212> TYPE: DNA
<213> ORGANISM: Artificial Sequence
<220> FEATURE:
<223> OTHER INFORMATION: Description of Artificial Sequence :Designed
      oligonucleotide  for synthesis

<400> SEQUENCE: 163
agcttgaagt cgtggtgacg cttagaggac agcctgccct ctttatagtc ga               52

<210> SEQ ID NO 164
<211> LENGTH: 26
<212> TYPE: DNA
<213> ORGANISM: Artificial Sequence
<220> FEATURE:
<223> OTHER INFORMATION: Description of Artificial Sequence :Designed
      oligonucleotide primer for PCR
```

```
<400> SEQUENCE: 164
gtggagacat gagagctgcc aacctt                                          26

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 165
gaccatctgg tcggccgtca gggacaaggc caggctaggc                           40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 166
gctcatgatc aaacgctcta agaagaacag cctgcctggg                           40

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 167
aatagagtat gggggctca gcat                                             24

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 168
ggtccacctt ctagaatgtg cctgg                                           25

<210> SEQ ID NO 169
<211> LENGTH: 39
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 169
gcaagttagg agcaaacagt agcttccctg ggtggtgca                            39

<210> SEQ ID NO 170
<211> LENGTH: 25
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 170
```
ccatggagca gggagtgaag ctact                                              25

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 171
cagcatgtcg aagatctcca ccatgccctc tacacatggt                              40

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 172
gagtcctgga caagatcaca gaca                                               24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 173
tgctgtacag atgctccatg cctt                                               24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 174
ctctcccaca tcaggcacat gagt                                               24

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 175
agcatctcca gcagcaggtc atagaggggc accacgagct                              40

<210> SEQ ID NO 176
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 176
gaggcggggt aagggaagta ggtggaagat tcagc            35

<210> SEQ ID NO 177
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 177
gggtggggaa atagggtttc caatgcttca ctggg            35

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 178
cccagccacc atggaagtgc agttagggct gggaagggtc       40

<210> SEQ ID NO 179
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 179
gggtggggaa atagggtttc caatgcttca ctggg            35

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 180
gcgttcacaa gctaagttgt ttatctcggc                  30

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 181
taaatttcac catctactct cccatcactg                  30

<210> SEQ ID NO 182
<211> LENGTH: 38
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 182
ccaccatgga ctccaaagaa tcattaactc ctggtaga         38

```
<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 183
gcagtcactt ttgatgaaac agaagttttt tgata                              35

<210> SEQ ID NO 184
<211> LENGTH: 29
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 184
ccgacccagg aggtggagat ccctccggt                                     29

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 185
ccacaaaatt taattcttta aaag                                          24

<210> SEQ ID NO 186
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 186
ccaccatgac tgagctgaag gcaaagggtc cccgg                              35

<210> SEQ ID NO 187
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 187
cattcacttt ttatgaaaga gaagggtttt cacca                              35

<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 188
gcactcgctg gcctggatgt ggttggattt                                    30
```

```
<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 189
ttcagactgc tctggtctcg ccaaatccac                                      30

<210> SEQ ID NO 190
<211> LENGTH: 34
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 190
ccaccatgga gaccaaaggc taccacagtc tccc                                 34

<210> SEQ ID NO 191
<211> LENGTH: 34
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 191
cagtcacttc cggtggaagt agagcggctt ggcg                                 34

<210> SEQ ID NO 192
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 192
ttgagttact gagtccgatg aatgtgcttg ctctg                                35

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 193
aaatgaggga ccacacagca gaaagatgaa gccca                                35

<210> SEQ ID NO 194
<211> LENGTH: 55
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 194
gccgcggccg cccagccacc atggatataa aaaactcacc atctagcctt aattc          55
```

```
<210> SEQ ID NO 195
<211> LENGTH: 41
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 195
gggtctagaa atgagggacc acacagcaga aagatgaagc c                         41

<210> SEQ ID NO 196
<211> LENGTH: 37
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 196
tggaattgaa gtgaatggaa cagaagccaa gcaaggt                              37

<210> SEQ ID NO 197
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 197
tggccgcctg aggctttaga cttcctgatc ctcaa                                35

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 198
cccagccacc atggaacaga agccaagcaa ggtggagtgt                           40

<210> SEQ ID NO 199
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 199
tggccgcctg aggctttaga cttcctgatc ctcaa                                35

<210> SEQ ID NO 200
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 200
ttactaacct ataacccca acagtatgac agaaa                                 35

<210> SEQ ID NO 201
```

-continued

```
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 201
cagtctaatc ctcgaacact tccaggaaca aaggg                               35

<210> SEQ ID NO 202
<211> LENGTH: 40
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 202
cccagccacc atgacagaaa atggccttac agcttgggac                          40

<210> SEQ ID NO 203
<211> LENGTH: 35
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 203
cagtctaatc ctcgaacact tccaggaaca aaggg                               35

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence :Designed
      oligonucleotide for synthesis

<400> SEQUENCE: 204
tcaggtcatt ccaggtcatg                                                20

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 205
agaagccttt gggtctgaag tgtctgtgag                                     30

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 206
atggctgagg tctcaaggga ccggggaaaa                                     30

<210> SEQ ID NO 207
<211> LENGTH: 33
```

```
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 207
ccaccatgga ggcaatggcg gccagcactt ccc                                    33

<210> SEQ ID NO 208
<211> LENGTH: 32
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 208
tagtcaggag atctcattgc caaacacttc ga                                     32

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence :Designed
      oligonucleotide for synthesis

<400> SEQUENCE: 209
tcaggtcaca gaggtcatg                                                    19

<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 210
ggattgatct tttgctagat agagacaaaa                                        30

<210> SEQ ID NO 211
<211> LENGTH: 33
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 211
ctagtacaag tccttgtaga tctcctgcag gag                                    33

<210> SEQ ID NO 212
<211> LENGTH: 33
<212> TYPE: DNA
<213> ORGANISM: Artificial Sequence
<220> FEATURE:
<223> OTHER INFORMATION: Description of Artificial Sequence :Designed
      oligonucleotide primer for PCR

<400> SEQUENCE: 212
ccaccatggg tgaaactctg ggagattctc cta                                    33

<210> SEQ ID NO 213
<211> LENGTH: 17
<212> TYPE: DNA
```

```
<213> ORGANISM: Artificial Sequence
<220> FEATURE:
<223> OTHER INFORMATION: Description of Artificial Sequence :Designed
      oligonucleotide  for synthesis

<400> SEQUENCE: 213
tcaggtcaca ggtcatg                                                        17
```